US012146176B2

(12) United States Patent
Tsuruta et al.

(10) Patent No.: US 12,146,176 B2
(45) Date of Patent: Nov. 19, 2024

(54) PRODUCTION OF ISOPRENOIDS

(71) Applicant: AMYRIS, INC., Emeryville, CA (US)

(72) Inventors: Hiroko Tsuruta, Oakland, CA (US); Jacob R. Lenihan, Emeryville, CA (US); Rika Regentin, Hayward, CA (US)

(73) Assignee: AMYRIS, INC., Emeryville, CA (US)

( * ) Notice: Subject to any disclaimer, the term of this patent is extended or adjusted under 35 U.S.C. 154(b) by 0 days.

(21) Appl. No.: 18/208,030

(22) Filed: Jun. 9, 2023

(65) Prior Publication Data

US 2024/0035061 A1    Feb. 1, 2024

Related U.S. Application Data

(63) Continuation of application No. 12/234,589, filed on Sep. 19, 2008, now Pat. No. 11,725,225.

(60) Provisional application No. 60/994,790, filed on Sep. 20, 2007, provisional application No. 61/049,350, filed on Apr. 30, 2008.

(51) Int. Cl.
*C12P 23/00* (2006.01)
*C12N 1/32* (2006.01)
*C12P 5/00* (2006.01)

(52) U.S. Cl.
CPC ............... *C12P 23/00* (2013.01); *C12N 1/32* (2013.01); *C12P 5/007* (2013.01); *Y02E 50/10* (2013.01)

(58) Field of Classification Search
CPC . C12P 23/00; C12P 5/007; C12N 1/32; Y02E 50/10
See application file for complete search history.

(56) References Cited

U.S. PATENT DOCUMENTS

| | | | |
|---|---|---|---|
| 6,825,002 | B2 | 11/2004 | Tsubokura et al. |
| 7,399,323 | B2 | 7/2008 | Renninger et al. |
| 7,501,268 | B2 | 3/2009 | Ohto et al. |
| 2005/0181490 | A1 | 8/2005 | Cheong et al. |
| 2008/0083158 | A1 | 4/2008 | Renninger et al. |
| 2008/0092829 | A1 | 4/2008 | Renninger et al. |
| 2008/0274523 | A1 | 11/2008 | Renninger et al. |
| 2009/0020089 | A1 | 1/2009 | Ryder et al. |
| 2009/0020090 | A1 | 1/2009 | Ryder et al. |
| 2011/0039299 | A1 | 2/2011 | Bailey et al. |

FOREIGN PATENT DOCUMENTS

| | | |
|---|---|---|
| CA | 2 831 321 A1 | 1/2000 |
| JP | 2005-080625 A | 3/2005 |
| WO | WO 2001/042476 A1 | 6/2001 |
| WO | WO 2002/053746 A1 | 7/2002 |
| WO | WO 2003/102200 A2 | 12/2003 |
| WO | WO 2005/047486 A2 | 5/2005 |
| WO | WO 2007/139924 A2 * | 12/2007 ................ C12P 7/00 |
| WO | WO 2008/042338 A2 | 4/2008 |

OTHER PUBLICATIONS

Excerpt from https://en.wikipedia.org/wiki/Yeast, 1 page; this page was last edited on May 17, 2023, at 14:39 (UTC).
"Facts and Evidence and Arguments in support of Opposition" filed by Ajinomoto Co., Inc. against EP Patent No. 2217711, dated May 25, 2016, 61 pages.
"Maximum Dissolved Oxygen Concentration Saturation Table" taken from: http://dnr.mo.govienviesp/wqm/DOSaturationTable.htm, 1page.
A guide to conductivity and dissolved oxygen, Mettler-Toledo (Rev. D2/97), 4 pages.
Barberel et al., The Effect of Aeration upon the Secondary Metabolism of Microorganisms. Biotechnol Genet. Eng. Rev., 2000, vol. 1: 281-323.
Carrau et al., "De novo synthesis of monoterpenes by *Saccharomyces cerevisiae* wine yeasts," Ferns Microbiology Letters, Feb. 2005, vol. 243, No. 1, pp. 107-115.
Choi et al. "Restricted electron flux increases coenzyme $Q_{10}$ production in *Agrobacterium tumefaciens* ATCC4452," *Process Biochemistry*, 2005, vol. 40, pp. 3225-3229.
D. Ro et al. "Production of the Antimalarial Drug Precursor Artemisinic Acid in Engineered Yeast", Nature, 440:940-943 (Apr. 2006).
Gu et al., "Ethanol increases caratenoid production in Phaffia rhodozyma," Journal of Industrial Microbiology and Biotechnology, Jan. 1997, vol. 19, No. 2, pp. 114-117.
Gupta et al. "A Study of Oxygen Transfer in Shake Flasks Using a Non-Invasive Oxygen Sensor," *Biotechnology and Bioengineering*, Nov. 5, 2003, vol. 84, No. 3, pp. 351-358.
Kaplan et al. "Effect of Oxygen on Ubiquinone-10 Production by *Paracoccus denitrificans,*" *Biotechnology Letters*, Oct. 1993, vol. 15, No. 10, pp. 1001-1002.
L.M.D. Santopietro et al. "Fed-Batch and Continuous Culture of Phaffia rhodozyma" Folia Microbiologica 43(2): 169-172 (1998).
Lenihan et al., "Developing an industrial artemisinic acid fermentation process to support the cost-effective production of antimalarial artemisinin-based combination therapies," Biotechnology Progress, Sep. 2008, vol. 24, No. 5, pp. 1026-1032.
Letter to the European Patent Office dated Nov. 22, 2017 by Ajinomoto, Co., for Opposition to European Patent No. 2217711 for submission of further documents, 8 pages.
Luttik, M et al. 1998. "The *Saccharomyces cerevisiae* NDE1 and NDE2 Genes Encode Separate Mitochondrial NADH Dehydrogenases Catalyzing the Oxidation of Cytosolic NADH." *The Journal of Biological Chemistry* 273(38):24529-24534.

(Continued)

*Primary Examiner* — Ganapathirama Raghu
(74) *Attorney, Agent, or Firm* — Squire Patton Boggs (US) LLP

(57) ABSTRACT

Provided herein are methods for a robust production of isoprenoids via one or more biosynthetic pathways. Also provided herein are nucleic acids, enzymes, expression vectors, and genetically modified host cells for carrying out the subject methods. Also provided herein are fermentation methods for high productivity of isoprenoids from genetically modified host cells.

15 Claims, 30 Drawing Sheets

Specification includes a Sequence Listing.

(56) References Cited

OTHER PUBLICATIONS

M.C.Y. Chang et al. Production of Isoprenoid Pharmaceuticals by Engineered Microbes, Nature Chemical Biology 2(12):674-681.
Martin et al. "Engineering a mevalonate pathway in *Escherichia coli* for production of terpenoids," *Nature Biotechnology*, Jul. 2003, vol. 21, No. 7, pp. 796-802.
Maury et al., Microbial Isoprenoid Production: An Example of Green Chemistry through Metabolic Engineering. Adv Biochem Engin/Biotechnol., 2005, vol. 100: 19-51.
Nature Lipidomics Gateway Database C15 and C20 isopreniods web pages. http://www.lipidmaps.org/data/structure/LMSDSearch.php retrieved on Nov. 3, 2011.
Newman et al. "High-level production of amorpha-4,11-diene in a two-phase partitioning bioreactor of metabolically engineered *Escherichia coli*," Biotechnology and Bioengineering, Nov. 2006, vol. 95, No. 4, pp. 684-691.
Operating instructions for Hamilton OxyFerm™ DO sensors, 2016, 7 pages.
PCT International Search Report dated Dec. 12, 2007, for International Application No. PCT/US2007/012467, filed May 25, 2007.
PCT International Search Report dated Jun. 25, 2009, for International Application No. PCT/US2008/010886, filed Sep. 19, 2008.
Response to the Summons to the European Patent Office dated Nov. 7, 2017 by AJINOMOTO, Co., along with the facts and evidence and arguments in support of Opposition, to European Patent No. 2217711, 63 pages.
Ro et al., "Production of the antimalarial drug precursor artemisinic acid in engineered yeast," Nature, Apr. 2006, vol. 440, No. 7086, pp. 940-943.
Rosenfeld et al., Role of the non-respiratory pathways in the utilization of molecular oxygen by *Saccharomyces cerevisiae*. Yeast, 2003, vol. 20: 1115-1114.
Sonderegger, M. and U. Sauer. 2003. "Evolutionary Engineering of *Saccharomyces cerevisiae* for Anaerobic Growth on Xylose." *Applied and Environmental Microbiology* 69(4):1990-1998.
Song, "A Soluble Form of Phosphatase in *Saccharomyces cerevisiae* Capable of Converting Farnesyl Diphosphate Into E,E-Farnesol", Applied Biochemistry and Biotechnology, vol. 128, 2006, pp. 149-157.
Stanbury, P.F. et al. 1995. *Principles of Fermentation Technology*. Elsevier Science Ltd. (Burlington, Massachusetts), pp. 222-223.
Non-Final Office Action dated Dec. 5, 2008, for U.S. Appl. No. 11/807,048, filed May 25, 2007.
Non-Final Office Action dated Oct. 2, 2008, for U.S. Appl. No. 11/807,048, filed May 25, 2007.
Vasala et al. "A new wireless system for decentralised measurement of physiological parameters from shake flasks," *Microbial Cell Factories*, 2006, vol. 5, No. 8 (6 pages).
Veen et al., "Combined overexpression of genes of the ergosterol biosynthetic pathway leads to accumulation of sterols in *Saccharomyces cerevisiae*," Ferns Yeast Research, Oct. 2003, vol. 4, No. 1, pp. 87-95.
Y. Yamane et al. "Astaxanthin Production by Phaffia rhodozyma Enhanced in Fed=Batch Culture With Glucose and Ethanol Feeding", Biotechnology Letters 19(11): 1109-1111 (1997).

\* cited by examiner

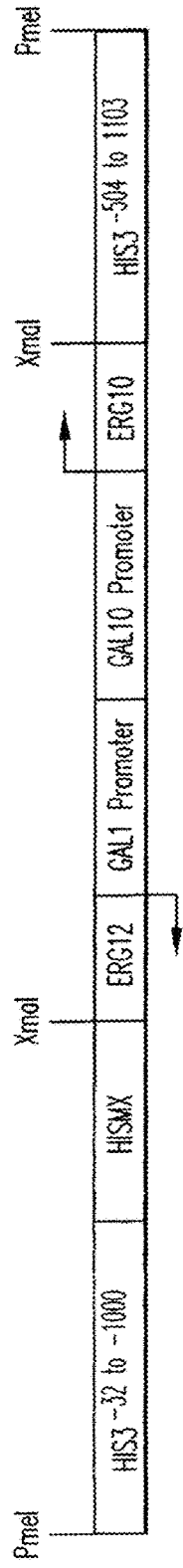
FIG.4D
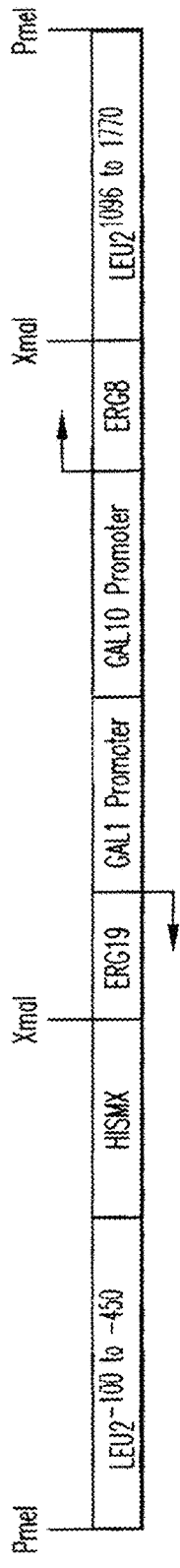
FIG.4E
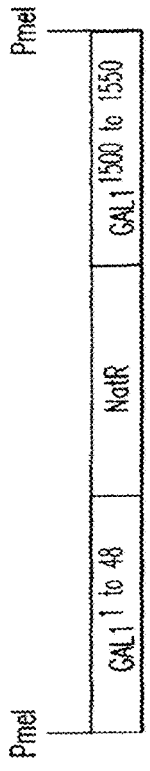
FIG.4F
FIG.4G

SEQUENCE LISTING

```
Sequence total quantity: 73
SEQ ID NO: 1            moltype = DNA  length = 5050
FEATURE                 Location/Qualifiers
misc_feature            1..5050
                        note = ERG20-PGAL-tHMGR insert of pAM489
source                  1..5050
                        mol_type = other DNA
                        organism = synthetic construct
SEQUENCE: 1
gtttaaacta ctattagctg aattgccact gctatcgttg ttagtggcgt tagtgcttgc   60
attcaaagac atggagggcg ttattacgcc ggagctcctc gacagcagat ctgatgactg  120
gtcaatatat ttttgcattg aggctctgtt tggaattata ttttgagatg acccatctaa  180
tgtactggta tcaccagatt tcatgtcgtt ttttaaagcg gctgcttgag tcttagcaat  240
agcgtcacca tctggtgaat cctttgaagg aaccactgac gaaggtttgg acagtgacga  300
agaggatctt tcctgctttg aattagtcgc gctgggagca gatgacgagt tggtggagct  360
gggggcagga ttgctggccg tcgtgggtcc tgaatgggtc cttggctggt ccatctctat  420
tctgaaaacg gaagaggagt agggaatatt actggctgaa aataagtctt gaatgaacgt  480
atacgcgtat atttctacca atctctcaac actgagtaat ggtagttata agaaagagac  540
cgagttaggg acagttagag gcggtggaga tattccttat ggcatgtctg gcgatgataa  600
aactttcaa acggcagccc cgatctaaaa gagctgacac ccgggttaaa aaaaatcctt  660
ggactagtca cgtggaacgg tagatcgaga gatactatct taaagcttat actatattat  720
attggaagta tatagttctt atacatggtc cttatctagt ttgaaatcta atgtttatc   780
gattagcgtt agttctattt gcttctcttg taaactttgt tcaagaacgc agttaagaca  840
```

```
tcagctttga agccacgaga ctcatcgacc tgagaaattt tggccttcaa atccttggca    900
atagactctt catattcgtg gtatagctgt tcaattttca agtcattgaa aatcttttg     960
catttggctt ctgcgactga gtccttctta ccgtaatttt cgtctaaagt ctttctttgt   1020
tctgcgaag caagttccaa tgccttgttg attacccaag aacatttgtt atcttggata   1080
tctgtaccga tcttaccgat ctgttctggg gtaccgaagc agtctaagta gtcatcttga   1140
atttggaagt attcacccaa tggaatcaag acatctctgg cttgtttcaa atcctttca    1200
tccgtgatac cggcaacgta catggccaat gcgacaggca agtagaaaga atagtaagca   1260
gtcttgaaag taactatgaa ggagtgcttc tttagggaga acttactcaa gtcgactttg   1320
tcttcaggtg cagtgattaa gtccatcaat tggcccaatt cggtttggaa ggtgacctca   1380
tggaacaatt cggtgatatc tatgtagtat ttttcgtttc tgaagtgaga tttcaaaagc   1440
ttgtagatag cagcctctaa catgaatgcg tcattgatgg caatttcccc aacttcagga   1500
accttgtacc aacatggttg gcctcttctg gtaatggact tgtccatcat atcatcggcg   1560
accaagaagt aagcctgcaa caactcaatg caccaaccta gaatggcaac cttttcgtat   1620
tcttcttgcc ccaattgttc aacggtcttg ttggagagaa tagcatacgt gtccacaacg   1680
gacaaacctc tatttagctt accgcctgga gtgttgtagt tcaatgagtg ggcataccag   1740
tcacatgctt cctaggcat accgtaagcc aaaagcgatg cgttcaattc ctctactaat   1800
ttagggaaaa cgttcaagaa tctctctctc ctaatttctt tttctgaagc catttatatt   1860
gaattttcaa aaattcttac tttttttttg gatggacgca aagaagttta ataatcatat   1920
tacatggcaa taccaccata tacatatcca tatctaatct tacttatatg ttgtggaaat   1980
gtaaagagcc ccattatctt agcctaaaaa aaccttctct ttggaactt cagtaatacg    2040
cttaactgct cattgctata ttgaagtacg gattagaagc cgccgagcgg gcgacagccc   2100
tccgcaagga gactctcctc cgtgcgtcct ggtcttcacc ggtcgcgttc ctgaaacgca   2160
gatgtgcctc gcgccgcact gctccgaaca ataaagattc tacaatacta gctttatgt    2220
ttatgaagag gaaaaattgg cagtaacctg gccccacaaa ccttcaaatc aacgaatcaa   2280
attaacaacc ataggataat aatgcgatta gttttttagc cttatttctg gggtaattaa   2340
tcagcgaagc gatgatttt gatctattaa cagatatata aatgcaaaag ctgcataacc    2400
actttaacta atactttcaa catttctggt ttgtattact tcttattcaa atgtcataaa   2460
agtatcaaca aaaaattgtt aatataccct tatacttaa cgtcaaggag aaaaaactat    2520
aatggctgca gaccaattgg tgaagactga agtcaccaag aagtctttta ctgctcctgt   2580
acaaaaggct tctacaccag ttttaaccaa taaaacagtc atttctggat cgaaagtcaa   2640
aagtttatca tctgcgcaat cgagctcatc aggaccttca tcatctagtg aggaagatga   2700
ttcccgcgat attgaaagct tggataagaa aatacgtcct ttagaagaat tagaagcatt   2760
attaagtagt ggaaatacaa aacaattgaa gaacaaagag gtcgctgcct tggttattca   2820
cggtaagtta cctttgtacg ctttggagaa aaaattaggt gatactacga gagcggttgc   2880
ggtacgtagg aaggctcttt caattttggc agaagctcct gtattagcat ctgatctttt   2940
accatataaa aattatgact acgaccgcgt atttggcgct tgttgtgaaa atgttatagg   3000
ttacatgcct ttgccgttg gtgttatagg ccccttggtt atcgatggta catcttatca    3060
tataccaatg gcaactacag agggttgttt ggtagcttcc gccatgcgtg gctgtaaggc   3120
aatcatgct ggcggtggtg caacaactgt tttaactaag gatgctgtatga caagaggccc   3180
agtagtccgt ttcccaactt tgaaaagatc tggtgcctgt aagatatggt tagactcaga   3240
agagggacaa aacgcaatta aaaaagcttt taactctaca tcaagatttg cacgtctgca   3300
acatattcaa acttgtctag caggagattt actcttcatg agatttagaa caactactgg   3360
tgacgaatg ggtatgaata tgatttctaa gggtgtcgaa tactcattaa agcaaatggt    3420
agaagagtat ggctgggaag atatggaggt tgtctccgtt tctggtaact actgtaccga   3480
caaaaaacca gctgccatca actggatcga aggtcgtggt aagagtgtcg tcgcagaagc   3540
tactattcct ggtgatgttg tcagaaaagt gttaaaagt gatgtttccg cattggttga    3600
gttgaacatt gctaagaatt tggttgatc tgcaatggct gggtctgttg gtggatttaa   3660
cgcacatgca gctaatttag tgacagctgt tttcttggca ttaggacaag atcctgcaca   3720
aaatgtcgaa agttccaact gtataacatt gatgaaagaa gtggacggtg atttgagaat   3780
ttccgtatcc atgccatcca tcgaagtagg taccatcggt ggtggtactg ttctagaacc   3840
acaaggtgcc atgttggact tattaggtgt aagaggccca catgctaccg ctcctggtac   3900
caacgcacgt caattagcaa gaatagttgc ctgtgccgtc ttggcaggtg aattatcctt   3960
atgtgctgcc ctagcagccg gccatttggt tcaaagtcat atgacccaca acaggaaacc   4020
tgctgaacca acaaaaccta acaatttgga cgccactgat ataaatcgtt tgaaagatgg   4080
gtccgtcacc tgcattaaat cctaaactta gtcatacgtc attggtattc tcttgaaaaa   4140
gaagcacaac agcaccatgt gttacgtaaa atatttactt tatagtttgt acgtcataat   4200
ttcttccata ttcaagttc gtgcatatat agaaagaatt ctgttgtgt aattgtcata    4260
actcccggga tatatgtgta ctttgcagtt atgacgccag atggcagtag tggaagatat   4320
tctttattga aaaatagctt gtcaccttac gtacaatctt gatccggagc ttttcttttt   4380
ttgccgatta agaattcggt cgaaaaaaga aaaggagagg gccaagaggg agggcattgg   4440
tgactattga gcacgtgagt atacgtgatt aagcacacaa aggcagcttg gagtatgtct   4500
gttattaatt tcacaggtag ttctggtcca ttggtgaaag tttgcggctt gcagagcaca   4560
gaggccgcag aatgtgctct agattccgat gctgacttgc tgggtattat atgtgtgccc   4620
aatagaaaga gaacaattga cccggttatt gcaaggaaaa tttcaagtct tgtaaaagca   4680
tataaaaata gttcaggcac tccgaaatac ttggttggcg tgtttcgtaa tcaacctaag   4740
gaggatgttt tggctctggt caatgattac ggcattgata tcgtccaact gcatggagat   4800
gagtcgtggc aagaatacca agagttcctc ggtttgccag ttattaaaag actcgtattt   4860
ccaaaagact gcaacatact actcagtgca gcttcacaga aacctcattc gtttattccc   4920
ttgtttgatt cagaagcagg tgggacaggt gaacttttgg atttggaactc gatttctgac   4980
tgggttggaa ggcaagagag ccccgaaagc ttacatttta tgttagctgg tggactgacg   5040
ccgtttaaac                                                          5050

SEQ ID NO: 2         moltype = DNA   length = 5488
FEATURE              Location/Qualifiers
misc_feature         1..5488
                     note = ERG13-PGAL-tHMGR insert of pAM491
source               1..5488
                     mol_type = other DNA
                     organism = synthetic construct
```

```
SEQUENCE: 2
gtttaaactt gctaaattcg agtgaaacac aggaagacca gaaatcctc atttcatcca    60
tattaacaat aatttcaaat gtttatttgc attatttgaa actagggaag acaagcaacg   120
aaacgttttt gaaatttttg agtattttca ataaatttgt agaggactca gatattgaaa   180
aaaagctaca gcaattaata cttgataaga agagtattga gaagggcaac ggttcatcat   240
ctcatggatc tgcacatgaa caaacaccag agtcaaacga cgttgaaatt gaggctactg   300
cgccaattga tgacaataca gacgatgata acaaaccgaa gttatctgat gtagaaaagg   360
attaaagatg ctaagagata gtgatgtatat ttcataaata atgtaattct atatatgtta   420
attacctttt ttgcgaggca tatttatggt gaaggataag ttttgaccat caaagaaggt   480
taatgtggct gtggtttcag ggtccatacc cgggtatata tatatcattg ttattaaata   540
aagagttttc ctagtatata gattaaaaaa ctactctatt aaatgagagc taaaaaaagc   600
aggctgccaa aaaaataaag catttatgaa gggggttcag caagatgcaa tcgatggggg   660
aagattattt tttaacatcg taagatcttc taaatttgtc atcgatgttg gtcaagtagt   720
aaacaccact ttgcaaatgc tcaatggaac cttgaggttt gaagttcttc ttcaaatggt   780
cattttctct caattcgatg gcagcttcgt aatcctttgg agtttcggtg attctcttgg   840
ctaatttgtt agtaatatct aattccttga taatatgttg gacgtcacca acaattttgc   900
aagaatatag agatgcagct aaaccggaac cgtaagaaaa taaccaaca cgcttgcctt   960
gtaagtcgtc agatccaaca tagtttaata gagatgcaaa ggcgcataa acagatgcgg  1020
tgtacatgtt acctgtgttt gttggaacaa tcaaagattg ggcaactctc tctttgtgga  1080
atggcttagc aacattaaca aaagttttt caatgttctt atcggttaaa gattcgtcat  1140
aatcgcgagt agctaattcg gcgtcaactt ctgggaacaa ttgaggattg gctctgaaat  1200
cgttatatag taatctaccg tatgattttg tgaccaattg acaggttgga acatggaaaa  1260
cgttgtagtc gaaatatttc aaaacgttca aagcatccga accagcggga tcgctaacca  1320
accctttaga aatagccttc ttggaataac tcttgtaaac ttgatcaaga gccttgacgt  1380
aacaagttaa tgaaaatga ccatcgacgt aaggatattc gctggtgaaa tctggcttgt  1440
aaaatcgta ggcgtgttcc atgtaagaag ctcttacaga gtcaaataca attggagcat  1500
caggaccgat ccacatagca acagtaccgg caccaccggt tggtcttgcg gcaccttat   1560
cgtagatggc aatatcaccg caaactacaa tggcgtctct accatcccat gcgttagatt  1620
caatccagtt caaagagttg aacaacgcgt tggtaccacc gtaacaggca ttaagcgtgt  1680
caataccttc gacgtcagtg ttttccaccaa acaattgcat caagacagac ttgacagact  1740
tggacttgtc aatcagagtt tcagtaccga cttctaatct accaattttg ttggtgtcga  1800
tgttgtaact cttgatcaac ttagacaaaa cagttaggga catcgagtag atatcttctc  1860
tgtcattgac aaaagacatg ttggtttggc ccagaccaat tgtgtattta ccttgagaaa  1920
cgccatcaaa tttctctagc tcagattggt tgacacattg agttgggatg taaatttgga  1980
tacctttaat accgacattt tgaggtctgg tttttttgtc agcggtcttt tgtttttta   2040
gttcagtcat ttgcaagttt gtattgtgta attgttgttg cttttgcggc ctaagtcttc  2100
ctttaatacc acaccaacaa agtttagttg agagtttcat ttatattgaa ttttcaaaaa  2160
ttcttacttt ttttttggat ggacgcaaag aagtttaata atcatattac atggcaaatac  2220
caccatatac atatccatat ctaatcttac ttatatgttg tggaaatgta aagagcccca  2280
ttatcttagc ctaaaaaaac cttctctttg gaactttcag taatacgctt aactgctcat  2340
tgctatattg aagtacggat tagaagccgc cgagcgggcg acagccctcc gacgaaagac  2400
tctcctccgt gcgtcctggt cttcaccggt cgcgttcctg aaacgcagat gtgcctcgcg  2460
ccgcactgct ccgaacaata aagattctac aatactagct tttatggtta tgaagaggaa  2520
aaattggcag taacctggcc ccacaaacct tcaaatcaac gaatcaaatt aacaaccata  2580
ggataataat gcgattagtt ttttagcctt atttctgggg taattaatca gcgaagcgat  2640
gatttttgat ctattaacag atatataaat gcaaagctg cataaccact ttaactaata  2700
ctttcaacat tttcggtttg tattacttct tattcaaatg tcataaaagt atcaacaaaa  2760
aattgttaat atacctctat actttaacgt caaggagaaa aaactataat ggctgcagac  2820
caattggtga agactgaagt caccaagaag tcttttactg ctcctgtaca aaaggcttct  2880
acaccagttt taaccaataa aacagtcatt tctggatcga agtcaaaag tttatcatct  2940
gcgcaatcga gctcatcagg accttcatca tctagtgagg aaacgatgattc cgcgatatt  3000
gaaagcttgg ataagaaaat acgtccttta gaagaattag aagcattatt aagtagtgga  3060
aatacaaaac aattgaagaa caaagaggtc gctgccttgg ttattcacgg taagttacct  3120
ttgtacgctt tggagaaaaa attaggtgat actacgagag cggttgcggt acgtaggaag  3180
gctcttttcaa tttttggcaga agctcctgta ttagcatctg atcgttttacc ataaaaaat  3240
tatgactacg accgcgtatt tggcgcttgt tgtgaaaatg ttataggtta catgcctttg  3300
cccgttggtg ttataggccc cttgttatc gatggtacat cttatcatat accaatggca  3360
actacagagg gttgtttggt agcttctgcc atgcgtggct gtaaggcaat caatgctggc  3420
ggtggtgcaa caactgtttt aactaaggat gtatgacaa gagccccagt agtccgtttc  3480
ccaactttga aaagatctgg tgcctgtaag atatggttag actcagaaga gggacaaaac  3540
gcaattaaaa aagcttttaa ctctacatca agatttgcac gtctgcaaca tattcaaact  3600
tgtctagcag gagatttact cttcatgaga tttagaacaa ctactggtga cgcaatgggt  3660
atgaatatga tttctaaggg tgtcgaatac tcattaaagc aaatggtaga agagtatggc  3720
tgggaagata tggaggttgt ctccgttct ggtaactact gtaccgacaa aaaccgaagt  3780
gccatcaact ggatcgaagg tcgtggtaag agtgtcgtcg cagaagctac tattcctggt  3840
gatgttgtca gaaaagtgtt aaaaagtgat gtttccgcat tggttgagtt gaacattgct  3900
aagaatttgg ttggatctgc aatggctggg tctgttggtg gatttaacgc acatgcagct  3960
aatttagtga cagctgtttt cttggcatta ggacaagaac ctgcacaaaa tgtcgaaagt  4020
tccaactgta taacattgat gaaagaagtg acggtgatt tgagaatttc cgtatccatg  4080
ccatccatcg aagtaggtac catcggtggt ggtactgttc tagaaccaca aggtgccatg  4140
ttggacttat taggtgtaag aggcccacat gctaccgctc ctggtaccaa cgcacgtcaa  4200
ttagcaagaa tagttgcctg tgccgtcttg caggtgaat tatccttatg tgctgcccta  4260
gcagccggcc atttggttca aagtcatatg acccacaaca ggaaacctgc tgaaccaaca  4320
aaacctaaca atttggacgc cactgataa aatcgtttga aagatgcgta cgtcacctgc  4380
attaaatcct aaacttagtc atacgtcatt ggtattctct tgaaaaagaa gcacaacagc  4440
accatgtgtt acgtaaaaata tttactttat agtttgtacg tcataatttc ttccatatta  4500
caagttcgtg catatataga aagaattctg ttgttgtaat tgtcataact cccgggaagc  4560
ttttcaattc atctttttt tttttgttct tttttttgat tccggtttct ttgaaatttt  4620
tttgattcgg taatctccga gcagaaggaa gaacgaagga aggagcacag acttagattg  4680
```

```
gtatatatac gcatatgtgg tgttgaagaa acatgaaatt gcccagtatt cttaacccaa 4740
ctgcacagaa caaaaacctg caggaaacga agataaatca tgtcgaaagc tacatataag 4800
gaacgtgctg ctactcatcc tagtcctgtt gctgccaagc tatttaatat catgcacgaa 4860
aagcaaacaa acttgtgtgc ttcattggat gttcgtacca ccaaggaatt actggagtta 4920
gttgaagcat taggtcccaa aatttgttta ctaaaaacac atgtggatat cttgactgat 4980
ttttccatgg agggcacagt taagccgcta aaggcattat ccgccaagta caattttta 5040
ctcttcgaag acagaaaatt tgctgacatt ggtaatacag tcaaattgca gtactctgcg 5100
ggtgtataca gaatagcaga atgggcagac attacgaatg cacacggtgt ggtgggccca 5160
ggtattgtta gcggtttgaa gcaggcggcg gaagaagtaa caaaggaacc tagaggcctt 5220
ttgatgttag cagaattgtc atgcaagggc tccctagcta ctggagaata tactaagggt 5280
actgttgaca ttgcgaagag cgacaaagat tttgttatcg gctttattgc tcaaagagac 5340
atgggtggaa gagatgaagg ttacgattgg ttgattatga cacccggtgt gggtttagat 5400
gacaagggag acgcattggg tcaacagtat agaaccgtgg atgatgtggt ctctacagga 5460
tctgacatta ttattgttgg gtttaaac                                  5488

SEQ ID NO: 3           moltype = DNA  length = 4933
FEATURE                Location/Qualifiers
misc_feature           1..4933
                       note = IDI1-PGAL-tHMGR insert of pAM493
source                 1..4933
                       mol_type = other DNA
                       organism = synthetic construct
SEQUENCE: 3
gtttaaacta ctcagtatat taagtttcga attgaagggc gaactcttat tcgaagtcgg  60
agtcaccaca acacttccgc ccatactctc cgaatcctcg tttcctaaag taagtttact 120
tccacttgta ggcctattat taatgatatc tgaataatcc tctattaggg ttggatcatt 180
cagtagcgcg tgcgattgaa aggagtccat gcccgacgtc gacgtgatta gcgaaggcgc 240
gtaaccattg tcatgtctag cagctataga actaacctcc ttgacaccac ttgcggaagt 300
ctcatcaaca tgctcttcct tattactcat tctcttacca agcagagaat gttatctaaa 360
aactacgtgt atttcacctc tttctcgact tgaacacgtc caactcctta agtactacca 420
cagccaggaa agaatggatc cagttctaca cgatagcaaa gcagaaaaca caaccagcgt 480
accccctgtag aagcttcttt gtttacagca cttgatccat gtagccatac tcgaaatttc 540
aactcatctg aaacttttcc tgaaggttga aaaagaatgc cataagggtc acccgaagct 600
tattcacgcc cgggtaaata aagaaaataa agttacata ttactaagga tttttgtcgc 660
ctattttac tattttcag gtgaaatgaa acgttttata tcacatttg ctatgataac 720
aaagttatta tgattttat gtagcctata ttattgacgc gttgttatag cattctatga 780
atttgcctgt cattttccac ttcagaaagg tcatctaatt gctcccacca gttgaataag 840
taattctcgc aaataatctt aaaccaaggc gtaaacttgt aacttgggtc agcaaaacata 900
gttttcaaat catttggtga aacccatttg aagtctctaa cttcattgac gtttgggttg 960
acagtcaagt tttctttagc gttgatctta taaaatagga tgtaatcaat ttcatgttca 1020
ccccatggtt cattgcttgg tgccatgtaa tggattctgt ttaaaaagtg aaacttaccc 1080
cttgtcttag tttcatcttc tggaatacct aattcatgat ctagtttttct caccgccgca 1140
gtaatagcgc ccttaatctt atcgtctagc taccctttca aacctaattc gtcatcaata 1200
catagtggat gagagcagca tgtgttagtc caaagatcag ggaaagttat tttttcagtg 1260
gctctttgtt gtaaaagtaa ttcaccttgt tcattgaaaa taaagacgga gaatgcacga 1320
tgtagtaaac cccttttcaat attttccatt aaatgacaaa ctttcttggt accggcacca 1380
atagcattat cgtcccaatc caaaacaata caattttcat tcattaactt aatttgctcc 1440
tcatcatgac cagaaaaaca tgtttctccg ctttcgtcat ttgacgtctc actagatcgg 1500
gtattaggtc tttgttgtaa tggaataatt tcaggaaact cttccaaaat gtcttcaggt 1560
gtttggtttt gcactaattt ggcgtaacta gatactgcac catggggcat actattgttg 1620
tcggcagtca tttatattga attttcaaaa attcttactt ttttttttgga tggacgcaaa 1680
gaagtttaat aatcatatta catggcatta ccaccatata catatccata tctaatctta 1740
cttatatgtt gtggaaatgt aaagagcccc attatcttag cctaaaaaaa ccttctcttt 1800
ggaactttca gtaatacgct taactgctca ttgctatatt gaagtacgga ttagaagccg 1860
ccgagcgggc gacagccctc cgacggaaga ctctcctccg tgcgtcctcg tcttcaccgg 1920
tcgcgttcct gaaacgcaga gtgtgcctcgc gccgcactgc tccgaacaat aaagattcta 1980
caatactagc ttttatggtt atgaagagga aaaattggca gtaacctggc cccacaaacc 2040
ttcaaattaa cgaatcaaat taacaaccat aggatgataa tgcgattagt ttttttagcct 2100
tatttctggg gtaattaatc agcgaagcga tgattttttga tctattaaca gatatataaa 2160
tggaaaagct gcataaccac tttaactaat acttttcaaca ttttcagttt gtattacttc 2220
ttattcaaat gtcataaaag tatcaacaaa aaattgttaa tatacctcta tactttaacg 2280
tcaaggagaa aaaactataa tggctgcaga ccaattggtg aagactgaag tcaccaagaa 2340
gtcttttact gctcctgtac aaaaggcttc tacaccagtt ttaaccaata aaacagtcat 2400
ttctggatcg aaagtcaaaa gtttatcatc tgcgcaatcc gaccttcatc 2460
atctagtgag gaagatgatt cccgcgatat tgaaagcttg gataagaaaa tacgtccttt 2520
agaagaatta gaagcattat taagtagtgg aaatacaaaa caattgaaga caaagaggt 2580
cgctgccttg gttattcacg gtaagttacc tttgtacgct ttgagaaaaa attaggtga 2640
tactacgaa gcggttgcgg tacgtaggaa ggctctttca attttggcag aagctcctgt 2700
attagcatct gatcgtttac catataaaaa ttatgactac gaccgcgtat ttgcgcttgt 2760
ttgtgaaaat gttataggtt acatgccttt gccccgttggt gttataggcc ccttggttat 2820
cgatggtaca tcttatcata taccaatggc aactacagag ggttgttggg tagcttctgc 2880
catgcgtggc tgtaaggcaa tcaatgctgg cggtggtgca acaactgttt taactaagga 2940
tggtatgaca agaggcccag tagtccgttt cccaactttg aaaagatctg tgcctctaa 3000
gatatggtta gactcagaag agggacaaaa cgcaattaaa aagctttta actctacatc 3060
aagatttgca cgtctgcaac atattcaaac ttgtctagca ggagatttac tcttcatgag 3120
atttagaaca actactggtg acgcaatggg tatgaatatg atttctaagg gtgtcgaata 3180
ctcattaaag caaatggtag aagagtatgg ctgggaagat atggaggttg tctccgtttc 3240
tggtaactac tgtaccgaca aaaaaccagc tgccatcaac tggatcgaag gtcgtggtaa 3300
gagtgtcgtc gcagaagcta ctattcctgg tgatgttgtc agaaaagtgt aaaaagtga 3360
```

```
tgtttccgca ttggttgagt tgaacattgc taagaatttg gttggatctg caatggctgg   3420
gtctgttggt ggatttaacg cacatgcagc taatttagtg acagctgttt tcttggcatt   3480
aggacaagat cctgcacaaa atgtcgaaag ttccaactgt ataacattga tgaaagaagt   3540
ggacggtgat ttgagaattt ccgtatccat gccatccatc gaagtaggta ccatcggtgg   3600
tggtactgtt ctagaaccac aaggtgccat gttggactta ttaggtgtaa gaggcccaca   3660
tgctaccgct cctggtacca acgcacgtca attagcaaga atagttgcct gtgccgtctt   3720
ggcaggtgaa ttatccttat gtgctgccct agcagccggc catttggttc aaagtcatat   3780
gacccacaac aggaaacctg ctgaaccaac aaaacctaac aatttggacg ccactgatat   3840
aaatcgtttg aaagatgggt ccgtcacctg cattaaatcc taaactttagt catacgtcat   3900
tggtattctc ttgaaaaaga agcacaacag caccatgtgt tacgtaaaat atttacttta   3960
tagtttgtac gtcataattt cttccatatt acaagttcgt gcatatatag aaagaattct   4020
gttgttgtaa ttgtcataac tcccgggagt cagtctgact cttgcgagag atgaggatgt   4080
aataaatacta atctcgaaga tgccatctaa tacatatga catacatata tatatatata   4140
cattctatat attcttaccc agattctttg aggtaagacg gttgggtttt atcttttgca   4200
gttggtacta ttaagaacaa tcgaatcata agcattgctt acaaagaata cacatacgaa   4260
atattaacga taatgtcaat tacgaagact gaactggacg gtatattgcc attggtggcc   4320
agaggtaaag ttagagacat atatgaggta gacgctggta cgttgctgtt tgttgctacg   4380
gatcgtatct ctgcatatga cgttattatg gaaaacgaca ttcctgaaaa ggggatccta   4440
ttgaccaaac tgtcagagtt ctggttcaag ttcctgtcca acgatgttcg taatcatttg   4500
gtcgacatcg ccccaggtaa gactatttc gattatctac ctgcaaaatt gagcgaacca   4560
aagtacaaaa cgcaactaga agaccgctct ctattggttc acaaacataa actaattcca   4620
ttggaagtaa ttgtcagagg ctacatcacc ggatctgctt ggaaaagta cgtaaaaaca   4680
ggtactgtgc atggtttgaa acaacctcaa ggacttaaag aatctgtcaaga gttcccagaa   4740
ccaatcttca ccccatcgac caaggctgaa caaggtgaac atgacgaaaa catctctcct   4800
gcccaggccg ctgagctggt gggtgaagat ttgtcacgta gagtggcaga actggctgta   4860
aaactgtact ccaagtgcaa agattatgct aaggagaagg gcatcatcat cgcagacact   4920
aaaattgttta aac                                                     4933

SEQ ID NO: 4           moltype = DNA  length = 6408
FEATURE                Location/Qualifiers
misc_feature           1..6408
                       note = ERG10-PGAL-ERG12 insert of pAM495
source                 1..6408
                       mol_type = other DNA
                       organism = synthetic construct
SEQUENCE: 4
gtttaaacta ttgtgagggt cagttatttc atccagatat aacccgagag gaaacttctt     60
agcgtctgtt ttcgtaccat aaggcagttc atgaggtata tttcgttat tgaagcccag    120
ctcgtgaatg cttaatgctg ctgaactggt gtccatgtcg cctaggtacg caatctccga    180
aggctgcaaa ggttttgtct caagagcaat gttattgtgc accccgtaat tggtcaacaa    240
gtttaatctg tgcttgtcca ccagctctgt cgtaaccttc agttcatcga ctatctgaag    300
aaatttacta ggaatagtgc catggtacag caaccgagaa tggcaatttc tactcgggtt    360
cagcaacgct gcataaacgc tgttggtgcc gtagacatat cgaagatag gattatcatt    420
cataagtttc agagcaatgt ccttattctg gaacttggat ttatggctct tttggtttaa    480
tttcgcctga ttcttgatct cctttagctt ctcgacgtgg gccttttct tgccatatgg    540
atccgctgca cggtcctgtt ccctagcatg tacgtgagcg tatttccttt taaaccacga    600
cgctttgtct tcattcaacg tttcccattg ttttttcta ctattt gctgtgggaa    660
aaacttatcg aaagatgacg acttttttctt aattctcgtt taagagctt ggtgagcgct    720
aggagtcact gccaggtatc gtttgaacac ggcattagtc agggaagtca taacacagtc    780
ctttcccgca atttctttt tctattactc ttggcctcct ctagtacact ctatatttt    840
ttatgcctcg gtaatgattt tcattttttt ttttccacc tagcggatga ctcttttt    900
ttcttagcga ttggcattat cacataatga attatacatt atataaagta atgtgatttc    960
ttcgaagaat atactaaagt ttagcttgcc tcgtccccgc cggtcaccc ggccagcgac   1020
atggaggccc agaatacct ccttgacagt cttgacgtgc gcagctcagg ggcatgatgt   1080
gactgtcgcc cgtacattta gcccatacat ccccatgtat aatcatttgc atccatacat   1140
tttgatgcc gcacgcgcg aagcaaaat tacggctcct cgctgcagac ctgcgagcag   1200
ggaaacgctc ccctcacaga cgcgttgaat tgtcccacg ccgcgcccct gtagagaaat   1260
ataaaggtt aggatttgcc actgaggttc ttctttcata tacttccttt taaaatcttg   1320
ctaggataca gttctcacat cacatccgaa cataaacaac catggcagaa ccagcccaaa   1380
aaaagcaaaa acaaactgtt caggagcgca aggcgtttat ctcccgtatc actaatgaaa   1440
ctaaaattca aatcgctatt tcgctgaatg gtgttatat tcaaataaaa gattcgattc   1500
ttcctgcaaa gaaggatgac gatgtagctt cccaagctac tcagtcacag gtcatcgata   1560
ttcacacagg tgttggcttt ttggatcata tgatccatgc gttggcaaaa cactctggtt   1620
ggtctcttat tgttgaatgt attggtgacc tgcacattga cgatcaccat actaccgaag   1680
attgcggtat cgcattaggg caagcgttca agaagcaat gggtgctgtc cgtggtgtaa   1740
aaagattcgg tactgggttc gcaccattgg atgaggcgct atcacgtgcc gtagtcgatt   1800
tatctagtag accatttgct gtaatcgacc ttggattgaa gagagagatg attggtgatt   1860
tatccactga aatgattcca cacttttggg aaagtttcgc ggaggcggcc agaattactt   1920
tgcatgttga ttgtctgaga ggtttcaacg atcaccacag aagtgagagt gcgttcaagg   1980
ctttggctgt tgccataaga gaagctattt ctagcaatgg caccaatgac gttccctcaa   2040
ccaaaggtgt tttgatgtga agtactgaca ataaaagat tcttgttttc aagaacttgt   2100
catttgtata gttttttat attgtagttg ttctatttta atcaaatgtt agcgtgattt   2160
atatttttt tcgcctcgac atcatctgcc cagatgcgaa gttaagtgcg cagaaagtaa   2220
tatcatgcgt caatcgtatg tgaatgctgg tcgctatact ggtgtcgatt cgatactaac   2280
gccgccatcc acccgggaaa agtaagtcaa aaggcacacc tcagcgtttg agtacctgaa   2340
aaacgatgaa tcgcaaataa aactttaaat tatgcctgtt atacataag ccatttatat   2400
atttatgtat tttatgaaaa agatcatgag aaatcgcag aacgtaatca tatcttttca   2460
atgacaatag aggaagcacc accaccacca ttacaaatgg cggcaacacc gatcttacct   2520
ccttcttgct gtaagatgga tagcagtgta acaaccactc tagcaccaga acaacccaat   2580
```

-continued

```
gggtgaccta gagcaacagc accaccatat acattaacct tagatgggtc tagcttcaaa  2640
atcttagtgt tcaccaaacc gacaaccgaa aaggcttcat tgaattcaaa gtaatcaaca  2700
gaattgatgt cttcgatgcc agcatgtttc aaagcctttg gaactgcaag agatggagcc  2760
catgtaaaat cagctggttg atgagcggcc tcaccccaac ctttgataat agccaaaggc  2820
ttcaaattct tttccttcaa aacttttttcg gaaaccaaga tgcggctgc agcaccatcg  2880
ttgattggag aagcgttagc ggcagtaaca gtaccgtttt cttttttggaa aacagtcctt  2940
gcagatctca atttttcaac gtgtaatcta gcaggttcct cgtccttcgt gacttgagta  3000
tcaggcttac ctctaaatcc cttaatggta acaggtacaa tttcattgtc gaatttacct  3060
tccttttgag atttttggag tttttggtag gattcgatgg caaaattgtc ttgttgttct  3120
ctagtaatat cccaatcacg ggcacacttt tctgcgtgta cacccatggc tagaccatcg  3180
tacgcatcgt tcaacccatc tctttcgaca ccatcaacaa gaacagtttg gccaaatttg  3240
gcacccgcac gggctgctgg catgtagtat ggtgcgttag tcatagattc acaaccacca  3300
gctacgacaa catcagcatt accacatttg atggattgag cacccaaaat gattgccttc  3360
atagcggatg cacagacctt gttaactgtg cttgcaacga tatgattact caaaccggca  3420
gccaaagcaa cttgtctggc cggagcttgg cccaaattgg cagaaagaac gttaccaaaa  3480
ataatttcgt caaaatcctt ggatgcatcc aattctggaa ccttagccaa ggcgcctttt  3540
aaagcaacag cacccaattc cactgctgtc tggaggata gagaaccctg gaatgaacca  3600
attggggttc tggcagtcga tacaatgtaa acgttctgag acatttatat tgaattttca  3660
aaaattctta cttttttttt ggatggacgc aaagaagttt aataatcata ttacatggca  3720
ataccaccat atacatatcc atatctaatc ttacttatat gttgtggaaa tgtaaagagc  3780
cccattatct tagcctaaaa aaaccttctc tttggaactt tcagtaatac gcttaactgc  3840
tcattgctat attgaagtac ggattagaag ccgccgagcg ggcgacagcc ctccgacgga  3900
agactctcct ccgtgcgtcc tggtcttcac cggtcgcgtt cctgaaacgc agatgtgcct  3960
cgcgccgcac tgctccgaac aataaagatt ctacaatact agcttttatg gttatgaaga  4020
ggaaaaattg gcagtaacct ggccccacaa accttcaaat caacgaatca aattaacaac  4080
cataggataa taatgcgatt agttttttag ccttattct ggggtaatta atcagcgaag  4140
cgatgatttt tgatctatta acagatatat aaatgcaaaa gctgcataac cactttaact  4200
aatactttca acattttcgg tttgtattac ttccttattca aatgtcataa aagtatcaac  4260
aaaaaattgt taatataccct ctatacttta acgtcaagga gaaaaaacta taatgtcatt  4320
accgttctta acttctgcac cgggaaaggt tattattttt ggtgaacact ctgctgtgta  4380
caacaagcct gccgtcgctg ctagtgtgtc tgcgttgaga acctacctgc taataagcga  4440
gtcatctgca ccagatacta ttgaattgga cttcccggac attagcttta atcataagtg  4500
gtccatcaat gatttcaatg ccatcaccga ggatcaagta aactcccaaa aattggccaa  4560
ggctcaacaa gccaccgatg gcttgtctca ggaactcgtt agtcttttgg atccgttgtt  4620
agctcaacta tccgaatcct tccactacca tgcagcgttt tgtttcctgt atatgtttgt  4680
ttgcctatgc ccccatgcca agaatattaa gttttcttta aagtctactt tacccatcgg  4740
tgctgggttg ggctcaagcg cctctatttc tgtatcactg gccttagcta tggcctactt  4800
gggggggtta ataggatcta atgacttgga aaagctgtca gaaaacgata agcatatagt  4860
gaatcaatgg gccttcatag gtgaaaagtg tattcacggt acccccttcag gaatagataa  4920
cgctgtggcc acttatggta atgccctgct atttgaaaaa gactcacata atggaacaat  4980
aaacacaaac aattttaagt tcttagatga tttcccagcc attccaatga tcctaaccta  5040
tactagaatt ccaaggtcta caaaagatct tgttgctcgc gttcgtgtgt tggtcaccga  5100
gaaatttcct gaagttatga agccaattct agatgccatg gtgaatgtg ccctacaagg  5160
cttagagatc atgactaagt taagtaaatg taaaggcacc gatgacgagg ctgtagaaac  5220
taataatgaa ctgtatgaac aactattgga attgataaga ataaatcatg gactgctgt  5280
ctcaatcggt gtttctcatc ctggattaga acttattaaa aatctgagcg atgatttgag  5340
aattgctcc acaaaactta ccggtgctgg tggcggcgat tgctctttga ctttgttacg  5400
aagagacatt actcaagagc aaattgacag cttcaaaaag aaattgcaag atgatttttag  5460
ttacgagaca tttgaaacag acttgggtgg gactggctgc tgtttgttaa gcgcaaaaaa  5520
tttgaataaa gatcttaaaa tcaaatccct agtattccaa ttatttgaaa ataaaactac  5580
cacaaagcaa caaattgacg atctattatt gccaggaaac gcgaatttac catggacttc  5640
ataagctaat ttgcgatagg cattatttat tagttgtttt taatcttaac tgtgtatgaa  5700
gttttatgta ataagataag aaagagaaac aaaaaaaaat tttcgtagt atcaattcag  5760
ctttcgaaga cagaatgaaa tttaagcaga ccatcccggg agaggctagc agaattaccc  5820
tccacgttga ttgtctgcga ggcaagaatg atcatcacga tagtgagagt gcgttcaagg  5880
ctcttgcggt tgccataaga gaagccacct cgcccaatgg taccaacgat gttccctcca  5940
ccaaaggtgt tcttatgtag tgacaccgat tatttaaagc tgcagcatac gatatatata  6000
catgtgtata tatgtatacc tatgaatgtc agtaagtatg tatacgaaca gtatgatact  6060
gaagatgaca aggtaatgca tcattctata cgtgtcattc cgtgcgaggc gcgctttcct  6120
ttttctttt tgcttttttct tttttttttct cttgaactcg agaaaaaaaa tataaaagag  6180
atggaggaac gggaaaaagt tagttgtggt gataggtggc aagtggtatt ccgtaagaac  6240
aacaagaaaa gcatttcata ttatggctga actgagcgaa caagtgcaaa atttaagcat  6300
caacgacaac aacgagaatg gttatgttcc tcctcactta agaggaaaac caagaagtgc  6360
cagaaataac agtagcaact acaataacaa caacggcggc gtttaaac       6408
```

SEQ ID NO: 5        moltype = DNA  length = 2357
FEATURE              Location/Qualifiers
misc_feature       1..2357
                        note = ERG8-PGAL-ERG19 insert of pAM497
source               1..2357
                        mol_type = other DNA
                        organism = synthetic construct
SEQUENCE: 5

```
agattctaca atactagctt ttatggttat gaagaggaaa aattggcagt aacctggccc   60
cacaaacctt caaatcaacg aatcaaatta acaaccatag gataataatg cgattagttt  120
tttagcctta tttctggggt aattaatcag cgaagcgatg attttttgatc tattaacaga  180
tatataaatg caaaagctgc ataaccactt taactaatac tttcaacatt ttcggtttgt  240
attacttctt attcaaatgt cataaaagta tcaacaaaaa attgttaata tacctctata  300
ctttaacgtc aaggagaaaa aactataatg accgtttaca cagcatccgt taccgcaccc  360
```

```
gtcaacatcg caacccttaa gtattggggg aaaagggaca cgaagttgaa tctgcccacc    420
aattcgtcca tatcagtgac tttatcgcaa gatgacctca gaacgttgac ctctgcggct    480
actgcacctg agtttgaacg cgacactttg tggttaaatg gagaaccaca cagcatcgac    540
aatgaaagaa ctcaaaattg tctgcgcgac ctacgccaat taagaaagga aatggaatcg    600
aaggacgcct cattgcccac attatctcaa tggaaactcc acattgtctc cgaaaataac    660
tttcctacag cagctggttt agcttcctcc gctgctggct ttgctgcatt ggtctctgca    720
attgctaagt tataccaatt accacagtca acttcagaaa tatctagaat agcaagaaag    780
gggtctggtt cagcttgtag atcgttgttt ggcggatacg tggcctggga aatgggaaaa    840
gctgaagatg gtcatgattc catggcagta caaatcgcag acagctctga ctggcctcag    900
atgaaagctt gtgtcctagt tgtcagcgat attaaaaagg atgtgagttc cactcagggt    960
atgcaattga ccgtggcaac ctccgaacta tttaaagaaa gaattgaaca tgtcgtacca   1020
aagagatttg aagtcatgcg taaagccatt gttgaaaaag atttcgccac ctttgcaaag   1080
gaaacaatga tggattccaa ctctttccat gccacatgtt tggactcttt ccctccaata   1140
ttctacatga atgacacttc caagcgtatc atcagttggt gccacaccat taatcagttt   1200
tacggagaaa caatcgttgc atacacgttt gatgcaggtc aaatgctgt gttgtactac   1260
ttagctgaaa atgagtcgaa actctttgca tttatctata aattgtttgg ctctgttcct   1320
ggatgggaca agaaatttac tactgagcag cttgaggctt tcaaccatca atttgaatca   1380
tctaacttta ctgcacgtga attgatctt gagttgcaaa aggatgttgc cagagtgatt   1440
ttaactcaag tcggttcagg cccacaagaa acaaacgaat ctttgattga cgcaaagact   1500
ggtctaccaa aggaataaga tcaattcgat atgtaacatt tttcttttct tttctttttcc   1560
tttttttaca atagctaatt tacgtttccc tacggtattg tcggaacga ccaagcttca   1620
atttataaat atcttaattt taacagcagt taccacttga atgagaaacc cgggaaagat   1680
tctctttttt tatgatattt gtacataaac tttataaatg aaattcataa tagaaacgac   1740
acgaaattac aaaatggaat atgttcatag ggtagacgaa actatatacg caatctacat   1800
acatttatca agaaggagaa aaaggaggat gtaaaggaat acaggtaagc aaattgatac   1860
taatggctca acgtgataag gaaaaagaat tgcactttaa cattaatatt gacaaggagg   1920
agggcaccac acaaaaagtt aggtgtaaca gaaaatcatg aaactatgat tcctaatta   1980
tatattggag gattttctct aaaaaaaaaa aaatacaaca aataaaaaac actcaatgac   2040
ctgaccattt gatggagttt aagtcaatac cttcttgaac catttcccat aatggtgaaa   2100
gttccctcaa gaattttact ctgtcagaaa cggccttaca gacgtagtcg acctcctctt   2160
cagtactaaa tctaccaata ccaaatctga tggaagaatg ggctaatgca tcatccttac   2220
ccagcgcatg taaacataa gaaggttcta gggaagcaga tgtacaggct gaacccgagg   2280
ataatgcgat atcccttagt gccatcaata aagattctcc ttccacgtag gcgaaagaaa   2340
cgttaacacg tttaaac                                                  2357

SEQ ID NO: 6             moltype = DNA   length = 2121
FEATURE                  Location/Qualifiers
misc_feature             1..2121
                         note = KanMX-PMET3 region from pAM328
source                   1..2121
                         mol_type = other DNA
                         organism = synthetic construct
SEQUENCE: 6
gaattcgccc ttntgatgg cggcgttagt atcgaatcga cagcagtata gcgaccagca      60
ttcacatacg attgacgcat gatattactt tctgcgcact taacttcgca tctgggcaga    120
tgatgtcgag gcgaaaaaaa atataaatca cgctaacatt tgattaaaat agaacaacta    180
caatataaaa aaactataca aatgacaagt tcttgaaaag agaatctttt ttattgtcag    240
tactgattag aaaaactcat cgagcatcaa atgaaactgc aatttattca tatcaggatt    300
atcaatacca tattttgaa aaagccgttt ctgtaatgaa ggagaaaact caccgaggca    360
gttccatagg atgcaagat cctggtatcg gtctgcgatt ccgactcgtc caacatcaat    420
acaacctatt aatttcccct cgtcaaaaat aaggttatca agtgagaaat caccatgagt    480
gacgactgaa tccggtgaga atggcaaaag cttatgcatt tctttccaga cttgttcaac    540
aggccagcca ttacgctcgt catcaaaatc actcgcatca accaaccgt tattcattcg    600
tgattgcgcc tgagcgagac gaaatacgcg atcgctgtta aaaggacaat acaaacagg    660
aatcgaatgc aaccggcgca ggaacactgc cagcgcatca acaatatttt cacctgaatc    720
aggatattct tctaatacct ggaatgctgt tttgccgggg atcgcagtgg tgagtaacca    780
tgcatcatca ggagtacgga taaaatgctt gatggtcgga gaggcataa attccgtcag    840
ccagtttagt ctgaccatct catctgtaac atcattggca acgctacctt tgccatgttt    900
cagaaacaac tctggcgcat cgggcttccc atacaatcga tagattgtcg cacctgattg    960
cccgacatta tcgcgagccc atttatatccc atataaatca gcatccatgt tggaatttaa   1020
tcgcggcctc gaaacgtgag tcttttcctt acccatggtt gtttatgttc ggatgtgatg   1080
tgagaactgt atcctagcaa gattttaaaa ggaagtatat gaaagaagaa cctcagtggc   1140
aaatcctaac cttttatatt tctctacagg ggcgcggcgt ggggacaatt caacgcgtct   1200
gtgaggggag cgtttccctg ctcgcaggtc tgcagcgagg agccgtaatt tttgcttcgc   1260
gccgtgcggc catcaaaatg tatggatgca aatgattata catggggatg tatgggctaa   1320
atgtacgggc gacagtcaca tcatgcccct gagctgcgca cgtcaagact gtcaaggagg   1380
gtattctggg cctccatgtc gctggccggg tgacccggcg gggacgaggc aagctaaaca   1440
gatctgatct tgaaactgag taagatgctc agaatacccg tcaagataag agtataatgt   1500
agagtaatat accaagtatt cagcatattc tcctcttctt ttgtataaat cacggaaggg   1560
atgatttata agaaaaatga atactattac acttcattta ccaccctctg atctagattt   1620
tccaacgata tgtacgtagt ggtataaggt gaggggtcc acagatataa catcgtttaa   1680
tttagtacta acagagactt ttgtcacaac tacatataag tgtacaaata tagtacagat   1740
atgacacact tgtagcgcca acgcgcatcc tacggattgc tgacagaaaa aaggtcacg   1800
tgaccagaaa agtcacgtgt aattttgtaa ctcaccgcat tctagcggtc cctgtcgtgc   1860
acactgcact caacaccata aaccttagca acctccaaag gaaatcaccg tataacaaag   1920
ccacagtttt acaacttagt ctcttatgaa gttacttacc aatgagaaat agaggctctt   1980
tctcgagaaa tatgaatatg gatatatata tatatatata tatatatata tatatatgta   2040
aacttggttc ttttttagct tgtgatctct agcttgggtc tctctctgtc gtaacagttg   2100
tgatatcgna agggcgaatt c                                             2121
```

| SEQ ID NO: 7 | moltype = DNA length = 8425 |
| --- | --- |
| FEATURE | Location/Qualifiers |
| misc_feature | 1..8425 |
| | note = Plasmid pAM426 |
| source | 1..8425 |
| | mol_type = other DNA |
| | organism = synthetic construct |

SEQUENCE: 7

```
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatcga ctacgtcgta aggccgtttc tgacagagta aaattcttga gggaactttc  240
accattatgg gaaatgcttc aagaaggtat tgacttaaac tccatcaaat ggtcaggtca  300
ttgagtgttt tttatttgtt gtattttttt tttttagag aaaatcctcc aatatcaaat  360
taggaatcgt agtttcatga ttttctgtta cacctaactt tttgtgtggt gccctcctcc  420
ttgtcaatat taatgttaaa gtgcaattct ttttccttat cacgttgagc cattagtatc  480
aatttgctta cctgtattcc tttactatcc tccttttct ccttcttgat aaatgtatgt  540
agattgcgta tatagtttcg tctaccctat gaacatattc cattttgtaa tttcgtgtcg  600
tttctattat gaatttcatt tataaagttt atgtacaaat atcataaaaa aagagaatct  660
ttttaagcaa ggatttttct taacttcttcg gcgacagcat caccgacttc ggtggtactg  720
ttggaaccac ctaaatcacc agttctgata cctgcatcca aaacctttt aactgcatct  780
tcaatggcct taccttcttc aggcaagttc aatgacaatt tcaacatcat tgcagcagac  840
aagatagtgg cgatagggtc aaccttattc tttggcaaat ctggagcaga accgtggcat  900
ggttcgtaca aaccaaatgc ggtgttcttg tctggcaaag aggccaagga cgcagatggc  960
aacaaaccca aggaacctgg gataacggag gcttcatcgg agatgatatc accaaacatg 1020
ttgctggtga ttataatacc atttaggtgg gttgggttct taactaggat catggcggca 1080
gaatcaatca attgatgttg aaccttcaat gtagggaatt cgttcttgat ggtttcctcc 1140
acagtttttc tccataatct tgaagaggcc aaaagattag ctttatccaa ggaccaaata 1200
ggcaatggtg gctcatgttg tagggccatg aaagcggcca ttcttgtgat tctttgcact 1260
tctggaacgg tgtattgttc actatcccaa gcgacaccat caccatcgtc ttcctttctc 1320
ttaccaaagt aaatacctcc cactaattct ctgacaacaa cgaagtcagt acctttagca 1380
aattgtggct tgattggaga taagtctaaa agagagtcgg atgcaaagtt acatggtctt 1440
aagttggcgt acaattgaag ttctttacgg atttttagta aaccttgttc aggtctaaca 1500
ctaccggtac cccatttagg accagccaca gcacctaaca aaacggcatc aaccttcttg 1560
gaggcttcca cgcgcctcatc tggaagtggg cacctgtag catcgatagc agcaccacca 1620
attaaatgat tttcgaaatc gaacttgaca ttggaacgaa catcagaaat agctttaaga 1680
accttaatgg cttcggctgt gatttcttga ccaacgtggt cacctggcaa aacgacgatc 1740
ttcttagggg cagacattac aatggtatat ccttgaaata tatataaaaa aaggcgcctt 1800
agaccgctcg gccaaacaac caattacttg ttgagaaata gagtataatt atcctataaa 1860
tataacgttt tgaacacac atgaacaagg aagtacagga caattgattt tgaagagaat 1920
gtggatttg atgtaattgt tgggattcca ttttaataa ggcaataata ttaggtatgt 1980
ggatatacta gaagttctcc tcgaccgtcg atatgcggtg tgaaataccg cacagatgcg 2040
taaggagaaa ataccgcatc aggaaattgt aaacgttaat atttttgttaa aattcgcgtt 2100
aaattttgt taaatcagct cattttttaa ccaataggcc gaaatcggca aaatccctta 2160
taaatcaaaa gaatagaccg agataggggt gagtgttgtt ccagtttgga acaagagtcc 2220
actattaaag aacgtggact ccaacgtcaa agggcgaaaa accgtctatc agggcgatgg 2280
cccactacgt ggaagatccg aggcctagct ttaacgaacg cagaattttc gagttattaa 2340
acttaaaata cgctgaaccc gaacatagaa atatcgaatg ggaaaaaaaa actgcataaa 2400
ggcattaaaa gaggagcgaa ttttttttta ataaaaatct taataatcat taaaagataa 2460
ataatagtct atatatacgt atataaataa aaaatattca aaaaataaaa taaactatta 2520
ttttagcgta aaggatgggg aaagagaaaa gaaaaaaatt gatctatcga tttcaattca 2580
attcaatta tttctttcg gataagaaag caacacctgg caattcctta ccttccaata 2640
attccaaaga agcaccacca ccagtagaga catgggagac ccgggccatg ttagataga 2700
catagggtaa actagcaatg atttgatcaa tgcttgtat tcatctccca ttctcgtaaa 2760
attgtcttta cctgcatatt ggacctctaa aaattggcaa agatatataa cagccataag 2820
taaaggtctt gggatattct tgttgttaa atactctctg tttatgtctt tccaaacgtc 2880
ctccacttcc ttataaatca gtgtctgagc atattcttcg ttgacattgt attccttcat 2940
gtaagattct aaaagagcttg aactatgtt tctctcctgt tccgctttat gagtcatcag 3000
gtcatttaat ctcctaccca gaataccact gtaacggaat aaaggcggag cagatacagc 3060
ccactcaact gattccttag tgaaaatatc gctcattcct agataacagg tagttgttag 3120
caagtttgca ccaccagtga taataactac gggatcgtgc tcttcagttg tcggtatgtg 3180
tccttcatta gcccatttcg cttctaccat tagattcctt acgaattctt taacgaactc 3240
cttcccacag ttgaataaat cagttctacc ttctttggcc agaaactcct ccatttgcact 3300
gtaggtatcc atgaataatt tgtaaatagg cttcatgtat tccggcaacg tgtctaagca 3360
ggtgatcgac catcttttcca cggcttcagt gaaaatcttt aactcctcgt aagttccata 3420
tgcgtcatac gtgtcatcaa taagtgttat cacagcaact gccttagtga aaaaaactct 3480
agctcttgaa tactgggtt cgtaaccaga acctaaaacc caaaaatagc attcaacgat 3540
acgatctctc agacatgggg cattttttctt aatatcaaat ggcttccacc acttgctatc 3600
gtgactcaac tcttccttat gtaggctctg caatagattg aactccagtt tagctaactt 3660
tagcagagtt ttattatggg agtcttgttg ctgatagaag ggtatgtact gggcggcctc 3720
gatccttggc aatctcttcc acaatggttg ctttaaagct ctctggattt cagtgaataa 3780
agcggggttt gtactaaacg cgtcctttgt cataatcgat agccttgatc ttgtgaattc 3840
cagggcatct caagaatta tttcgcccgg aactctcatg gacgtagcct catataattc 3900
caacaatcct tcaacatcat tcgctaacga ttgtttaaaa gcaccattct tgtctttata 3960
gttattaaac acatcacacg tgacatagta tccttgttta cgcatcagcc taaaccataa 4020
gctagacctg tcgccattcc aattatcacc ataggtctcg taaatacatt gcaatgcatg 4080
atcaatttca cgttcaaaat gatacggaat acctaaacgt tgaatctcgt caatcagctt 4140
caacaaattt gcatgtttca taggaatatc caatgcttcc tttaacaact gtcttacttc 4200
```

```
cttctttaga tcgttactta tttgctccac accctgttca acttgttct cataaatcaa  4260
aaattgatcg ccccaaatag aaggtgggaa atttgcaatt ggccttatag gtttctcttc  4320
agtcaaggcc attgttttct gcagatccgg ggttttttct ccttgacgtt aaagtataga  4380
ggtatattaa caatttttg ttgatacttt tattacattt gaataagaag taatacaaac  4440
cgaaaatgtt gaaagtatta gttaaagtgg ttatgcagtt tttgcattta tatatctgtt  4500
aatagatcaa aaatcatcgc ttcgctgatt aattacccca gaaataaggc taaaaaacta  4560
atcgcattat catcctatgg ttgttaattt gattcgttca tttgaaggtt tgtggggcca  4620
ggttactgcc aattttttcct cttcataacc ataaaagcta gtattgtaga atctttattg  4680
ttcggagcag tgcggcgcga ggcacatctg cgtttcagga acgcgaccgg tgaagacgag  4740
gacgcacgga ggagagtctt ccttcggagg gctgtcaccc gctcggccgc ttctaatccg  4800
tactaagatc tgctttaatt tggccggcga acgtggcgag aaaggaaggg aagaaagcga  4860
aaggagcggg cgctagggcg ctggcaagtg tagcggtcac gctgcgcgta accaccacac  4920
ccgccgcgct taatgcgccg ctacagggcg cgtcgcgcca ttcgccattc aggctgcgca  4980
actgttggga agggcgatcg gtgcggcct cttcgccagt acgccagctg cattaatgaa  5040
tcggccaacg cgcggggaga ggcggtttgc gtattgggcg ctcttccgct tcctcgctca  5100
ctgactcgct gcgctcggtc gttcggctgc ggcgagcggt atcagctcac tcaaaggcgg  5160
taatacggtt atccacagaa tcaggggata acgcaggaaa gaacatgtga gcaaaaggcc  5220
agcaaaaggc caggaaccgt aaaaaggccg cgttgctggc gtttttccat aggctccgcc  5280
cccctgacga gcatcacaaa aatcgacgct caagtcagag gtggcgaaac ccgacaggac  5340
tataaagata ccaggcgttt ccccctggaa gctccctcgt gcgctctcct gttccgaccc  5400
tgccgcttac cggatacctg tccgcctttc tcccttcggg aagcgtggcg ctttctcata  5460
gctcacgctg taggtatctc agttcggtgt aggtcgttcg ctccaagctg ggctgtgtgc  5520
acgaaccccc cgttcagccc gaccgctgcg ccttatccgg taactatcgt cttgagtcca  5580
acccggtaag acacgactta tcgccactgg cagcagccac tggtaacagg attagcagag  5640
cgaggtatgt aggcggtgct acagagttct tgaagtggtg gcctaactac ggctacacta  5700
gaaggacagt atttggtatc tgcgctctgc tgaagccagt taccttcgga aaaagagttg  5760
gtagctcttg atccggcaaa caaaccaccg ctggtagcgg tggttttttt gtttgcaagc  5820
agcagattac gcgcagaaaa aaggatctc aagaagatcc tttgatcttt tctacggggt  5880
ctgacgctca gtggaacgaa aactcacgtt aagggatttt ggtcatgaga ttatcaaaaa  5940
ggatcttcac ctagatcctt ttaaattaaa aatgaagttt taaatcaatc taaagtatat  6000
atgagtaaac ttggtctgac agttaccaat gcttaatcag tgaggcacct atctcagcga  6060
tctgtctatt tcgttcatcc atagttgcct gactccccgt cgtgtagata actacgatac  6120
gggagggctt accatctggc cccagtgctg caatgatacc gcgagaccca cgctcaccgg  6180
ctccagattt atcagcaata accagccagc cggaagggc cgagcgcaga agtggtcctg  6240
caactttatc cgcctccatc cagtctatta attgttgccg ggaagctaga gtaagtagtt  6300
cgccagttaa tagtttgcgc aacgttgttg ccattgctac aggcatcgtg gtgtcacgct  6360
cgtcgtttgg tatggcttca ttcagctccg gttcccaacg atcaaggcga gttacatgat  6420
cccccatgtt gtgcaaaaaa gcggttagct ccttcggtcc tccgatcgtt gtcagaagta  6480
agttggccgc agtgttatca ctcatggtta tggcagcact gcataattct cttactgtca  6540
tgccatccgt aagatgcttt tctgtgactg gtgagtactc aaccaagtca ttctgagaat  6600
agtgtatgcg gcgaccgagt tgctcttgcc cggcgtcaat acgggataat accgcgccac  6660
atagcagaac tttaaaagtg ctcatcattg gaaaacgttc ttcggggcga aaactctcaa  6720
ggatcttacc gctgttgaga tccagttcga tgtaacccac tcgtgcaccc aactgatctt  6780
cagcatcttt tactttcacc agcgtttctg ggtgagcaaa aacaggaagg caaaatgccg  6840
caaaaaaggg aataagggcg acacggaaat gttgaatact catactcttc ctttttcaat  6900
attattgaag catttatcag ggttattgtc tcatgagcgg atacatattt gaatgtattt  6960
agaaaaataa acaaataggg gttccgcgca catttccccg aaaagtgcca cctgaacgaa  7020
gcatctgtgc ttcatttgt agaacaaaaa tgcaacgcga gagcgctaat ttttcaaaca  7080
aagaatctga gctgcatttt tacagaacag aaatgcaacg cgaaagcgct attttaccaa  7140
cgaagaatct gtgcttcatt tttgtaaaac aaaaatgcaa cgcgagagcg ctaatttttc  7200
aaacaaagaa tctgagctgc attttttacag aacagaaatg caacgcgaga gcgctatt    7260
accaacaaag aatctatact ttcttttttgt tctacaaaaa tgcatcccga gagcgctatt  7320
tttctaacaa agcatcttag attactttttt ttctcctttg tgcgctctat aatgcagtct  7380
cttgataact ttttgcactg taggtccgtt aaggttagaa gaaggctact ttggtgtcta  7440
ttttctcttc cataaaaaaa gcctgactcc acttcccgcg tttactgatt actagcgaag  7500
ctgcgggtgc atttttcaa gataaaggca tccccgatta tattctatac cgatgtggat  7560
tgcgcatact ttgtgaacag aaagtgatag cgttgatgat tcttcattgg tcagaaaatt  7620
atgaacggtt tcttctattt tgtctctata tactacgtat aggaaatgtt tacattttcg  7680
tattgttttc gattcactct atgaatagtt cttactacaa ttttttttgtc taaagagtaa  7740
tactagagat aaacataaaa aatgtagagg tcgagtttag atgcaagttc aaggagcgaa  7800
aggtggatgg gtaggttata tagggatata gcacagagat atatagcaaa gagatacttt  7860
tgagcaatgt ttgtggaagc ggtattcgca atattttagt agctcgttac agtccggtgc  7920
gtttttggtt ttttgaaagt gcgtcttcag agcgcttttg gttttcaaaa gcgctctgaa  7980
gttcctatac tttctagaga ataggaactt cggaatagga acttcaaagc gtttccgaaa  8040
acgagcgctt ccgaaaatgc aacgcgagct gcgcacatac agctcactgt tcacgtcgca  8100
cctatatctg cgtgttgcct gtatatatat acatgaga agaacggcat agtgcgtgtt  8160
tatgcttaaa tgcgtactta tatgcgtcta tttatgtagg atgaaaggta gtctagtacc  8220
tcctgtgata ttatcccatt ccatgcgggg tatcgtatgc ttccttcagc actaccctt   8280
agctgttcta tatgctgcca ctcctcaatt ggattagtct catccttcaa tgctatcatt  8340
tccttttgata ttggatcata ctaagaaacc attattatca tgacattaac ctataaaat   8400
aggcgtatca cgaggccctt tcgtc                                         8425
```

SEQ ID NO: 8    moltype = DNA  length = 1763
FEATURE         Location/Qualifiers
misc_feature    1..1763
                note = DNA fragment GAL80-50 to -1-NatR- GAL801309 to 1358
source          1..1763
                mol_type = other DNA
                organism = synthetic construct

```
SEQUENCE: 8
ccagcgtata caatctcgat agttggtttc ccgttctttc cactcccgtc cacaggaaac    60
agctatgacc atgattacgc caagcttggt accgagctcg gatccactag taacggccgc   120
cagtgtgctg gaattcgccc ttgtcgacac tagtaataca catcatcgtc ctacaagttc   180
atcaaagtgt tggacagaca actataccag catggatctc ttgtatcggt tcttttctcc   240
cgctctctcg caataacaat gaacactggg tcaatcatag cctacacagg tgaacagagt   300
agcgttatta cagggtttat acggtgattc ctacggcaaa aatttttcat ttctaaaaaa   360
aaaaagaaaa atttttcttt ccaacgctag aaggaaaaga aaaatctaat taaattgatt   420
tggtgatttt ctgagagttc ccttttcat atatcgaatt ttgaatataa aaggagatcg   480
aaaaaatttt tctattcaat ctgttttctg gttttatttg atagtttttt tgtgtattat   540
tattatggat tagtactggt ttatatgggt ttttctgtat aacttctttt tattttagtt   600
tgtttaatct tattttgagt tacattatag ttccctaact gcaagagaag taacattaaa   660
aatgaccact cttgacgaca cggcttaccg gtaccgcacc agtgtcccgg gggacgcgcga   720
ggccatcgag gcactggatg ggtccttcac caccgacacc gtcttccgcg tcaccgccac   780
cggggacggc ttcaccctgc gggaggtgcc ggtggacccg ccctgacca aggtgttccc    840
cgacgacgaa tcggacgacg aatcggacgc cggggaggac ggcgaccgg actcccggac   900
gttcgtcgcg tacggggacg acggcgacct ggcgggcttc gtggtcgtct cgtactccgg   960
ctggaaccgc cggctgaccg tcgaggacat cgaggtccgc ccggagcacc ggggcaggg  1020
ggtcgggcgc gcgttgatgg ggctcgcgac ggagttcgcc cgcgagcggg gcgccgggca  1080
cctctggctg gaggtcacca acgtcaacgc accggcgatc cacgcgtacc ggcggatggg  1140
gttcacccctc tgcggcctgg acaccgccct gtacgacggc accgcctcgg acggcgagca  1200
ggcgctctac atgagcatgc cctgcccctg agttaactt gatactacta gattttttct  1260
cttcatttat aaaatttttg gttataattg aagcttaga agtatgaaaa aatccttttt  1320
tttcattctt tgcaaccaaa ataagaagct tcttttattc attgaaatga tgaatataaa  1380
cctaacaaaa gaaaaagact cgaatatcaa acattaaaaa aaaataaaag aggttatctg  1440
ttttcccatt tagttggagt ttgcattttc taatagatag aactctcaat taatgtggat  1500
ttagttttctc tgttcgttt ttttgtttt gttctcactg tatttacatt tctatttagt  1560
atttagttat tcatataatc ttaacttctc gaggagctca agggcaattc tgcagatatc  1620
catcacactg gcggccgctc gagcatgcat ctagagggcc caattcgccc tatagtgagt  1680
cgtattacaa ttcactggcc gtcgttttac aacaagcatc ttgccctgtg cttggccccc  1740
agtgcagcga acgttataaa aac                                         1763

SEQ ID NO: 9               moltype = DNA  length = 3901
FEATURE                    Location/Qualifiers
misc_feature               1..3901
                           note = GAL74 to 1021-HPH- GAL11637 to 2587 insert of pAM584
source                     1..3901
                           mol_type = other DNA
                           organism = synthetic construct
SEQUENCE: 9
gtttaaacga ggctcaccta acaattcaaa accaaccaag aatttccgaa cagtagctga    60
tctcagtaaa ggtgggtaga aatgcatgtg aaaccaacta ttactcaatt catcaccagt   120
cgcattcaaa ggagcctgat ggatacccat tgagtatgga aaactcgttt caaataaatt   180
atcatactta atagttagtt gctttaaaat cgaggcgagg tcctccttca ccatttggtt   240
aaattggcta attgaggcaa gcttcttctt tgaaatgacc aaggtctcaa atggccagat   300
ggcccagtat ggaacaacaa caataaagga ttcattctcc actacgactc ttgacttctc   360
tcttgattct aatttgacgt aatcggcaaa caaatcagta ttgtgttcac gtttatattt   420
atcaaaagat ttcaattctt gcgaaacttc actaggatg gattctaagc accaagcttg   480
gccatgtgga tgtaagttgg aacaacccat ggctgtacct ttgttttcaa atatttggac   540
atatttgaaa ggcttatgat tttctcttgc ttctctggag agatcgtcag tcaatgcttg   600
ccaagaatta acaatatgaa ccagatctga ttgtttcatt tgtggaatgg ttagattatg   660
attgggcta aaacatatga cgaaacaatt gcctctcaca gattgcactt taagcagcct   720
atttttaaga ttatcctcat tggaatcatt ctgtggtaaa ataggttgat cgagcctaac   780
ggcagcataa tcattgggga aaatatacgt tgattcatat cttgggttta ggttaccagt   840
agctccttttg ttaccaggac atagatagca ttttgggatca tacaatggag ctgtgggctt   900
gtaagcagcc tcctgttgac ctaaccaagg tctttagct ctgtgtggag aaactaagat   960
ccatgaatcg gttagtggat tgtaacgtct atgggaatgg ctagaaaaat caaattcttc  1020
agcagtgtcg cactagtaa tacacatcat cgtcctacaa gttcatcaaa gtgttggaca  1080
gacaactata ccagcatgga tctcttgtat cggttctttt ctcccgctct ctcgcaataa  1140
caatgaacac tgggtcaatc atagcctaca caggtgaaca gagtagcgtt tatacagggt  1200
ttatacggtg attcctacgg caaaaatttt tcatttctaa aaaaaaaag aaaaattttt  1260
ctttccaacg ctagaaggaa agaaaaatc taattaaatt gatttggtga ttttctgaga  1320
gttccctttt tcatatatcg aatttgaat ataaaaggag atcgaaaaaa tttttctatt  1380
caatctgttt tctggtttta tttgatagtt ttttgtta ttattattat ggattagtac  1440
tggtttatat gggttttttct gtataacttc tttttatttt agtttgttta atcttatttt  1500
gagttacatt atagttccct aactgcaaga gaagtaacat taaaaatgaa aaagcctgaa  1560
ctcaccgcga cgtctgtcga agtttctga tcgaaaagt tcgacagcgt ctccgacctg  1620
atgcagctct cggagggcga agaatctcgt gctttcagct tcgatgtagg agggcgtgga  1680
tatgtcctgc gggtaaatag ctgcgccgat ggtttctaca aagatcgtta tgtttatcgg  1740
cactttgcat cggccgcgct cccgattccg gaagtgcttg acattgggga attcagcgag  1800
agcctgacct attgcatctc ccgccgtgca caggtgtca cgttgcaaga cctgcctgaa  1860
accgaactgc ccgctgttct gcagccggtc gcggaggcca tggatgcgat cgctgcggcc  1920
gatcttagcc agacgagcgg gttcggccca ttcggaccgc aaggaatcgg tcaatacact  1980
acatggcgtg atttcatatg cgcgattgct gatccccatg tgtatcactg gcaaactgtg  2040
atggacgaca ccgtcagtgc gtccgtcgcg caggctctcg atgagctgat gctttgggcc  2100
gaggactgcc ccgaagtccg gcacctcgtg cacgcggatt tcggctccaa caatgtcctg  2160
acggacaatg gccgcataac agcggtcatt gactggagcg aggcgatgtt cggggattcc  2220
caatacgagg tcgccaacat cttcttctgg aggccggtggt tggcttgtat ggagcagcag  2280
acgcgctact cgagcggag gcatccgag cttgcaggat cgccgcggct ccgggcgtat  2340
```

-continued

```
atgctccgca ttggtcttga ccaactctat cagagcttgg ttgacggcaa tttcgatgat  2400
gcagcttggg cgcagggtcg atgcgacgca atcgtccgat ccggagccgg gactgtcggg  2460
cgtacacaaa tcgcccgcag aagcgcggcc gtctggaccg atggctgtgt agaagtactc  2520
gccgatagtg gaaaccgacg ccccagcact cgtccgaggg caaaggaata ggtttaactt  2580
gatactacta gatttttttct cttcatttat aaaattttttg gttataattg aagcttttaga  2640
agtatgaaaa aatcctttttt tttcattctt tgcaaccaaa ataagaagct tcttttattc  2700
attgaaatga tgaatataaa cctaacaaaa gaaaaagact cgaatatcaa acattaaaaa  2760
aaaataaaag aggttatctg tttttcccatt tagttggagt ttgcattttc taatagatag  2820
aactctcaat taatgtggat ttagtttctc tgttcgtttt tttttgtttt gttctcactg  2880
tatttacatt tctatttagt atttagttat tcatataatc ttaacttctc gagactcata  2940
actttagcat cacaaaatac gcaatataa cgagtagtaa cacttttata gttcatacat  3000
gcttcaacta cttaataaat gattgtatga taatgttttc aatgtaagag atttcgatta  3060
tccacaaact ttaaaacaca gggacaaaat tcttgatatc ctttcaaccg ctgcgttttg  3120
gatacctatt cttgacatga tatgactacc attttgttat tgtacgtggg gcagttgacg  3180
tcttatcata tgtcaaagtc atttgcgaag ttcttggcaa gttgccaact gacgagatgc  3240
agtaaaaaga gattgccgtc ttgaaacttt ttgtccttttt ttttttccgg ggactctacg  3300
agaacccttt gtcctactga ttaattttgt actgaatttg gacaattcag attttagtag  3360
acaagcgcga ggaggaaaag aaatgacaga aaaattccga tggacaagaa gataggaaaa  3420
aaaaaaagct ttcaccgatt tcctagaccg gaaaaaagtc gtatgacatc agaatgaaaa  3480
attttcaagt tagacaagga caaaatcagg acaaattgta aagatataat aaactatttg  3540
attcagcgcc aatttgcccct tttccatttt ccattaaatc tctgttctct cttacttata  3600
tgatgattag gtatcatctg tataaaactc ctttcttaat ttcactctaa agcataccc  3660
atagagaaga tctttcggtt cgaagacatt cctacgcata ataagaatag gagggaataa  3720
tgccagacaa tctatcatta catttaagcg gctcttcaaa aagattgaac tctcgccaac  3780
ttatggaatc ttccaatgag acctttgcgc caaataatgt ggatttggaa aaagagtata  3840
agtcatctca gagtaatata actaccgaag tttatgaggc atcgagcttt gaagtttaaa  3900
c                                                                 3901
```

| SEQ ID NO: 10 | moltype = DNA  length = 66 |
|---|---|
| FEATURE | Location/Qualifiers |
| misc_feature | 1..66 |
|  | note = Primer 50-56-pw100-G |
| source | 1..66 |
|  | mol_type = other DNA |
|  | organism = synthetic construct |

SEQUENCE: 10
```
gagtgaacct gctgcctggc gtgctctgac tcagtacatt tcatagtgga tggcggcgtt  60
agtatc                                                            66
```

| SEQ ID NO: 11 | moltype = DNA  length = 65 |
|---|---|
| FEATURE | Location/Qualifiers |
| misc_feature | 1..65 |
|  | note = Primer 50-56-pw101-G |
| source | 1..65 |
|  | mol_type = other DNA |
|  | organism = synthetic construct |

SEQUENCE: 11
```
cgtgtatacg ttttccgctt ctgctcttcg tcttttctct tcttccgata tcacaactgt  60
tacga                                                             65
```

| SEQ ID NO: 12 | moltype = DNA  length = 30 |
|---|---|
| FEATURE | Location/Qualifiers |
| misc_feature | 1..30 |
|  | note = Primer 61-67-CPK001-G |
| source | 1..30 |
|  | mol_type = other DNA |
|  | organism = synthetic construct |

SEQUENCE: 12
```
gtttaaacta ctattagctg aattgccact                                   30
```

| SEQ ID NO: 13 | moltype = DNA  length = 46 |
|---|---|
| FEATURE | Location/Qualifiers |
| misc_feature | 1..46 |
|  | note = Primer 61-67-CPK002-G |
| source | 1..46 |
|  | mol_type = other DNA |
|  | organism = synthetic construct |

SEQUENCE: 13
```
actgcaaagt acacatatat cccgggtgtc agctctttta gatcgg                 46
```

| SEQ ID NO: 14 | moltype = DNA  length = 46 |
|---|---|
| FEATURE | Location/Qualifiers |
| misc_feature | 1..46 |
|  | note = Primer 61-67-CPK003-G |
| source | 1..46 |
|  | mol_type = other DNA |
|  | organism = synthetic construct |

SEQUENCE: 14
```
ccgatctaaa agagctgaca cccgggatat atgtgtactt tgcagt                 46
```

```
SEQ ID NO: 15              moltype = DNA   length = 30
FEATURE                    Location/Qualifiers
misc_feature               1..30
                           note = Primer 61-67-CPK004-G
source                     1..30
                           mol_type = other DNA
                           organism = synthetic construct
SEQUENCE: 15
gtttaaacgg cgtcagtcca ccagctaaca                                          30

SEQ ID NO: 16              moltype = DNA   length = 30
FEATURE                    Location/Qualifiers
misc_feature               1..30
                           note = Primer 61-67-CPK005-G
source                     1..30
                           mol_type = other DNA
                           organism = synthetic construct
SEQUENCE: 16
gtttaaactt gctaaattcg agtgaaacac                                          30

SEQ ID NO: 17              moltype = DNA   length = 46
FEATURE                    Location/Qualifiers
misc_feature               1..46
                           note = Primer 61-67-CPK006-G
source                     1..46
                           mol_type = other DNA
                           organism = synthetic construct
SEQUENCE: 17
aaagatgaat tgaaaagctt cccgggtatg gaccctgaaa ccacag                        46

SEQ ID NO: 18              moltype = DNA   length = 46
FEATURE                    Location/Qualifiers
misc_feature               1..46
                           note = Primer 61-67-CPK007-
source                     1..46
                           mol_type = other DNA
                           organism = synthetic construct
SEQUENCE: 18
ctgtggtttc agggtccata cccgggaagc ttttcaattc atcttt                        46

SEQ ID NO: 19              moltype = DNA   length = 30
FEATURE                    Location/Qualifiers
misc_feature               1..30
                           note = Primer 61-67-CPK008-G
source                     1..30
                           mol_type = other DNA
                           organism = synthetic construct
SEQUENCE: 19
gtttaaaccc aacaataata atgtcagatc                                          30

SEQ ID NO: 20              moltype = DNA   length = 30
FEATURE                    Location/Qualifiers
misc_feature               1..30
                           note = Primer 61-67-CPK009-G
source                     1..30
                           mol_type = other DNA
                           organism = synthetic construct
SEQUENCE: 20
gtttaaacta ctcagtatat taagtttcga                                          30

SEQ ID NO: 21              moltype = DNA   length = 70
FEATURE                    Location/Qualifiers
misc_feature               1..70
                           note = Primer 61-67-CPK010-G
source                     1..70
                           mol_type = other DNA
                           organism = synthetic construct
SEQUENCE: 21
atctctcgca agagtcagac tgactcccgg gcgtgaataa gcttcgggtg acccttatgg         60
cattcttttt                                                                70

SEQ ID NO: 22              moltype = DNA   length = 70
FEATURE                    Location/Qualifiers
misc_feature               1..70
                           note = Primer 61-67-CPK011-G
source                     1..70
                           mol_type = other DNA
                           organism = synthetic construct
```

```
SEQUENCE: 22
aaaaagaatg ccataagggt cacccgaagc ttattcacgc ccgggagtca gtctgactct    60
tgcgagagat                                                           70

SEQ ID NO: 23          moltype = DNA  length = 30
FEATURE                Location/Qualifiers
misc_feature           1..30
                       note = Primer 61-67-CPK012-G
source                 1..30
                       mol_type = other DNA
                       organism = synthetic construct
SEQUENCE: 23
gtttaaacaa tttagtgtct gcgatgatga                                     30

SEQ ID NO: 24          moltype = DNA  length = 30
FEATURE                Location/Qualifiers
misc_feature           1..30
                       note = Primer 61-67-CPK013-G
source                 1..30
                       mol_type = other DNA
                       organism = synthetic construct
SEQUENCE: 24
gtttaaacta ttgtgagggt cagttatttc                                     30

SEQ ID NO: 25          moltype = DNA  length = 44
FEATURE                Location/Qualifiers
misc_feature           1..44
                       note = Primer 61-67-CPK014alt-G
source                 1..44
                       mol_type = other DNA
                       organism = synthetic construct
SEQUENCE: 25
gcggggacga ggcaagctaa actttagtat attcttcgaa gaaa                     44

SEQ ID NO: 26          moltype = DNA  length = 44
FEATURE                Location/Qualifiers
misc_feature           1..44
                       note = Primer 61-67-CPK015alt-G
source                 1..44
                       mol_type = other DNA
                       organism = synthetic construct
SEQUENCE: 26
tttcttcgaa gaatatacta agtttagct tgcctcgtcc ccgc                      44

SEQ ID NO: 27          moltype = DNA  length = 60
FEATURE                Location/Qualifiers
misc_feature           1..60
                       note = Primer 61-67-CPK016-G
source                 1..60
                       mol_type = other DNA
                       organism = synthetic construct
SEQUENCE: 27
caatcaacgt ggagggtaat tctgctagcc tctcccgggt ggatggcggc gttagtatcg    60

SEQ ID NO: 28          moltype = DNA  length = 60
FEATURE                Location/Qualifiers
misc_feature           1..60
                       note = Primer 61-67-CPK017-G
source                 1..60
                       mol_type = other DNA
                       organism = synthetic construct
SEQUENCE: 28
cgatactaac gccgccatcc acccgggaga ggctagcaga attaccctcc acgttgattg    60

SEQ ID NO: 29          moltype = DNA  length = 30
FEATURE                Location/Qualifiers
misc_feature           1..30
                       note = Primer 61-67-CPK018-G
source                 1..30
                       mol_type = other DNA
                       organism = synthetic construct
SEQUENCE: 29
gtttaaacgc cgccgttgtt gttattgtag                                     30

SEQ ID NO: 30          moltype = DNA  length = 30
FEATURE                Location/Qualifiers
misc_feature           1..30
                       note = Primer 61-67-CPK019-G
source                 1..30
```

```
                              mol_type = other DNA
                              organism = synthetic construct
SEQUENCE: 30
gtttaaactt ttccaatagg tggttagcaa                                    30

SEQ ID NO: 31             moltype = DNA   length = 55
FEATURE                   Location/Qualifiers
misc_feature              1..55
                          note = Primer 61-67-CPK020-G
source                    1..55
                          mol_type = other DNA
                          organism = synthetic construct
SEQUENCE: 31
gggtgacccg gcggggacga ggcaagctaa acgtcttcct ttctcttacc aaagt         55

SEQ ID NO: 32             moltype = DNA   length = 55
FEATURE                   Location/Qualifiers
misc_feature              1..55
                          note = Primer 61-67-CPK021-G
source                    1..55
                          mol_type = other DNA
                          organism = synthetic construct
SEQUENCE: 32
actttggtaa gagaaaggaa gacgtttagc ttgcctcgtc cccgccgggt caccc         55

SEQ ID NO: 33             moltype = DNA   length = 62
FEATURE                   Location/Qualifiers
misc_feature              1..62
                          note = Primer 61-67-CPK022-G
source                    1..62
                          mol_type = other DNA
                          organism = synthetic construct
SEQUENCE: 33
aatatcataa aaaaagagaa tctttcccgg gtggatggcg gcgttagtat cgaatcgaca    60
gc                                                                  62

SEQ ID NO: 34             moltype = DNA   length = 62
FEATURE                   Location/Qualifiers
misc_feature              1..62
                          note = Primer 61-67-CPK023-G
source                    1..62
                          mol_type = other DNA
                          organism = synthetic construct
SEQUENCE: 34
gctgtcgatt cgatactaac gccgccatcc acccgggaaa gattctcttt ttttatgata   60
tt                                                                  62

SEQ ID NO: 35             moltype = DNA   length = 45
FEATURE                   Location/Qualifiers
misc_feature              1..45
                          note = Primer 61-67-CPK024-G
source                    1..45
                          mol_type = other DNA
                          organism = synthetic construct
SEQUENCE: 35
gtttaaacgt gttaacgttt ctttcgccta cgtggaagga gaatc                    45

SEQ ID NO: 36             moltype = DNA   length = 35
FEATURE                   Location/Qualifiers
misc_feature              1..35
                          note = Primer 61-67-CPK025-G
source                    1..35
                          mol_type = other DNA
                          organism = synthetic construct
SEQUENCE: 36
tcccccggg ttaaaaaaaa tccttggact agtca                                35

SEQ ID NO: 37             moltype = DNA   length = 35
FEATURE                   Location/Qualifiers
misc_feature              1..35
                          note = Primer 61-67-CPK031-G
source                    1..35
                          mol_type = other DNA
                          organism = synthetic construct
SEQUENCE: 37
tcccccggg agttatgaca attacaacaa cagaa                                35

SEQ ID NO: 38             moltype = DNA   length = 30
FEATURE                   Location/Qualifiers
```

```
misc_feature          1..30
                      note = Primer 61-67-CPK032-G
source                1..30
                      mol_type = other DNA
                      organism = synthetic construct
SEQUENCE: 38
tcccccccggg tatatatata tcattgttat                                        30

SEQ ID NO: 39         moltype = DNA   length = 30
FEATURE               Location/Qualifiers
misc_feature          1..30
                      note = Primer 61-67-CPK035-G
source                1..30
                      mol_type = other DNA
                      organism = synthetic construct
SEQUENCE: 39
tcccccccggg aaaagtaagt caaaaggcac                                        30

SEQ ID NO: 40         moltype = DNA   length = 30
FEATURE               Location/Qualifiers
misc_feature          1..30
                      note = Primer 61-67-CPK040-G
source                1..30
                      mol_type = other DNA
                      organism = synthetic construct
SEQUENCE: 40
tcccccccggg atggtctgct taaatttcat                                        30

SEQ ID NO: 41         moltype = DNA   length = 45
FEATURE               Location/Qualifiers
misc_feature          1..45
                      note = Primer 61-67-CPK041-G
source                1..45
                      mol_type = other DNA
                      organism = synthetic construct
SEQUENCE: 41
tcccccccggg tagcttgtac ccattaaaag aattttatca tgccg                       45

SEQ ID NO: 42         moltype = DNA   length = 30
FEATURE               Location/Qualifiers
misc_feature          1..30
                      note = Primer 61-67-CPK046-G
source                1..30
                      mol_type = other DNA
                      organism = synthetic construct
SEQUENCE: 42
tcccccccggg tttctcattc aagtggtaac                                        30

SEQ ID NO: 43         moltype = DNA   length = 30
FEATURE               Location/Qualifiers
misc_feature          1..30
                      note = Primer 61-67-CPK047-G
source                1..30
                      mol_type = other DNA
                      organism = synthetic construct
SEQUENCE: 43
tcccccccggg taaataaaga aaataaagtt                                        30

SEQ ID NO: 44         moltype = DNA   length = 47
FEATURE               Location/Qualifiers
misc_feature          1..47
                      note = Primer 61-67-CPK050-G
source                1..47
                      mol_type = other DNA
                      organism = synthetic construct
SEQUENCE: 44
aatttttgaa aattcaatat aaatggcttc agaaaaagaa attagga                      47

SEQ ID NO: 45         moltype = DNA   length = 47
FEATURE               Location/Qualifiers
misc_feature          1..47
                      note = Primer 61-67-CPK051-G
source                1..47
                      mol_type = other DNA
                      organism = synthetic construct
SEQUENCE: 45
tcctaatttc tttttctgaa gccatttata ttgaattttc aaaaatt                      47

SEQ ID NO: 46         moltype = DNA   length = 51
```

```
FEATURE                 Location/Qualifiers
misc_feature            1..51
                        note = Primer 61-67-CPK052-G
source                  1..51
                        mol_type = other DNA
                        organism = synthetic construct
SEQUENCE: 46
agttttcacc aattggtctg cagccattat agttttttct ccttgacgtt a            51

SEQ ID NO: 47           moltype = DNA  length = 51
FEATURE                 Location/Qualifiers
misc_feature            1..51
                        note = Primer 61-67-CPK053-G
source                  1..51
                        mol_type = other DNA
                        organism = synthetic construct
SEQUENCE: 47
taacgtcaag gagaaaaaac tataatggct gcagaccaat tggtgaaaac t            51

SEQ ID NO: 48           moltype = DNA  length = 47
FEATURE                 Location/Qualifiers
misc_feature            1..47
                        note = Primer 61-67-CPK054-G
source                  1..47
                        mol_type = other DNA
                        organism = synthetic construct
SEQUENCE: 48
aattttgaa aattcaatat aaatgaaact ctcaactaaa ctttgtt                  47

SEQ ID NO: 49           moltype = DNA  length = 47
FEATURE                 Location/Qualifiers
misc_feature            1..47
                        note = Primer 61-67-CPK055-G
source                  1..47
                        mol_type = other DNA
                        organism = synthetic construct
SEQUENCE: 49
aacaaagttt agttgagagt ttcatttata ttgaattttc aaaaatt                 47

SEQ ID NO: 50           moltype = DNA  length = 47
FEATURE                 Location/Qualifiers
misc_feature            1..47
                        note = Primer 61-67-CPK056-G
source                  1..47
                        mol_type = other DNA
                        organism = synthetic construct
SEQUENCE: 50
aattttgaa aattcaatat aaatgtctca gaacgtttac attgtat                  47

SEQ ID NO: 51           moltype = DNA  length = 47
FEATURE                 Location/Qualifiers
misc_feature            1..47
                        note = Primer 61-67-CPK057-G
source                  1..47
                        mol_type = other DNA
                        organism = synthetic construct
SEQUENCE: 51
atacaatgta aacgttctga gacatttata ttgaattttc aaaaatt                 47

SEQ ID NO: 52           moltype = DNA  length = 51
FEATURE                 Location/Qualifiers
misc_feature            1..51
                        note = Primer 61-67-CPK058-G
source                  1..51
                        mol_type = other DNA
                        organism = synthetic construct
SEQUENCE: 52
tgcagaagtt aagaacggta atgacattat agttttttct ccttgacgtt a            51

SEQ ID NO: 53           moltype = DNA  length = 51
FEATURE                 Location/Qualifiers
misc_feature            1..51
                        note = Primer 61-67-CPK059-G
source                  1..51
                        mol_type = other DNA
                        organism = synthetic construct
SEQUENCE: 53
taacgtcaag gagaaaaaac tataatgtca ttaccgttct taacttctgc a            51
```

| SEQ ID NO: 54 | moltype = DNA   length = 47 |
| --- | --- |
| FEATURE | Location/Qualifiers |
| misc_feature | 1..47 |
| | note = Primer 61-67-CPK060-G |
| source | 1..47 |
| | mol_type = other DNA |
| | organism = synthetic construct |

SEQUENCE: 54
aattttgaa aattcaatat aaatgtcaga gttgagagcc ttcagtg          47

| SEQ ID NO: 55 | moltype = DNA   length = 47 |
| --- | --- |
| FEATURE | Location/Qualifiers |
| misc_feature | 1..47 |
| | note = Primer 61-67-CPK061-G |
| source | 1..47 |
| | mol_type = other DNA |
| | organism = synthetic construct |

SEQUENCE: 55
cactgaaggc tctcaactct gacatttata ttgaattttc aaaaatt         47

| SEQ ID NO: 56 | moltype = DNA   length = 51 |
| --- | --- |
| FEATURE | Location/Qualifiers |
| misc_feature | 1..51 |
| | note = Primer 61-67-CPK062-G |
| source | 1..51 |
| | mol_type = other DNA |
| | organism = synthetic construct |

SEQUENCE: 56
ggtaacggat gctgtgtaaa cggtcattat agttttttct ccttgacgtt a    51

| SEQ ID NO: 57 | moltype = DNA   length = 51 |
| --- | --- |
| FEATURE | Location/Qualifiers |
| misc_feature | 1..51 |
| | note = Primer 61-67-CPK063-G |
| source | 1..51 |
| | mol_type = other DNA |
| | organism = synthetic construct |

SEQUENCE: 57
taacgtcaag gagaaaaaac tataatgacc gtttacacag catccgttac c    51

| SEQ ID NO: 58 | moltype = DNA   length = 47 |
| --- | --- |
| FEATURE | Location/Qualifiers |
| misc_feature | 1..47 |
| | note = Primer 61-67-CPK064-G |
| source | 1..47 |
| | mol_type = other DNA |
| | organism = synthetic construct |

SEQUENCE: 58
aattttgaa aattcaatat aaatgactgc cgacaacaat agtatgc          47

| SEQ ID NO: 59 | moltype = DNA   length = 47 |
| --- | --- |
| FEATURE | Location/Qualifiers |
| misc_feature | 1..47 |
| | note = Primer 61-67-CPK065-G |
| source | 1..47 |
| | mol_type = other DNA |
| | organism = synthetic construct |

SEQUENCE: 59
gcatactatt gttgtcggca gtcatttata ttgaattttc aaaaatt         47

| SEQ ID NO: 60 | moltype = DNA   length = 70 |
| --- | --- |
| FEATURE | Location/Qualifiers |
| misc_feature | 1..70 |
| | note = Primer 61-67-CPK066-G |
| source | 1..70 |
| | mol_type = other DNA |
| | organism = synthetic construct |

SEQUENCE: 60
ggtaagacgg ttgggtttta tcttttgcag ttggtactat taagaacaat cacaggaaac    60
agctatgacc                                                           70

| SEQ ID NO: 61 | moltype = DNA   length = 70 |
| --- | --- |
| FEATURE | Location/Qualifiers |
| misc_feature | 1..70 |
| | note = Primer 61-67-CPK067-G |
| source | 1..70 |
| | mol_type = other DNA |
| | organism = synthetic construct |

SEQUENCE: 61

```
ttgcgttttg tactttggtt cgctcaattt tgcaggtaga taatcgaaaa gttgtaaaac    60
gacggccagt                                                            70

SEQ ID NO: 62           moltype = DNA   length = 44
FEATURE                 Location/Qualifiers
misc_feature            1..44
                        note = Primer 91-014-CPK231-G
source                  1..44
                        mol_type = other DNA
                        organism = synthetic construct
SEQUENCE: 62
ttgtgatgct aaagttatga gtctcgagaa gttaagatta tatg                      44

SEQ ID NO: 63           moltype = DNA   length = 44
FEATURE                 Location/Qualifiers
misc_feature            1..44
                        note = Primer 91-014-CPK232-G
source                  1..44
                        mol_type = other DNA
                        organism = synthetic construct
SEQUENCE: 63
catataatct taacttctcg agactcataa ctttagcatc acaa                      44

SEQ ID NO: 64           moltype = DNA   length = 28
FEATURE                 Location/Qualifiers
misc_feature            1..28
                        note = Primer 91-014-CPK233-G
source                  1..28
                        mol_type = other DNA
                        organism = synthetic construct
SEQUENCE: 64
gtttaaactt caaagctcga tgcctcat                                        28

SEQ ID NO: 65           moltype = DNA   length = 28
FEATURE                 Location/Qualifiers
misc_feature            1..28
                        note = Primer 91-014-CPK236-G
source                  1..28
                        mol_type = other DNA
                        organism = synthetic construct
SEQUENCE: 65
gtttaaacga ggctcaccta acaattca                                        28

SEQ ID NO: 66           moltype = DNA   length = 44
FEATURE                 Location/Qualifiers
misc_feature            1..44
                        note = Primer 91-014-CPK237-G
source                  1..44
                        mol_type = other DNA
                        organism = synthetic construct
SEQUENCE: 66
gatgtgtatt actagtgtcg acactgctga agaatttgat tttt                      44

SEQ ID NO: 67           moltype = DNA   length = 44
FEATURE                 Location/Qualifiers
misc_feature            1..44
                        note = Primer 91-014-CPK238-G
source                  1..44
                        mol_type = other DNA
                        organism = synthetic construct
SEQUENCE: 67
aaaaatcaaa ttcttcagca gtgtcgacac tagtaataca catc                      44

SEQ ID NO: 68           moltype = DNA   length = 1761
FEATURE                 Location/Qualifiers
misc_feature            1..1761
                        note = DNA fragment GAL11 to 48-NatR- GAL11500 to 1550
source                  1..1761
                        mol_type = other DNA
                        organism = synthetic construct
SEQUENCE: 68
atgactaaat ctcattcaga agaagtgatt gtacctgagt tcaattctca caggaaacag     60
ctatgaccat gattacgcca agcttggtac cgagctcgga tccactagta acggccgcca   120
gtgtgctgga attcgccctt gtcgacacta gtaatacaca tcatcgtcct acaagttcat   180
caaagtgttg acagacaac tataccagca tggatctctt gtatcggttc ttttctcccg   240
ctctctcgca ataacaatga acactgggtc aatcatagcc tacacaggtg aacagagtag   300
cgtttataca gggtttatac ggtgattcct acggcaaaaa ttttttcattt ctaaaaaaaa   360
aaagaaaaat ttttctttcc aacgctagaa ggaaagaaa atctaatta aattgatttg     420
gtgattttct gagagttccc ttttttcatat atcgaatttt gaatataaaa ggagatcgaa   480
```

-continued

```
aaaatttttc tattcaatct gttttctggt tttatttgat agttttttg tgtattatta      540
ttatggatta gtactggttt atatgggttt tctgtataa cttcttttta ttttagtttg      600
tttaatctta ttttgagtta cattatagtt ccctaactgc aagagaagta acattaaaaa    660
tgaccactct tgacgacacg gcttaccggt accgcaccag tgtcccgggg gacgccgagg    720
ccatcgaggc actggatggg tccttcacca ccgacacgt cttccgcgtc accgccaccg    780
gggacggctt caccctgcgg gaggtgccgg tggacccgcc cctgaccaag gtgttccccg    840
acgacgaatc ggacgacgaa tcggacgccg gggaggacgg cgaccccggac tcccggacgt    900
tcgtcgcgta cggggacgac ggcgacctgg cgggcttcgt ggtcgtctcg tactccggct    960
ggaaccgccg gctgaccgtc gaggacatcg aggtcgcccc ggagcaggcgg gggcacgggg    1020
tcgggcgcgc gttgatgggg ctcgcgacgg agttcgcccg cgagcgggggc gccgggcacc    1080
tctggctgga ggtcaccaac gtcaacgcac cggcgatcca cgcgtaccgg cggatggggt    1140
tcaccctctg cggcctggac accgcccgtg acgacggcac cgcctcggac ggcgagcagg    1200
cgctctacat gagcatgccc tgcccctgag tttaacttga tactactaga ttttttctct    1260
tcatttataa aattttggt tataattgaa gcttagaag tatgaaaaaa tccttttt      1320
tcattctttg caaccaaaat aagaagcttc ttttattcat tgaaatgatg aatataaacc    1380
taacaaaaga aaaagactcg aatatcaaac attaaaaaa aataaaagag gttatctgtt    1440
ttcccattta gttggagttt gcattttcta atagataga ctctcaatta atgtggattt    1500
agtttctctg ttcgttttt tttgtttttgt tctcactgta tttacattc tatttagtat    1560
ttagttattc atataatctt aacttctcga ggagctcaag ggcaattctg cagatatcca    1620
tcacactggc ggccgctcga gcatgcatct agagggccca attcgcccta tagtgagtcg    1680
tattacaatt cactggccgt cgttttacaa caagtaccct aagatcactg atgctgagct    1740
agaaaatgct atcatcgtct c                                              1761
```

```
SEQ ID NO: 69            moltype = DNA   length = 7348
FEATURE                  Location/Qualifiers
misc_feature             1..7348
                         note = Vector pAM178
source                   1..7348
                         mol_type = other DNA
                         organism = synthetic construct
SEQUENCE: 69
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120
ttggcggggt tcggggctgg cttaactatg cggcatcaga gcagattgta ctgagagtgc    180
accatatcga ctacgtcgta aggccgtttc tgacacagta aaattcttga gggaactttc    240
accattatgg gaaatgcttc aagaaggtat tgacttaaac tccatcaaat ggtcaggtca    300
ttgagtgttt tttatttgtt gtatttttt tttttagag aaaatcctcc aatatcaaat    360
taggaatcgt agtttcatga ttttctgtta caccttaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
agattgcgta tatagtttcg tctacccta gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaacctttt aactgcatct    780
tcaatggcct taccttcttc aggcaagttc aatgacaatt tcaacatcat tgcagcagac    840
aagatagtgg cgatagggtc aacccttatc tttggcaaat ctggagcaga accgtggcat    900
ggttcgtaca aaccaaatgc ggtgttcttg tctggcaaga accagagtgc cagcagatggc    960
aacaaaccca aggaacctgg gataacggag gcttcatcgg agatgatatc accaaacatg    1020
ttgctggtga ttataatacc atttaggtgg gttgggttct taactaggat catggcggca    1080
gaatcaatca attgatgttg aaccttcaat gtagggaatt cgttcttgat ggtttcctcc    1140
acagttttc tccataatct tgaagaggc aaaagattg ctttatccaa ggacccaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttctttacgg atttttagta aaccttgttc aggtctaaca    1500
ctaccggtac cccatttagg accagccaca gcacctaaca aaacggcatc aaccttcttg    1560
gaggcttcca gcgcctcatc tggaagtgga cacctgtag catcgatagc agcaccacca    1620
attaaatgat tttgaaatc gaacttgaca ttggaacgaa catcagaaat agctttaaga    1680
accttaatgg cttcggctgt gatttcttga ccaacgtggt cacctggcaa aacgacgatc    1740
ttcttagggg cagacattac aatggtatat ccttgaaata tatataaaa aaggcgcctt    1800
agaccgctcg gccaaacaac caattacttg ttgagaaata gagtataatt atcctataaa    1860
tataacgttt ttgaacacac atgaacaagg aagtacagga caattgattt tgaagagaat    1920
gtggattttg atgtaattgt tgggattcca ttttaataa ggcaataata ttaggtatgt    1980
ggatatacta gaagttctcc tcgaccgtcg atatgcggtg tgaaataccg cacagatgcg    2040
taaggagaaa ataccgcatc aggaaattgt aaacgttaat attttgttaa aattcgcgtt    2100
aaatttttgt taaatcagct catttttaa ccaataggcc gaaatcggca aaatccctta    2160
taaatcaaaa gaatagaccg agatagggtt gagtgttgtt ccagtttgga acaagagtcc    2220
actattaaag aacgtggact ccaacgtcaa agggcgaaaa accgtctatc agggcgatgg    2280
cccactacgt gaaccatcac cctaatcaag ttttttgggg tcgaggtgcc gtaaagcact    2340
aaatcggaac cctaaaggga gcccccgatt tagagcttga cggggaaagc cggcgaacgt    2400
ggcgagaaag gaagggaaga agcgaaagg agcgggcgct agggcgctgg caagtgtagc    2460
ggtcacgctg cgcgtaacca ccacccgc cgcgcttaat gcgccgctac agggcgcgtc    2520
gcgccattcg ccattcaggc tgcgcaactg ttgggaagg cgatcggtgc gggcctcttc    2580
gctattacgc cagctgaatt ggagcgacct catgctatac ctgagaaagc aacctgacct    2640
acaggaaaga gttactcaag aataagaatt tcgttttaa aacctaagag tcactttaaa    2700
atttgtatac acttattttt tttataactt atttaataat aaaaatcata atcataaga    2760
aattcgctta tttagaagtg tcaacaacgt atctaccaac gatttgaccc ttttccatct    2820
tttcgtaaat ttctggcaag gtagacaagc cgacaaccct gattggagac ttgaccaaac    2880
```

```
ctctggcgaa gaattgttaa ttaagagctc agatcttatc gtcgtcatcc ttgtaatcca   2940
tcgatactag tgcggccgcc ctttagtgag ggttgaattc gaattttcaa aaattcttac   3000
ttttttttg  gatggacgca aagaagttta ataatcatat tacatggcat taccaccata   3060
tacatatcca tatacatatc catatctaat cttacttata tgttgtggaa atgtaaagag   3120
ccccattatc ttagcctaaa aaaaccttct ctttggaact ttcagtaata cgcttaactg   3180
ctcattgcta tattgaagta cggattagaa gccgccgagc gggtgacagc cctccgaagg   3240
aagactctcc tccgtgcgtc ctcgtcttca ccggtcgcgt tcctgaaacg cagatgtgcc   3300
tcgcgccgca ctgctccgaa caataaagat tctacaatac tagcttttat ggttatgaag   3360
aggaaaaatt ggcagtaacc tggcccccaca aaccttcaaa tgaacgaatc aaattaacaa   3420
ccataggatg ataatgcgat tagttttta  gccttatttc tggggtaatt aatcagcgaa   3480
gcgatgattt tgatctatt  aacagatata taaatgcaaa aactgcataa ccactttaac   3540
taatactttc aacattttcg gtttgtatta cttcttattc aaatgtaata aaagtatcaa   3600
caaaaaattg ttaatatacc tctatctttt aacgtcaagg agaaaaaacc ccggatccgt   3660
aatacgactc actatagggc ccgggcgtcg acatggcaga aagttgatt  tccgaagaag   3720
acctcgagta agcttggtac cgcggctagc taagatccgc tctaaccgaa aaggaaggag   3780
ttagacaacc tgaagtctag gtccctattt atttttttat agttatgtta gtattaagaa   3840
cgttatttat atttcaaatt tttctttttt ttctgtacag acgcgtgtac gcatgtaaca   3900
ttatactgaa aaccttgctt gagaaggttt tgggacgctc gaagatccag ctgcattaat   3960
gaatcggcca acgcgcgggg agaggcggtt tgcgtattgg gcgctcttcc gcttcctcgc   4020
tcactgactc gctgcgctcg tcgttcggc  tgcggcgagc ggtatcagct cactcaaagg   4080
cggtaatacg gttatccaca gaatcagggg ataacgcagg aaagaacatg tgagcaaaag   4140
gccagcaaaa ggccaggaac cgtaaaaagg ccgcgttgct ggcgtttttc cataggctcc   4200
gcccccctga cgagcatcac aaaaatcgac gctcaagtca gaggtggcga aacccgacag   4260
gactataaag ataccaggcg tttccccctg gaagctccct cgtgcgctct cctgttccga   4320
ccctgccgct taccggatac ctgtccgcct ttctcccttc gggaagcgtg gcgctttctc   4380
atagctcacg ctgtaggtat ctcagttcgg tgtaggtcgt tcgctccaag ctgggctgtg   4440
tgcacgaacc ccccgttcag cccgaccgct gcgccttatc cggtaactat cgtcttgagt   4500
ccaacccggt aagacacgac ttatcgccac tggcagcagc cactggtaac aggattagca   4560
gagcgaggta tgtaggcggt gctacagagt tcttgaagtg gtggcctaac tacggctaca   4620
ctagaaggac agtatttggt atctgcgctc tgctgaagcc agttaccttc ggaaaaagag   4680
ttggtagctc ttgatccggc aaacaaacca ccgctggtag cggtggtttt tttgtttgca   4740
agcagcagat tacgcgcaga aaaaaaggat ctcaagaaga tcctttgatc ttttctacgg   4800
ggtctgacgc tcagtggaac gaaaactcac gttaagggat tttggtcatg agattatcaa   4860
aaaggatctt cacctagatc cttttaaatt aaaaatgaag ttttaaatca atctaaagta   4920
tatatgagta aacttggtct gacagttacc aatgcttaat cagtgaggca cctatctcag   4980
cgatctgtct atttcgttca tccatagttg cctgactccc cgtcgtgtag ataactacga   5040
tacgggaggg cttaccatct ggccccagtg ctgcaatgat accgcgagac ccacgctcac   5100
cggctccaga tttatcagca ataaaccagc cagccggaag ggccgagcgc agaagtggtc   5160
ctgcaacttt atccgcctcc atccagtcta ttaattgttg ccgggaagct agagtaagta   5220
gttcgccagt taatagtttg cgcaacgttg ttgccattgc tacaggcatc gtggtgtcac   5280
gctcgtcgtt tggtatggct tcattcagct ccggttccca acgatcaagg cgagttacat   5340
gatccccat  gttgtgcaaa aaagcggtta gctccttcgg tcctccgatc gttgtcagaa   5400
gtaagttggc cgcagtgtta tcactcatgg ttatggcagc actgcataat tctcttactg   5460
tcatgccatc cgtaagatgc ttttctgtga ctggtgagta ctcaaccaag tcattctgag   5520
aatagtgtat gcggcgaccg agttgctctt gcccggcgtc aatacgggat aataccgcgc   5580
cacatagcag aactttaaaa gtgctcatca ttggaaaacg ttcttcgggg cgaaaactct   5640
caaggatctt accgctgttg agatccagtt cgatgtaacc cactcgtgca cccaactgat   5700
cttcagcatc ttttactttc accagcgttt ctgggtgagc aaaaacagga agcaaaatg   5760
ccgcaaaaaa gggaataagg gcgacacgga aatgttgaat actcatactc ttcctttttc   5820
aatattattg aagcatttat cagggttatt gtctcatgag cggatacata tttgaatgta   5880
tttagaaaaa taaacaaata gggttccgc  gcacatttcc ccgaaaagtg ccacctgaac   5940
gaagcatctg tgcttcattt tgtagaacaa aaatgcaacg cgagagcgct aattttcaa   6000
acaaagaatc tgagctgcat tttacagaa  cagaaatgca acgcgaaagc gctattttac   6060
caacgaagaa tctgtgcttc attttgtaa  aacaaaaatg caacgcgaga gcgctaattt   6120
ttcaaacaaa gaatctgagc tgcatttta  cagaacagaa atgcaacgcg agagcgctat   6180
tttaccaaca aagaatctat acttcttttt tgttctacaa aaatgcatcc cgagagcgct   6240
attttctaa  caaagcatct tagattactt ttttctcct  ttgtgcgctc tataatgcag   6300
tctcttgata acttttgca  ctgtaggtcc gttaaggtta gaagaggct  actttggtgt   6360
ctattttctc ttccataaaa aaagcctgac tccacttccc gcgttactg  attactagcg   6420
aagctgcggg tgcatttttt caagataaag gcatcccga  ttatattcta taccgatgtg   6480
gattgcgcat actttgtgaa cagaaagtga tagcgttgat gattcttcat tggtcagaaa   6540
attatgaacg gtttcttcta ttttgtctct atatactacg tataggaaat gtttacattt   6600
tcgtattgtt ttcgattcac tctatgaata gttcttacta caatttttt  gtctaaagag   6660
taatactaga gataaacata aaaaatgtag aggtcgagtt tagatgcaag ttcaaggagc   6720
gaaaggtgga tgggtaggtt atataggat  atagcacaga gatatatagc aaagagatac   6780
ttttgagcaa tgtttgtgga agcggtattc gcaatatttt agtagctcgt tacagtccgg   6840
tgcgtttttg gttttttgaa agtgcgtctt cagagcgctt ttggttttca aaagcgctct   6900
gaagttccta tactttctag agaataggaa cttcggaata ggaacttcaa agcgtttccg   6960
aaaacgagcg cttccgaaaa tgcaacgcga gctgcgcaca tacagctcac tgttcacgtc   7020
gcacctatat ctgcgtgttg cctgtatata tatatacatg agaagaacgg catagtgcgt   7080
gtttatgctt aaatgcgtac ttatatgcgt ctatttatgt aggatgaaag gtagtctagt   7140
acctcctgtg atattatccc attccatgcg gggtatcgta tgcttccttc agcactaccc   7200
tttagctgtt ctatatgctg ccactcctca attggattag tctcatcctt caatgctatc   7260
atttcctttg atattggatc atactaagaa accattatta tcatgacatt aacctataaa   7320
aataggcgta tcacgaggcc ctttcgtc                                      7348
```

SEQ ID NO: 70          moltype = DNA   length = 4883
FEATURE                Location/Qualifiers
misc_feature           1..4883

```
                  note = T7-FS-FRT-Kan-FRT cassette
source            1..4883
                  mol_type = other DNA
                  organism = synthetic construct
SEQUENCE: 70
gctgggcgat ctgttgcgcg aagtggtatg gccgacagat gtgtccacgc tggatgttga   60
tgcaatggtg gtacgcgaaa ccactcaccg tttcagccgc ttatcctttc accgggcaat  120
ggtcgggcga cgtttgccgc ttctgaaaac cgcctcgggc ctgacctggc tggccttttg  180
cccggaacaa gaccgcaagg aattaatcga aatgttagcc tcccgccccg gtgatgacta  240
tcaactggca cgggaaccgt taaagctgga agccattctg gcgcgcgcgc gcaaagaggg  300
ttacggacag aactaccgcg gctgggatca ggaggagaag atcgcctcta tcgccgtacc  360
gctgcgcagt gaacaacggg tgattggctg tctgaatctg gtgtatatgg cgagcgcaat  420
gaccattgaa caggcagcgg aaaagcatct tccggcgcta caacgggtag caaaacagat  480
cgaagaaggg gttgaatcgc aggctattct ggtggccgga aggcgaagcg gcatgcaagg  540
agatggcgcc caacagtccc ccggccacgg ggcctgccac catacccacg ccgaaacaag  600
cgctcatgag cccgaagtgg cgagcccgat cttccccatc ggtgatgtcg gcgatatagg  660
cgccagcaac cgcacctgtg gcgccggtga tgccggccac gatgcgtccg gcgtagagga  720
tcgagatctc gatcccgcga aattaatacg actcactata gggaattgt gagcggataa  780
caattcccct ctagaaataa ttttgtttaa ctttaagaag gagatatacc atggacactc  840
tgccgatctc ttccgtaagc ttttcttcct ctacttcccc gctggtagtc gatgacaagg  900
tttctaccaa acctgatgta attcgtcaca ctatgaactt caacgcatct atctgggggcg  960
atcagttcct gacttatgat gaaccggaag atctggtaat gaaaaagcaa ctggtagaag 1020
aactgaaaga agaagttaaa aaggaactga tcaccattaa gggtagcaac gaaccgatgc 1080
agcacgtgaa actgattgaa ctgatcgatg cggttcagcg tctgggtatt gcttatcatt 1140
ttgaagagga atcgaggaa gctctgcaac acatccacgt aacctacggc gaacaatggg 1200
tggataaaga gaatctgcag tctatcagcc tgtggttccg cctgctgcgt cagcaaggtt 1260
tcaatgtctc ttctggcgtt ttcaaagact tcatggatga aaagggcaaa ttcaaggaat 1320
ccctgtgtaa cgatgcgcaa ggtatcctgg cactgtacga agcggccttc atgcgtgtgg 1380
aagacgaaac cattctggac aacgcgctgg aattcactaa agtgcatctg gacatcatcg 1440
cgaaagatcc gtcctgcgac tcctctctgc gtactcagat ccatcaagcg ctgaaacagc 1500
cgctgcgtcg tcgcctggca cgtattgagg ctctgcacta tgccgatt taccagcagg 1560
aaacctctca cgacgaagtc ctgctgaaac tggctaaact ggacttcagc gttctgcaat 1620
ctatgcacaa gaaagaactg tcccacatct gcaaatggtg gaaagatctg gatctgcaaa 1680
acaaactgcc gtacgttcgt gaccgtgttg ttgagggcta ttttttggatt ctgtccatct 1740
actatgaacc acagcacgcg cgtactcgca tgtttctgat gaaaacctgc atgtggctga 1800
ttgtcctgga cgacacctt gacaactatg gtacgtacga agaactggaa atcttcaccc 1860
aggccgtgga acgttggtct atttcctgcc tggatatgct gccggaatac atgaaactga 1920
tctatcaaga actggttaac ctgcacgtgg aaatggaaga gtctctggag aaagaaggta 1980
aaacttacca gatccactac gtcaaggaga tggcgaaaga actggtccgt aactatctgg 2040
tcgaggcgcg ttggctgaaa gagggctata tgccgactct ggaagaatac atgagcgtat 2100
ccatggttac cggcacctac ggcctgatga ttgcgcgttc ctacgtcggc cgtggtgata 2160
ttgttaccga agatacctt aagtgggttt cttcctaccc gccgatcatc aaagcgtctt 2220
gtgtcatcgt tcgcctgatg gacgacatcg tttctcacaa agaggagcaa gaacgtggtc 2280
acgtagcatc tagcatcgaa tgctactcca agaatccgg cgcgtccgaa gaagaagctt 2340
gcgaatacat cagccgtaaa gttgaagatg cctggaaagt tatcaaccgc gaaagcctgc 2400
gtccgacggc ggtcccgttt ccgctgctga tgccggcaat caacctggca cgcatgtgtg 2460
aggttctgta cagcgtgaac gatggttta ctcacgcgga aggtgacatg aagagctata 2520
tgaagagctt cttcgtacac cctatgctcg tatgagagct cggtacccaa actctatgac 2580
tgagttaatt aagcagttca tacaggtgcgcg ccgtctgata aaacagaatt tgcctggcgg 2640
cagtagcgcg gtggtcccac ctgacccat gccgaactca gaagtgaaac gccgtagcgc 2700
cgatggtagt gtggggtctc cccatgcgag agtagggaac tgccaggcat caaataaaac 2760
gaaaggctca gtcgaaagac tgggccttc gttttatctg ttgtttgtcg gtgaacgctc 2820
tcctgagtag gacaaatccg ccggggagcgg atttgaacgt tgcgaagcaa cggcccggag 2880
ggtggcgggc aggacgcccg ccataaactg ccaggcatca aattaagcag aaggccatcc 2940
tgaccgatgg ccttttttgcg tttctacaaa ctctttctag agctgcctcg cgcgtttcgg 3000
tgatgacggt cctctgaccg gttggacgtt aaaaaatatc cccggcaact gacacgtac 3060
cggggatttt tttatcattc tgagcttgtc tgtaagcgga tgccgggagc agacaagccc 3120
gtgaagttcc tattctctag aaagtatagg aacttcagag cgctttgacg tcggaattgc 3180
cagctggggc gccctctggt aaggttggga gccctgcaa agtaaactgg atggctttct 3240
tgccgccaag gatctgatgg cgcagggat caagatctca tcaagagaca ggatgaggat 3300
cgtttcgcat gattgaacaa gatggattgc acgcaggttc tccggccgct tgggtggaga 3360
ggctattcgg ctatgactgg gcacaacaga atcggctg ctctgatgcc gccgtgttcc 3420
ggctgtcagc gcaggggcgc ccggttcttt ttgtcaagac cgacctgtcc ggtgccctga 3480
atgaactgca ggacgaggca gcgcggctat cgtggctggc cacgacgggc gttccttgcg 3540
cagctgtgct cgacgttgtc actgaagcgg gaagggactg gctgctattg gcgaagtgc 3600
cggggcagga tctcctgtca tctcaccttg ctcctgccga aaagtatcc atcatggctg 3660
atgcaatgcg gcggctgcat acgcttgatc cggctacctg cccattcgac caccaagcga 3720
aacatcgcat cgagcgagca cgtactcgga tggaagccgg tcttgtcgat caggatgatc 3780
tggacgaaga gcatcagggg ctcgcgccag ccgaactgtt cgccaggctc aaggcgcgca 3840
tgcccgacgg cgaggatctc gtcgtgaccc atggcgatgc ctgcttgccg aatatcatgg 3900
tggaaaatgg ccgcttttct ggattcatcg actgtggccg ctgggtgtg gcgaccgct 3960
atcaggacat agcgttggct acccgtgata ttgctgaaga gcttggcggc gaatgggctg 4020
accgcttcct cgtgctttac ggtatcgccg ctcccgattc gcagcgcatc gccttctatc 4080
gccttcttga cgagttcttc tgagcgggac tctggggttc gaaatgaccg accaagcgac 4140
gcccaacctg ccatcacctg tcgatgctct tcgctccttg caagctcgcc gcttatcaca 4200
ccgccgggcg tttttttattg gtgagaatcc aagcactagt aagggggatc ttgaagttcc 4260
tattccgaag ttcctattct ctagaaagta taggaacttc acatgcagct cccggagacg 4320
gtcacgcgat cgcattataa aaattgcctg atacgctgcg cttatcaggc ctacaagttc 4380
agcgatctac attagccgca tccggcatga acaaagcgca ggaacaagcg tcgcatcatg 4440
```

```
cctctttgac ccacagctgc ggaaaacgta ctggtgcaaa acgcagggtt atgatcatca    4500
gcccaacgac gcacagcgca tgaaatgccc agtccatcag gtaattgccg ctgatactac    4560
gcagcacgcc agaaaaccac ggggcaagcc cggcgatgat aaaaccgatt ccctgcataa    4620
acgccaccga cttgccagca atagccggtt gcacagagtg atcgagcgcc agcagcaaac    4680
agagcggaaa cgccgccgcc agacctaacc cacacaccat cgcccacaat accggcaatt    4740
gcatcggcag ccagataaag ccgcagaacc ccaccagttg taacaccagc gccagcatta    4800
acagtttgcg ccgatcctga tggcgagcca tagcaggcat cagcaaagct cctgcggctt    4860
gcccaagcgt catcaatgcc agt                                            4883
```

```
SEQ ID NO: 71          moltype = DNA   length = 1332
FEATURE                Location/Qualifiers
misc_feature           1..1332
                       note = Mevalonate kinase codon-optimized for expression in
                         Escherichia coli
source                 1..1332
                       mol_type = other DNA
                       organism = synthetic construct
SEQUENCE: 71
atgtctctgc cattcctgac gtctgcgcca ggtaaggtga tcatcttcgg cgagcactct     60
gcggtgtaca ataagccggc cgtcgccgcc tctgtgtctg cgttacgcac ctacctgctg    120
atcagcgaat cttctgcacc ggacacgatc gagctggact ttccggacat cagcttcaac    180
cacaagtgga gcatcaacga cttcaacgcg atcacggagg accaggtgaa cagccaaaag    240
ctggccaaag cccagcaagc aaccgacggt ctgtctcagg agctggtgtc tctgctggac    300
ccgctgttag cgcagttaag cgagagcttc cattaccacg ccgcgttctg cttcctgtac    360
atgttcgttt gcctgtgccc gcacgcaaag aacatcaagt tcagcctgaa gagcacgctg    420
ccgattggcg caggcttagg ctctagcgca tctatcgcga tggcctgtgc gctggcgatg    480
gcctatctgg gtggcctgat tggcagcaac gacctggaga aactgagcga aaacgacaag    540
cacatcgtga accagtgggc ctttatcggc gagaagtgca ttcatggcac cccgagcggc    600
attgacaacg cagttgccac gtatggcaac gccctgctgt tcgagaaaga cagccacaac    660
ggcacgatca cacgaacaa cttcaagttc ctggacgcat tcccggcgat cccgatgatt    720
ctgacctaca cccgtatccc acgcagcacc aaggatttag tcgcccgcgt gcgtgttta    780
gtcaccgaaa agttcccgga ggtgatgaag ccgatcctgg acgcgatggg cgagtgcgcg    840
ctgcagggtc tggagatcat gaccaagctg agcaagtgca agggcaccga cgatgaggcg    900
gtggagacca acaatgagct gtacgagcag ctgctggagc tgatccgtat caatcacggc    960
ctgctggtct ctatcggtgt gtctcacccg ggcctggaac tgatcaaaaa cctgagcgac    1020
gacctgcgca ttggctctac gaaattaacg ggtgcaggtg gcggtggctg ctctttaacg    1080
ctgctgcgcc gtgacattac gcaggagcaa atcgacagct tcaagaagaa gctgcaggac    1140
gacttcagct acgagacgtt cgagacggac ctgggcggca cggctgttg cctgctgagc    1200
gccaaaaatc tgaacaagga cctgaagatc aaaagcctgg tgttccagct gttcgaaaac    1260
aagacgacca cgaagcagca gatcgacgac ctgttactgc cgggtaacac caatctgccg    1320
tggacgtctt aa                                                        1332
```

```
SEQ ID NO: 72          moltype = DNA   length = 5220
FEATURE                Location/Qualifiers
misc_feature           1..5220
                       note = Plasmid pAM618
source                 1..5220
                       mol_type = other DNA
                       organism = synthetic construct
SEQUENCE: 72
gcacttttcg gggaaatgtg cgcggaaccc ctatttgttt attttttctaa atacattcaa    60
atatgtatcc gctcatgaga caataaccct gataaatgct tcaataatat tgaaaaagga   120
agagtatgag tattcaacat ttccgtgtcg cccttattcc cttttttgcg gcattttgcc   180
ttcctgtttt tgctcaccca gaaacgctgg tgaaagtaaa agatgctgaa gatcagttgg   240
gtgcacgagt gggttacatc gaactggatc tcaacagcgg taagatcctt gagagttttc   300
gccccgaaga acgttttcca atgatgagca cttttaaagt tctgctatgt ggcgcggtat   360
tatcccgtat tgacgccggg caagagcaac tcggtcgccg catacactat tctcagaatg   420
acttggttga gtactcacca gtcacagaaa agcatcttac ggatggcatg acagtaagag   480
aattatgcag tgctgccata accatgagtg ataacactgc ggccaactta cttctgacaa   540
cgatcggagg accgaaggag ctaaccgctt ttttgcacaa catgggggat catgtaactc   600
gccttgatcg ttgggaaccg gagctgaatg aagccatacc aaacgacgag cgtgacacca   660
cgatgcctgt agcaatggca acaacgttgc gcaaactatt aactggcgaa ctacttactc   720
tagcttcccg gcaacaatta atagactgga tggaggcgga taaagttgca ggaccacttc   780
tgcgctcggc ccttccggct ggctggttta ttgctgataa atctggagcc ggtgagcgtg   840
ggtcccgcgg tatcattgca gcactggggc cagatggtaa gccctcccgt atcgtagtta   900
tctacacgac ggggagtcag gcaactatgg atgaacgaaa tagacagatc gctgagatag   960
gtgcctcact gattaagcat tggtaactgt cagaccaagt ttactcatat atactttaga   1020
ttgatttaaa acttcatttt taatttaaaa ggatctaggt gaagatcctt tttgataatc   1080
tcatgaccaa aatcccttaa cgtgagtttt cgttccactg agcgtcagac cccgtagaaa   1140
agatcaaagg atcttcttga gatccttttt ttctgcgcgt aatctgctgc ttgcaaacaa   1200
aaaaaccacc gctaccagcg gtggtttgtt tgccggatca agagctacca actctttttc   1260
cgaaggtaac tggcttcagc agagcgcaga taccaaatac tgtccttcta gtgtagccgt   1320
agttaggcca ccacttcaag aactctgtag caccgcctac atacctcgct ctgctaatcc   1380
tgttaccagt ggctgctgcc agtggcgata agtcgtgtct taccgggttg gactcaagac   1440
gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccaggggaa acgcctggta tctttatagt cctgtcgggt   1680
ttcgccacct ctgacttgag cgtcgatttt tgtgatgctc gtcagggggg cggagcctat   1740
```

```
ggaaaaacgc cagcaacgcg gccttttac ggttcctggc cttttgctgg ccttttgctc    1800
acatgttctt tcctgcgtta tcccctgatt ctgtggataa ccgtattacc gcctttgagt    1860
gagctgatac cgctcgccgc agccgaacga ccgagcgcag cgagtcagtg agcgaggaag    1920
cggaagagcg cccaatacgc aaaccgcctc tccccgcgcg ttggccgatt cattaatgca    1980
gctgcacga caggtttccc gactggaaag cgggcagtga gcgcaacgca attaatgtga    2040
gttagctcac tcattaggca ccccaggctt tacactttat gcttccggct cgtatgttgt    2100
gtggaattgt gagcggataa caatttcaca caggaaacag ctatgaccat gattacgcca    2160
agctcgaaat taaccctcac taaagggaac aaaagctgga gctgcggccg cgagcttttcc   2220
taaaaaggt tatccaccctt ttttaggatg caagagctat ggaaggtctc tataggcgcc    2280
agcaaccgca cctgtggcgc cggtgatgcc ggccacgatg cgtccggcgt agaggatcga    2340
gatctcgatc ccgcgaaatt aatacgactc actataggg aattgtgagc ggataacaat    2400
tcccctctag aaataatttt gtttaacttt aagaaggaga tatacccata tggaattcga    2460
gctcggtacc cggggatcct ctagagtcga cctgcaggca tgcaagcttg agctcggtac    2520
ccaaactcta tgactgagtt aattaagcag ttcatacagg cgcgccgtct gataaaacag    2580
aatttgcctg gcggcagtag cgcggtggtc ccacctgacc ccatgccgaa ctcagaagtg    2640
aaacgccgta gcgccgatgg tagtgtgggg tctccccatg cgagagtagg gaactgccag    2700
gcatcaaata aaacgaaagg ctcagtcgaa agactgggcc tttcgtttta tctgttgttt    2760
gtcggtgaac gctctcctga gtaggacaaa tccgccggga gcggatttga acgttgcgaa    2820
gcaacgcccc ggagggtggc gggcaggacg cccgccataa actgccaggc atcaaattaa    2880
gcagaaggcc atcctgacgg atggcctttt tgcgtttcta caactctttt ctagagctgc    2940
ctcgcgcgtt tcggtgatga cggtcctctg accggttgga cgttaaaaa tatccccggc    3000
aactgacacg ctaccgggga ttttttttatc atttctgagct tgtctgtaag cggatgccgg    3060
gagcagacaa gcccgtgaag ttcctattct ctagaaagta taggaacttc agagcgcttt    3120
gacgtcggaa ttgccagctg gggcgccctc tggtaaggtt gggaagccct gcaaagtaaa    3180
ctggatggct ttcttgccgc caaggatctg atggcgcagg gatcaagat ctgatcaaga    3240
gacaggatga ggatcgtttc gcatgattga acaagatgga ttgcacgcag gttctccgcc    3300
cgcttgggtg gagaggctat tcggctatga ctgggcacaa cagacaatcg gctgctctga    3360
tgccgccgtg ttccggctgt cagcgcaggg gcgcccggtt cttttttgtca agaccgacct    3420
gtccggtgcc ctgaatgaac tgcaggacga ggcagcgcgg ctatcgtggc tggccacgac    3480
gggcgttcct tgcgcagctg tgctcactga gcgggaaggg actggctgct    3540
attgggcgaa gtgccggggc aggatctcct gtcatctcac cttgctcctg ccgagaaagt    3600
atccatcatg gctgatgcaa tgcggcggct gcatacgctt gatccggcta cctgcccatt    3660
cgaccaccaa gcgaaacatc gcatcgagcg agcacgtact cggatggaag ccggtcttgt    3720
cgatcaggat gatctggacg aagagcatca ggggctcgcg ccagccgaac tgttcgccag    3780
gctcaaggcg cgcatgcccg acggcgagga tctcgtcgtg acccatggcg atgcctgctt    3840
gccgaatatc atggtggaaa atggccgctt ttctggattc atcgactgtg gccggctggg    3900
tgtggcggac cgctatcagg acatagcgtt ggctacccgt gatattgctg aagagcttgg    3960
cggcgaatgg gctgaccgct tcctcgtgct ttacggtatc gccgctcccg attcgcagcg    4020
catcgccttc tatcgccttc ttgacgagtt cttctgagcg ggactctggg gttcgagacc    4080
tcgcttggac tcctgttgat agatccagta atgacctcag aactccatct ggatttgttc    4140
agaacgctcg gttgccgccg ggcgttttt attggtgaga atccaagcac tagttaaggg    4200
gatcttgaag ttcctattcc gaagttccta ttctctagaa agtataggaa cttcacatgc    4260
agctcccgga gacggtcacg cgatcgcttc ttgaagacga aaggcctcg tgatacgcct    4320
atttttatag gttaatgtca tgataataat ggtttcttag acgtcaggtg cactttttcg    4380
gggaaatgtg cgcggaaccc ctatttgttt attttttctaa atacattcaa atatgtatcc    4440
gctcatgaga caataaccct gataaatgct tcaataatat tgaaaaagga agagtgagac    4500
gccacgtacc agccgccgcg tcgacaagct tatgcatcca tgcagttggc catgcctaca    4560
tcgagtacca attcgcccta tagtgagtcg tattacaatt cactggccgt cgttttacaa    4620
cgtcgtgact gggaaaaccc tggcgttacc caacttaatc gccttgcagc acatccccct    4680
ttcgccagct ggcgtaatag cgaagaggcc cgcaccgatc gcccttccca acagttgcgc    4740
agcctgaatg gcgaatggga cgcgccctgt agcggcgcat taagcgcggc gggtgtggtg    4800
gttacgcgca gcgtgaccgc tacacttgcc agcgccctag cgcccgctcc tttcgctttc    4860
ttcccttcct ttctcgccac gttcgccggc tttccccgtc aagctctaaa tcggggctc    4920
cctttagggt tccgatttag tgctttacgg cacctcgacc ccaaaaaact tgattagggt    4980
gatggttcac gtagtgggcc atcgccctga tagacggttt ttcgcccttt gacgttggag    5040
tccacgttct ttaatagtgg actcttgttc caaactggaa caacactcaa ccctatctcg    5100
gtctattctt ttgatttata agggattttg ccgatttcgg cctattggtt aaaaaatgag    5160
ctgatttaac aaaaatttaa cgcgaatttt aacaaaatat taacgcttac aatttaggtg    5220
```

| SEQ ID NO: 73 | moltype = DNA   length = 1356 |
|---|---|
| FEATURE | Location/Qualifiers |
| misc_feature | 1..1356 |
| | note = Phosphomevalonate kinase codon-optimized for expression in Escherichia coli |
| source | 1..1356 |
| | mol_type = other DNA |
| | organism = synthetic construct |

SEQUENCE: 73
```
atgagcgaat tacgtgcatt cagcgcgcca ggtaaggcac tgctggccgg tggctacctg    60
gtgttagaca ccaagtacga ggcgttcgtc gtcggcttat ctgcccgtat gcatgcagtt   120
gcccacccgt atggtagcct gcagggctct gacaagttcg aagtgcgtgt gaagagcaag   180
cagttcaagg acgcgagtg gctgtaccac attagcccaa agagcggctt catcccggtt   240
agcattggtg gcagcaagaa cccatttatc gagaaggtca ttgccaacgt cttcagctac   300
tcaagccga atatgccga ttactgcaac cgcaacctgt tcgtcatcga cattttcagc   360
gacgacgcgt accacagcca agaggactct gttacggagc atcgtggtaa ccgccgcctg   420
agcttccaca gccatcgcat tgaggagtg ccgaagacgg tctgggttc tagcgccggt   480
ttagttaccg tcttaacgac ggcgttagcg agcttcttcg tgagcgacct ggagaacaac   540
gtggacaagt accgcgaagt gattcataac ctggcgcagg tggcacattg tcaggcccaa   600
ggtaagattg gctctggttt tgatgtggca gcggccgcct atggctctat ccgctatgcg   660
```

```
cgctttccgc cggccctgat cagcaatctg ccggacatcg gctctgcgac gtatggtagc   720
aaactggcgc atctggtgga cgaggaggac tggaacatca ccattaagtc taatcacctg   780
ccgagcggct taacgttatg gatgggcgat atcaagaacg gcagcgaaac ggttaagctg   840
gtgcagaaag tgaaaaactg gtacgacagc cacatgccgg aaagcctgaa gatttacacg   900
gagctggacc acgccaatag ccgtttcatg gatggtctga gcaagctgga ccgcctgcac   960
gaaacccacg acgactacag cgaccagatc ttcgagagcc tggagcgcaa tgactgcacc  1020
tgccagaagt acccggagat cacggaggtc cgcgatgccg tggcaacgat tcgccgtagc  1080
ttccgcaaaa ttacgaagga gagcggcgcg gatatcgaac caccggtcca gacgtctctg  1140
ctggacgact gtcaaaccct aaagggcgtg ttaacgtgcc tgattccggg cgcgggtggt  1200
tacgacgcca ttgccgtcat cacgaaacag gacgtcgatc tgcgcgcaca aacggccaac  1260
gacaaacgtt tcagcaaagt ccaatggctg gatgttacgc aggccgactg gggtgttcgc  1320
aaggagaagg acccggaaac gtatctggat aagtga                            1356
```

PRODUCTION OF ISOPRENOIDS

CROSS-REFERENCE TO RELATED APPLICATIONS

This application is a continuation of U.S. application Ser. No. 12/234,589, filed Sep. 19, 2008 (now issued as U.S. Pat. No. 11,725,225), which claims the benefit of U.S. Provisional Application Nos. 60/994,790, filed Sep. 20, 2007, and 61/049,350, filed Apr. 30, 2008, all of which are incorporated herein by reference in their entirety.

REFERENCE TO ELECTRONIC SEQUENCE LISTING

The application contains a Sequence Listing which has been submitted electronically in .XML format and is hereby incorporated by reference in its entirety. Said .XML copy, created on Sep. 29, 2023, is named "107345.00907.xml" and is 157,295 bytes in size. The sequence listing contained in this .XML file is part of the specification and is hereby incorporated by reference herein in its entirety.

FIELD OF THE INVENTION

Provided herein are, among others, compositions and methods for a robust production of isoprenoids. Also provided herein are nucleic acids, enzymes, expression vectors, and genetically modified host cells for carrying out the methods. Also provided herein are fermentation methods for high productivity of isoprenoids from genetically modified host cells.

BACKGROUND OF THE INVENTION

Isoprenoids are ubiquitous in nature. They comprise a diverse family of over 40,000 individual products, many of which are vital to living organisms. Isoprenoids serve to maintain cellular fluidity, electron transport, and other metabolic functions. A vast number of natural and synthetic isoprenoids are useful as pharmaceuticals, cosmetics, perfumes, pigments and colorants, fungicides, antiseptics, nutraceuticals, and fine chemical intermediates.

An isoprenoid product is typically composed of repeating five carbon isopentenyl diphosphate (IPP) units, although irregular isoprenoids and polyterpenes have been reported. In nature, isoprenoids are synthesized by consecutive condensations of their precursor IPP and its isomer dimethylallyl pyrophosphate (DMAPP). Two pathways for these precursors are known. Eukaryotes, with the exception of plants, generally use the mevalonate-dependent (MEV) pathway to convert acetyl coenzyme A (acetyl-CoA) to IPP, which is subsequently isomerized to DMAPP. Prokaryotes, with some exceptions, typically employ only the mevalonate-independent or deoxyxylulose-5-phosphate (DXP) pathway to produce IPP and DMAPP. Plants use both the MEV pathway and the DXP pathway. See Rohmer et al. (1993) *Biochem. J.* 295:517-524; Lange et al. (2000) *Proc. Natl. Acad. Sci. USA* 97(24):13172-13177; Rohdich et al. (2002) *Proc. Natl. Acad. Sci. USA* 99:1158-1163. Traditionally, isoprenoids have been manufactured by extraction from natural sources such as plants, microbes, and animals. However, the yield by way of extraction is usually very low due to a number of profound limitations. First, most isoprenoids accumulate in nature in only small amounts. Second, the source organisms in general are not amenable to the large-scale cultivation that is necessary to produce commercially viable quantities of a desired isoprenoid. Third, the requirement of certain toxic solvents for isoprenoid extraction necessitates special handling and disposal procedures, and thus complicating the commercial production of isoprenoids.

The elucidation of the MEV and DXP metabolic pathways has made biosynthetic production of isoprenoids feasible. For instance, microbes have been engineered to overexpress a part of or the entire mevalonate pathway for production of an isoprenoid named amorpha-4,11-diene (U.S. Pat. Nos. 7,172,886 and 7,192,751) Other efforts have focused on balancing the pool of glyceraldehyde-3-phosphate and pyruvate, or on increasing the expression of 1-deoxy-D-xylulose-5-phosphate synthase (dxs) and IPP isomerase (idi). See Fanner et al. (2001) *Biotechnol. Prog.* 17:57-61; Kajiwara et al. (1997) *Biochem. J.* 324:421-426; and Kim et al. (2001) *Biotechnol. Bioeng.* 72:408-415.

Nevertheless, given the very large quantities of isoprenoid products needed for many commercial applications, there remains a need for expression systems and fermentation procedures that produce even more isoprenoids than available with current technologies. Optimal redirection of microbial metabolism toward isoprenoid production requires that the introduced biosynthetic pathway is properly engineered both to funnel carbon to isoprenoid production efficiently and to prevent build up of toxic levels of metabolic intermediates over a sustained period of time. Provided herein are compositions and methods that address this need and provide related advantages as well.

SUMMARY OF THE INVENTION

Provided herein are compositions and methods for a robust production of isoprenoids. Non-limiting examples of suitable isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,11-diene; diterpenes (derived from four isoprene units) such as taxadiene; triterpenes (derived from 6 isoprene units) such as squalene; tetraterpenes (derived from 8 isoprenoids) such as β-carotene; and polyterpenes (derived from more than 8 isoprene units) such as polyisoprene.

In one aspect, a method for producing an isoprenoid compound is provided wherein the method comprises:
(a) obtaining a plurality of host cells that are capable of making the isoprenoid compound comprising a chromosomally integrated heterologous nucleic acid sequence encoding an enzyme of the MEV or DXP pathway;
(b) culturing the host cells in a medium under conditions wherein the host cells use ethanol as a carbon source and make the isoprenoid compound; and
(c) recovering the isoprenoid compound from the medium.

In some embodiments, the ethanol that is consumed by the host cells as the carbon source is made by the host cell. In other embodiments, the ethanol that is consumed by the host cells as the carbon source is exogenously supplied to the medium.

In another aspect, a method for making an isoprenoid compound is provided which comprises:
(a) obtaining a plurality of host cells that are capable of making the isoprenoid compound;
(b) culturing the host cells in a medium comprising ethanol in an amount equal to or greater than about 1 gram per liter of medium for at least four hours; and (c) recovering the isoprenoid compound from the medium.

In yet another aspect, a method for making an isoprenoid compound is provided which comprises:
(a) obtaining a plurality of yeast cells that are capable of making the isoprenoid compound;
(b) culturing the yeast cells to build biomass by providing a bolus of a carbon source to the medium;
(c) maintaining the cells under conditions whereby the yeast cells have an ethanol consumption rate equal to or greater than about 0.01 gram per ethanol per gram of dry cell weight per hour for at least four hours; and
(d) recovering the isoprenoid compound from the medium.

In some embodiments, the host cells make the isoprenoid compound using the MEV pathway. In other embodiments, the host cells make the isoprenoid compound using the DXP pathway.

In other embodiments, the host cells are cultured or maintained for at least some period of time under oxygen limited conditions. In still other embodiments, the host cells are cultured or maintained for at least some period of time under phosphate limited conditions.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIGS. 4A-4G show maps of DNA fragments: ERG20-PGAL-tHMGR (FIG. 4A), ERG13-PGAL-tHMGR (FIG. 4B), IDI1-PGAL-tHMGR (FIG. 4C), ERG10-PGAL-ERG12 (FIG. 4D), ERG8-PGAL-ERG19 (FIG. 4E), GAL7[4 to 1021]-HPH-GAL1[1637 to 2587] (not shown), GAL80-50 to −1-NatR-GAL801309 to 1358 (FIG. 4F), and GAL1(1 to 48)-NatR-GAL1(1500 to 1550) (FIG. 4G).

DETAILED DESCRIPTION OF THE INVENTION

Definitions

Figure 1:
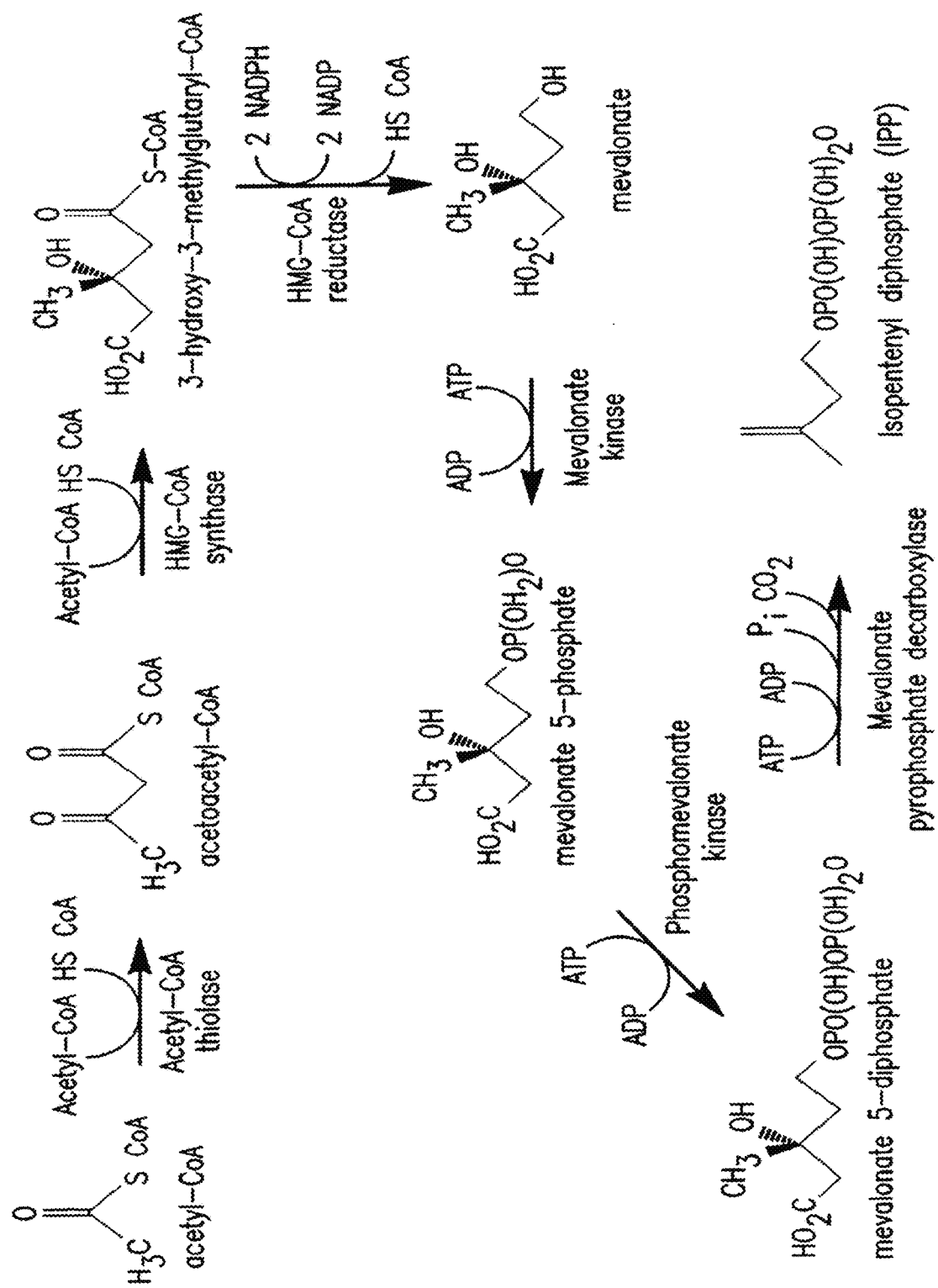
FIG. 1 is a schematic representation of the mevalonate ("MEV") pathway for the production of isopentenyl pyrophosphate ("IPP").

Unless defined otherwise, all technical and scientific terms used herein have the same meaning as commonly understood by one of ordinary skill in the art. Reference is made here to a number of terms that shall be defined to have the following meanings:

The term "optional" or "optionally" means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where the event or circumstance does not occur.

The terms "metabolic pathway" is used herein to refer to a catabolic pathway or an anabolic pathway. Anabolic pathways involve constructing a larger molecule from smaller molecules, a process requiring energy. Catabolic pathways involve breaking down of larger molecules, often releasing energy.

The term "mevalonate pathway" or "MEV pathway" is used herein to refer to the biosynthetic pathway that converts acetyl-CoA to IPP. The MEV pathway is illustrated schematically in FIG. 1.

The term "deoxyxylulose 5-phosphate pathway" or "DXP pathway" is used herein to refer to the pathway that converts glyceraldehyde-3-phosphate and pyruvate to IPP and DMAPP. The DXP pathway is illustrated schematically in FIG. 2.

The word "pyrophosphate" is used interchangeably herein with "diphosphate".

The terms "expression vector" or "vector" refer to a nucleic acid that transduces, transforms, or infects a host cell, thereby causing the cell to produce nucleic acids and/or proteins other than those that are native to the cell, or to express nucleic acids and/or proteins in a manner that is not native to the cell.

The term "endogenous" refers to a substance or process that occurs naturally, e.g., in a non-recombinant host cell.

The terms "enzymatic pathway for making isopentenyl pyrophosphate" refers to any pathway capable of producing isopentyl pyrophosphate, including, without limitation, either the mevalonate pathway or the DXP pathway.

The term "nucleic acid" refers to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically, or biochemically modified, non-natural, or derivatized nucleotide bases.

The term "operon" is used to refer to two or more contiguous nucleotide sequences that each encode a gene product such as a RNA or a protein, and the expression of which are coordinately regulated by one or more controlling elements (for example, a promoter).

The term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The term "protein" refers to a polymeric form of amino acids of any length, which can include coded and non-coded amino acids, chemically or biochemically modified or derivatized amino acids, and polypeptides having modified peptide backbones.

The term "heterologous nucleic acid" as used herein refers to a nucleic acid wherein at least one of the following is true: (a) the nucleic acid is foreign ("exogenous") to (that is, not naturally found in) a given host cell; (b) the nucleic acid comprises a nucleotide sequence that is naturally found in (that is, is "endogenous to") a given host cell, but the nucleotide sequence is produced in an unnatural (for example, greater than expected or greater than naturally found) amount in the cell; (c) the nucleic acid comprises a nucleotide sequence that differs in sequence from an endogenous nucleotide sequence, but the nucleotide sequence encodes the same protein (having the same or substantially the same amino acid sequence) and is produced in an unnatural (for example, greater than expected or greater than naturally found) amount in the cell; or (d) the nucleic acid comprises two or more nucleotide sequences that are not found in the same relationship to each other in nature (for example, the nucleic acid is recombinant).

A "transgene" refers to a gene that is exogenously introduced into a host cell. It can comprise an endogenous or exogenous, or heterologous nucleic acid.

The term "recombinant host" (also referred to as a "genetically modified host cell" or "genetically modified host microorganism") denotes a host cell that comprises a heterologous nucleic acid provided herein.

The term "exogenous nucleic acid" refers to a nucleic acid that is exogenously introduced into a host cell, and hence is not normally or naturally found in and/or produced by a given cell in nature.

The term "regulatory element" refers to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" refers to a permanent or transient genetic change induced in a cell following introduction of new nucleic acid. Genetic change ("modification") can be accomplished either by incorporation of the new DNA into the genome of the host cell, or by transient or stable maintenance of the new DNA as an episomal element. In eukaryotic cells, a permanent genetic change is generally achieved by introduction of the DNA into the genome of the cell. In prokaryotic cells, a permanent genetic change can be introduced into the chromosome or via extrachromosomal elements such as plasmids and expression vectors, which may contain one or more selectable markers to aid in their maintenance in the recombinant host cell.

The term "operably linked" refers to a juxtaposition wherein the components so described are in a relationship permitting them to function in their intended manner. For instance, a promoter is operably linked to a nucleotide sequence if the promoter affects the transcription or expression of the nucleotide sequence.

The term "host cell" and "host microorganism" are used interchangeably herein to refer to any archae, bacterial, or eukaryotic living cell into which a heterologous nucleic acid can be or has been inserted.

The term also relates to the progeny of the original cell, which may not necessarily be completely identical in morphology or in genomic or total DNA complement to the original parent, due to natural, accidental, or deliberate mutation.

The term "synthetic" as used in reference to nucleic acids means the annealing of chemically synthesized oligonucleotide building blocks to form gene segments, which are then enzymatically assembled to construct the entire gene. Synthesis of nucleic acids via "chemical means" means that the component nucleotides were assembled in vitro.

The term "natural" as applied to a nucleic acid, a cell, or an organism, refers to a nucleic acid, cell, or organism that is found in nature. For example, a polypeptide or polynucleotide sequence that is present in a non-pathological (undiseased) organism that can be isolated from a source in nature and that has not been intentionally modified by a human in the laboratory is natural.

The term "naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

The term "biologically active fragment" as applied to a protein, polypeptide or enzyme refers to functional portion(s) of the proteins or polypeptide or enzyme. Functionally equivalents may have variant amino acid sequences may arise, e.g., as a consequence of codon redundancy and functional equivalency which are known to occur naturally within nucleic acid sequences and the proteins thus encoded. Functionally equivalent proteins or peptides may alternatively be constructed via the application of recombinant DNA technology, in which changes in the protein structure may be engineered, based on considerations of the properties of the amino acids being exchanged.

The terms "isoprenoid", "isprenoid compound", "isoprenoid product", "terpene", "terpene compound", "terpenoid", and "terpenoid compound" are used interchangeably herein. They refer to compounds that are capable of being derived from IPP.

The singular forms "a," "and," and "the" include plural referents unless the context clearly dictates otherwise. Thus, for example, reference to "an expression vector" includes a single expression vector as well as a plurality of expression vectors, and reference to "the host cell" includes reference to one or more host cells, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Unless otherwise indicated, the embodiments provided herein are not limited to particular sequences, expression vectors, enzymes, host microorganisms, or processes, as such may vary in accordance with the understanding of those of ordinary skill in the art in view of the teaching herein. Terminology used herein is for purposes of describing particular embodiments only and is not intended to be limiting.

IPP Pathways

The host cells provided herein comprise or utilize the MEV pathway, the DXP pathway or both to synthesize IPP and its isomer, DMAPP. Provided herein is the host cell includes at least one chromosomally integrated heterologous nucleic acid sequence encoding an enzyme of the MEV or DXP pathways. In other embodiments, the host cell includes at least one heterologous nucleic acid sequence encoding a plurality of enzymes of the MEV or DXP pathways. In still other embodiments, the host cell includes a plurality of heterologous nucleic acid sequences encoding all of the MEV pathway enzymes. In yet other embodiments, the host cell includes a plurality of heterologous nucleic acid sequences that encodes all of the DXP pathway enzymes.

In general, eukaryotes other than plants use the MEV isoprenoid pathway exclusively to convert acetyl-CoA to IPP, which is subsequently isomerized to DMAPP. Prokaryotes, with some exceptions, use the mevalonate-independent or DXP pathway to produce IPP and DMAPP separately through a branch point. Plants use both the MEV and DXP pathways for IPP synthesis.

MEV Pathway

A schematic representation of the MEV pathway is described in FIG. 1. In general, the pathway comprises six steps.

In the first step, two molecules of acetyl-coenzyme A are enzymatically combined to form acetoacetyl-CoA. An enzyme known to catalyze this step is, for example, acetyl-CoA thiolase (also known as acetyl-CoA acetyltransferase). Illustrative examples of nucleotide sequences include but are not limited to the following GenBank accession numbers and the organism from which the sequences derived: (NC_000913 REGION: 2324131..2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061..20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734..118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315..713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

If IPP is to be converted to DMAPP, then a seventh step is required. An enzyme known to catalyze this step is, for example, IPP isomerase. Illustrative examples of nucleotide sequences include but are not limited to: (NC_000913, 3031087..3031635; *Escherichia coli*), and (AF082326; *Haematococcus pluvialis*). If the conversion to DMAPP is required, an increased expression of IPP isomerase ensures that the conversion of IPP into DMAPP does not represent a rate-limiting step in the overall pathway.

DXP Pathway

Figure 2:
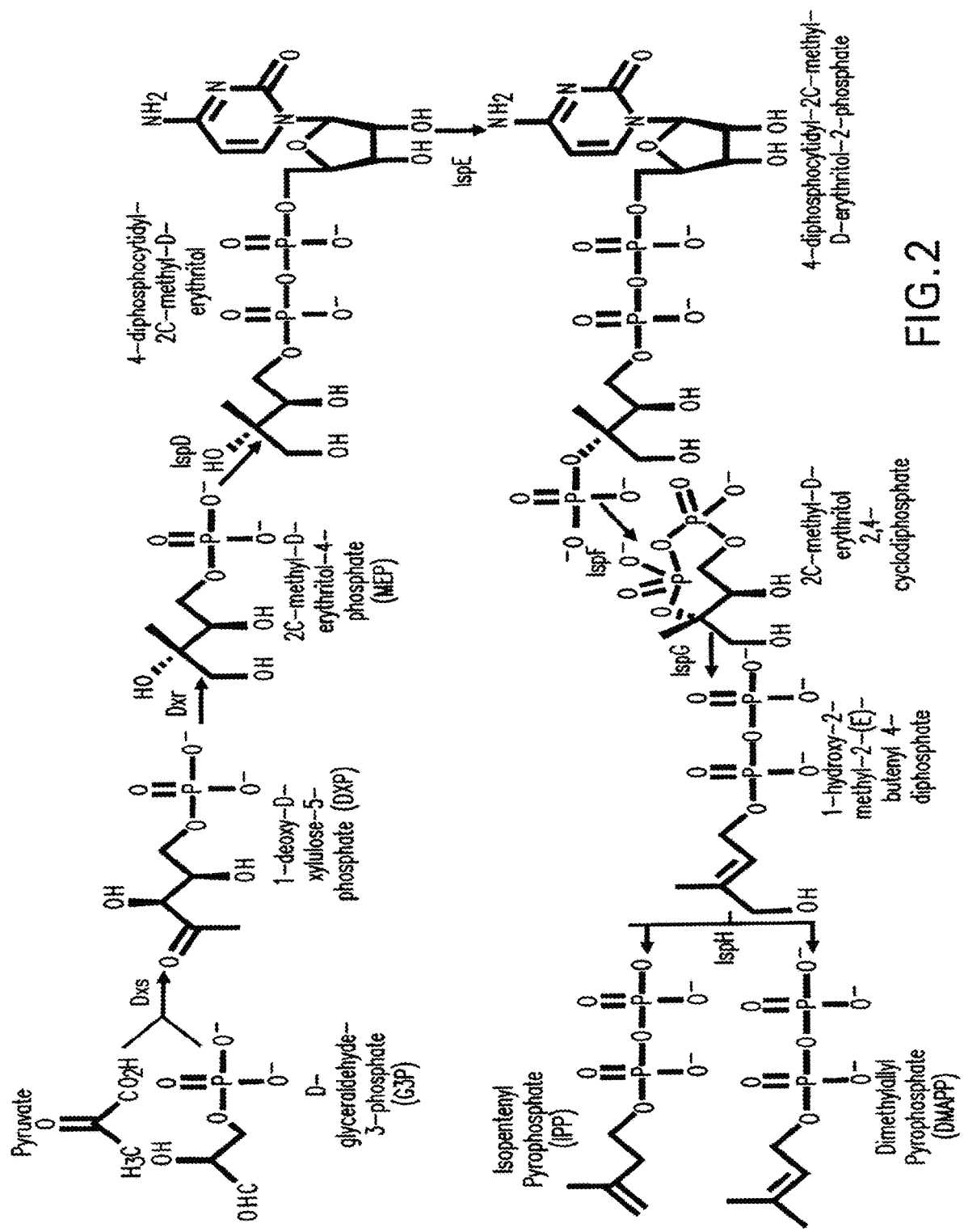
FIG. 2 is a schematic representation of the 1-deoxy-D-xylulose 5-diphosphate ("DXP") pathway for the production of isopentenyl pyrophosphate ("IPP") and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

A schematic representation of the DXP pathway is described in FIG. 2. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica* Paratyphi, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD 1293; *Xylella fastidiosa* Temecula1), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus tag RSP_2835; *Rhodobacter sphaeroides* 2.4.1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus_tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2, 4-cyclodiphosphate. An enzyme known to catalyze this step is, for example, 2C-methyl-D-erythritol 2, 4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2.4.1), and (NC_002947, locus_tag PP1618; *Pseudomonas putida* KT2440).

In the sixth step, 2C-methyl-D-erythritol 2, 4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus_tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus_tag PP0606; *Pseudomonas putida* KT2440).

In some embodiments, "cross talk" (or interference) between the host cell's own metabolic processes and those processes involved with the production of IPP as provided herein are minimized or eliminated entirely. For example, cross talk is minimized or eliminated entirely when the host microorganism relies exclusively on the DXP pathway for synthesizing IPP, and a MEV pathway is introduced to provide additional IPP. Such a host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

Host Cells

Illustrative examples of suitable host cells for use provided herein include any archae, prokaryotic, or eukaryotic cell. Examples of an archae cell include, but are not limited to those belonging to the genera: *Aeropyrum, Archaeglobus, Halobacterium, Methanococcus, Methanobacterium, Pyrococcus, Sulfolobus*, and *Thermoplasma*. Illustrative examples of archae strains include but are not limited to: *Aeropyrum pernix, Archaeoglobus fulgidus, Methanococcus jannaschii, Methanobacterium* thermoautotrophicum, *Pyrococcus abyssi, Pyrococcus horikoshii, Thermoplasma acidophilum, Thermoplasma volcanium*.

Examples of a procaryotic cell include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus,* and *Zymomonas*.

Illustrative examples of prokaryotic bacterial strains include but are not limited to: *Bacillus subtilis, Bacillus amyloliquefacines, Brevibacterium ammoniagenes, Brevibacterium immariophilum, Clostridium beigermckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus,* and the like.

In general, if a bacterial host cell is used, a non-pathogenic strain is preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevaloni, Pseudomonas pudita, Rhodobacter sphaeroides, Rodobacter capsulatus, Rhodospirillum rubrum,* and the like.

Examples of eukaryotic cells include but are not limited to fungal cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic strains include but are not limited to: *Aspergillus nidulans, Aspergillus niger, Aspergillus oryzae, Candida albicans, Chrysosporium lucknowense, Fusarium grammnearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pyperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccharomyces bayanus, Saccharomyces boulardi, Saccharomyces cerevisiae, Streptomyces fungicidicus,*

Streptomyces griseochromogenes, Streptomyces griseus, Streptomyces lividans, Streptomyces olivogriseus, Streptomyces rameus, Streptomyces tanashtensis, Streptomyces vinaceus, Trichoderma reesei and Xanthophyllomyces dendrorhous (formerly Phaffia rhodozyma).

In general, if a eukaryotic cell is used, a non-pathogenic strain is preferred. Illustrative examples of non-pathogenic strains include but are not limited to: Fusarium graminearum, Fusarium venenatum, Pichia pastoris, Saccharomyces boulardi, and Saccharomyces cerevisiae.

In addition, certain strains have been designated by the Food and Drug Administration as GRAS or Generally Regarded As Safe. These strains include: Bacillus subtilis, Lactibacillus acidophilus, Lactobacillus helveticus, and Saccharomyces cerevisiae.

Isoprenoid Compounds

The host cells provided herein are used to make isprenoids. Specific isprenoid compounds are made from IPP or DMAPP and may require additional finishing enzymes. Non-limiting examples of suitable isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,11-diene; diterpenes (derived from four isoprene units) such as taxadiene; triterpenes (derived from 6 isoprene units) such as squalene; tetraterpenes (derived from 8 isoprenoids) such as β-carotene; and polyterpenes (derived from more than 8 isoprene units) such as polyisoprene. In some embodiments, the isoprenoid is not a carotenoid. In other embodiments, the isoprenoid is a $C_5$-$C_{20}$ isoprenoid. Illustrative examples of specific $C_5$-$C_{20}$ isoprenoid compounds and their respective finishing enzymes are further described below.

$C_5$ Compounds $C_5$ compounds provided herein generally are derived from IPP or DMAPP. These compounds are also known as hemiterpenes because they are derived from a single isoprene unit (IPP or DMAPP).

Isoprene

Isoprene, whose structure is

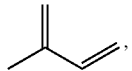

is found in many plants. Isoprene is made from IPP by isoprene synthase. Illustrative examples of suitable nucleotide sequences include but are not limited to: (AB198190; Populus alba) and (AJ294819; Polulus alba×Polulus tremula).

$C_{10}$ Compounds $C_{10}$ compounds provided herein generally derived from geranyl pyrophosphate (GPP) which is made by the condensation of IPP with DMAPP. An enzyme known to catalyze this step is, for example, geranyl pyrophosphate synthase. These $C_{10}$ compounds are also known as monoterpenes because they are derived from two isoprene units.

Figure 3:
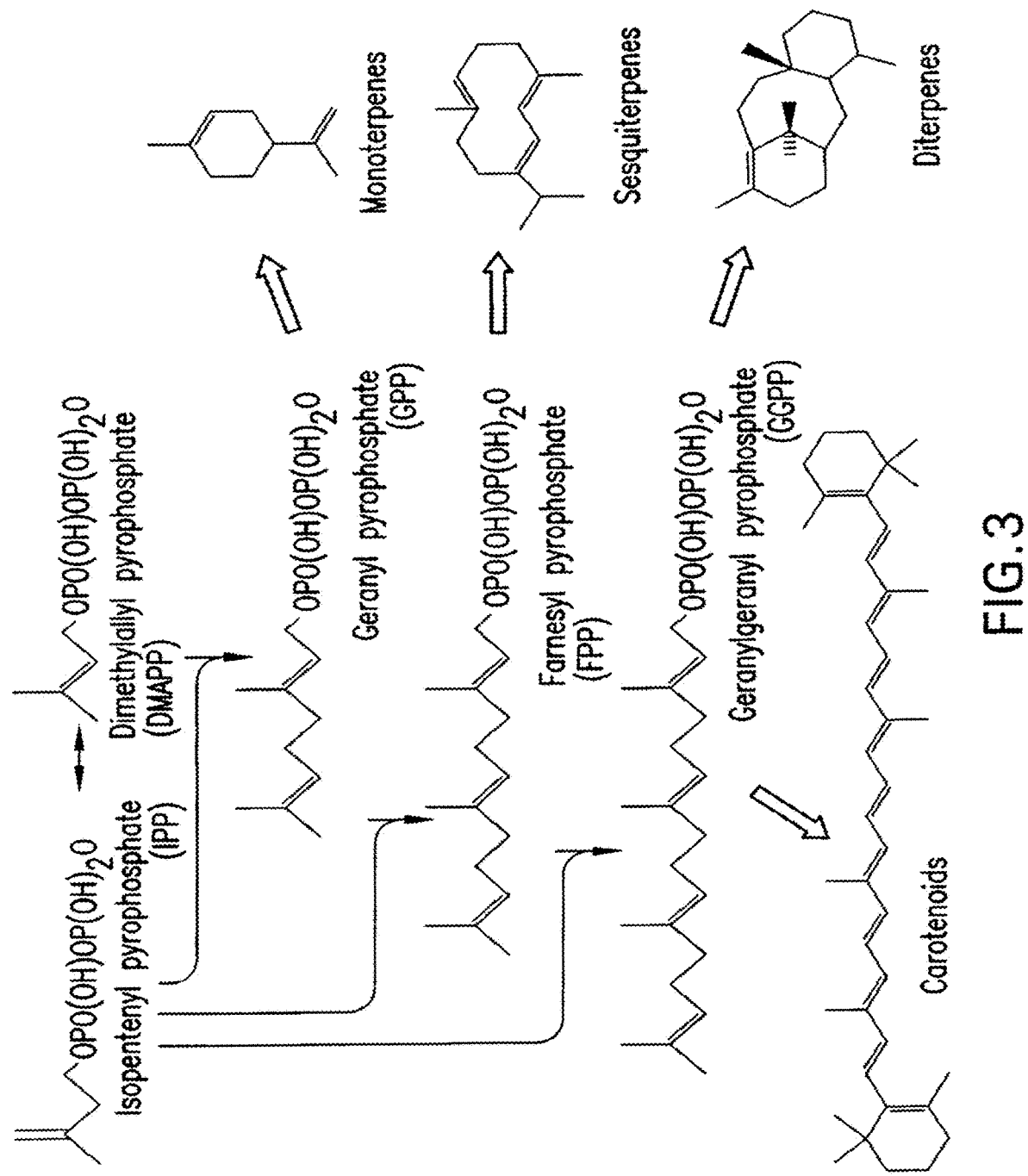
FIG. 3 is a schematic representation of the conversion of isopentenyl pyrophosphate ("IPP") and dimethylallyl pyrophosphate ("DMAPP") to geranyl pyrophosphate ("GPP"), farnesyl pyrophosphate ("FPP"), and geranylgeranyl pyrophosphate ("GGPP"), and the synthesis of various isoprenoids.

FIG. 3 shows schematically how IPP and DMAPP can produce GPP, which can be further processed to a monoterpene.

Illustrative examples of nucleotide sequences for geranyl pyrophosphate synthase include but are not limited to: (AF513111; Abies grandis), (AF513112; Abies grandis), (AF513113; Abies grandis), (AY534686; Antirrhinum majus), (AY534687; Antirrhinum majus), (Y17376; Arabidopsis thaliana), (AE016877, Locus AP11092; Bacillus cereus; ATCC 14579), (AJ243739; Citrus sinensis), (AY534745; Clarkia breweri), (AY953508; Ips pini), (DQ286930; Lycopersicon esculentum), (AF182828; Menthaxpiperita), (AF182827; Menthaxpiperita), (MP1249453; Menthaxpiperita), (PZE431697, Locus CAD24425; Paracoccus zeaxanthinafaciens), (AY866498; Picrorhiza kurrooa), (AY351862; Vitis vinifera), and (AF203881, Locus AAF12843; Zymomonas mobilis).

GPP is then subsequently converted to a variety of $C_{10}$ compounds. Illustrative examples of $C_{10}$ compounds include but are not limited:

Carene

Carene, whose structure is

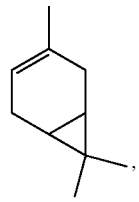

is found in the resin of many trees, particularly pine trees. Carene is made from GPP from carene synthase. Illustrative examples of suitable nucleotide sequences include but are not limited to: (AF461460, REGION 43..1926; Picea abies) and (AF527416, REGION: 78..1871; Salvia stenophylla).

Geraniol

Geraniol (also known as rhodnol), whose structure is

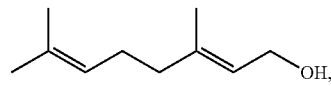

is the main component of oil-of-rose and palmarosa oil. It also occurs in geranium, lemon, and citronella. Geraniol is made from GPP by geraniol synthase. Illustrative examples of suitable nucleotide sequences include but are not limited to: (AJ457070; Cinnamomum tenuipilum), (AY362553; Ocimum basilicum), (DQ234300; Perilla frutescens strain 1864), (DQ234299; Perilla citriodora strain 1861), (DQ234298; Perilla citriodora strain 4935), and (DQ088667; Perilla citriodora)

Linalool

Linalool, whose structure is

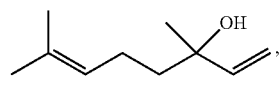

is found in many flowers and spice plants such as coriander seeds. Linalool is made from GPP by linalool synthase. Illustrative examples of a suitable nucleotide sequence include but are not limited to: (AF497485; Arabidopsis thaliana), (AC002294, Locus AAB71482; Arabidopsis thaliana), (AY059757; Arabidopsis thaliana), (NM_104793; Arabidopsis thaliana), (AF154124; Artemisia annua), (AF067603; Clarkia breweri), (AF067602; Clarkia concinna), (AF067601; Clarkia breweri), (U58314; Clarkia breweri), (AY840091; Lycopersicon esculentum), (DQ263741; *Lavandula angustifolia*), (AY083653; *Mentha citrate*), (AY693647; *Ocimum basilicum*), (XM 463918; *Oryza sativa*), (AP004078, Locus BAD07605; *Oryza sativa*), (XM 463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79).

Limonene

Limonene, whose structure is

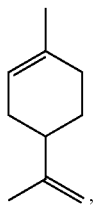

is found in the rind of citrus fruits and peppermint. Limonene is made from GPP by limonene synthase. Illustrative examples of suitable nucleotide sequences include but are not limited to: (+)-limonene synthases (AF514287, REGION: 47..1867; *Citrus limon*) and (AY055214, REGION: 48..1889; *Agastache rugosa*) and (−)-limonene synthases (DQ195275, REGION: 1..1905; *Picea sitchensis*), (AF006193, REGION: 73..1986; *Abies grandis*), and (MHC4SLSP, REGION: 29..1828; *Mentha spicata*).

Myrcene

Myrcene, whose structure is

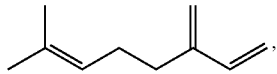

is found in the essential oil in many plants including bay, verbena, and myrcia from which it gets its name. Myrcene is made from GPP by myrcene synthase. Illustrative examples of suitable nucleotide sequences include but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

Ocimene

α- and β-Ocimene, whose structures are

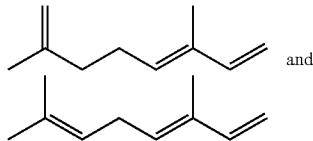

respectively, are found in a variety of plants and fruits including *Ocimum basilicum* and is made from GPP by ocimene synthase. Illustrative examples of suitable nucleotide sequences include but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

α-Pinene

α-Pinene, whose structure is

is found in pine trees and eucalyptus. α-Pinene is made from GPP by α-pinene synthase. Illustrative examples of suitable nucleotide sequences include but are not limited to: (+) α-pinene synthase (AF543530, REGION: 1..1887; *Pinus taeda*), (−)α-pinene synthase (AF543527, REGION: 32..1921; *Pinus taeda*), and (+)/(−)α-pinene synthase (AGU87909, REGION: 6111892; *Abies grandis*).

β-Pinene

β-Pinene, whose structure is

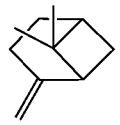

is found in pine trees, rosemary, parsley, dill, basil, and rose. β-Pinene is made from GPP by β-pinene synthase. Illustrative examples of suitable nucleotide sequences include but are not limited to: (−) β-pinene synthases (AF276072, REGION: 1..1749; *Artemisia annua*) and (AF514288, REGION: 26..1834; *Citrus limon*).

Sabinene

Sabinene, whose structure is

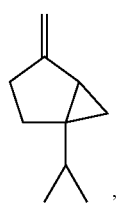

is found in black pepper, carrot seed, sage, and tea trees. Sabinene is made from GPP by sabinene synthase. An illustrative example of a suitable nucleotide sequence includes but is not limited to AF051901, REGION: 26..1798 from *Salvia officinalis*.

γ-Terpinene

γ-Terpinene, whose structure is

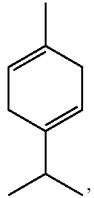

is a constituent of the essential oil from citrus fruits. Biochemically, γ-terpinene is made from GPP by a γ-terpinene synthase. Illustrative examples of suitable nucleotide sequences include: (AF514286, REGION: 30..1832 from *Citrus limon*) and (AB110640, REGION 1..1803 from *Citrus unshiu*).

Terpinolene

Terpinolene, whose structure is

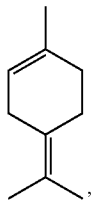

is found in black currant, cypress, guava, lychee, papaya, pine, and tea. Terpinolene is made from GPP by terpinolene synthase. An illustrative example of a suitable nucleotide sequence includes but is not limited to AY906866, REGION: 10..1887 from *Pseudotsuga menziesii*.

$C_{15}$ Compounds $C_{15}$ compounds provided herein generally derive from farnesyl pyrophosphate (FPP) which is made by the condensation of two molecules of IPP with one molecule of DMAPP. An enzyme known to catalyze this step is, for example, farnesyl pyrophosphate synthase. These $C_{15}$ compounds are also known as sesquiterpenes because they are derived from three isoprene units.

FIG. 3 shows schematically how IPP and DMAPP can be combined to produce FPP, which can be further processed to a sesquiterpene.

Illustrative examples of nucleotide sequences for farnesyl pyrophosphate synthase include but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), and (MZEFPS; *Zea mays*).

Alternatively, FPP can also be made by adding IPP to GPP. Illustrative examples of nucleotide sequences encoding for an enzyme capable of this reaction include but are not limited to: (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobnum japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar Copenhageni str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula1).

FPP is then subsequently converted to a variety of $C_{15}$ compounds. Illustrative examples of $C_{15}$ compounds include but are not limited to:

Amorphadiene

Amorphadiene, whose structure is

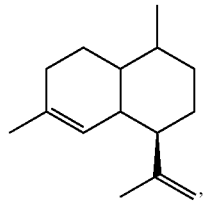

is a precursor to artemisinin which is made by *Artemisia anna*. Amorphadiene is made from FPP by amorphadiene synthase. An illustrative example of a suitable nucleotide sequence is SEQ ID NO. 37 of U.S. Pat. No. 7,192,751.

α-Farnesene

α-Farnesene, whose structure is

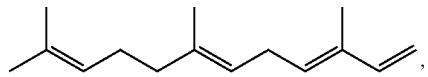

is found in various biological sources including but not limited to the Dufour's gland in ants and in the coating of apple and pear peels. α-Farnesene is made from FPP by α-farnesene synthase. Illustrative examples of suitable nucleotide sequences include but are not limited to DQ309034 from *Pyrus communis* cultivar d'Anjou (pear; gene name AFS1) and AY182241 from *Malus domestica* (apple; gene AFS1). Pechouus et al., *Planta* 219(1):84-94 (2004).

β-Farnesene

β-Farnesene, whose structure is

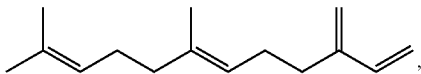

is found in various biological sources including but not limited to aphids and essential oils such as from peppermint. In some plants such as wild potato, β-farnesene is synthesized as a natural insect repellent. β-Farnesene is made from FPP by β-farnesene synthase. Illustrative examples of suitable nucleotide sequences include but is not limited to GenBank accession number AF024615 from *Menthaxpiperita* (peppermint; gene Tspa11), and AY835398 from *Artemisia annua*. Picaud et al., *Phytochemistry* 66(9): 961-967 (2005).

Farnesol

Farnesol, whose structure is

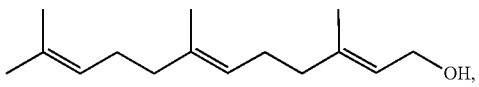

is found in various biological sources including insects and essential oils such as from cintronella, neroli, cyclamen, lemon grass, tuberose, and rose. Farnesol is made from FPP by a hydroxylase such as farnesol synthase. Illustrative examples of suitable nucleotide sequences include but are not limited to GenBank accession number AF529266 from *Zea mays* and YDR481C from *Saccharomyces cerevisiae* (gene Pho8). Song, L., *Applied Biochemistry and Biotechnology* 128:149-158 (2006).

Nerolidol

Nerolidol, whose structure is

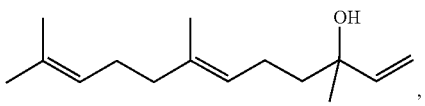 [SMILES: C=CC(C)(O)CC/C=C(\C)CCC=C(C)C]

is also known as peruviol, and is found in various biological sources including as essential oils such as from neroli, ginger, jasmine, lavender, tea tree, and lemon grass. Nerolidol is made from FPP by a hydroxylase such as nerolidol synthase. An illustrative example of a suitable nucleotide sequence includes but is not limited to AF529266 from *Zea mays* (maize; gene tps1).

Patchoulol

Patchoulol, whose structure is

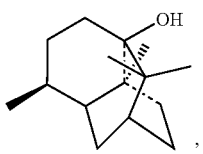

is also known as patchouli alcohol and is a constituent of the essential oil of *Pogostemon* patchouli. Patchouliol is made from FPP by patchouliol synthase. An illustrative example of a suitable nucleotide sequence includes but is not limited to AY508730 REGION: 1..1659 from *Pogostemon cablin*.

Valencene

Valencene, whose structure is

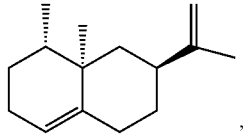

is one of the main chemical components of the smell and flavour of oranges and is found in orange peels. Valencene is made from FPP by nootkatone synthase. Illustrative examples of a suitable nucleotide sequence includes but is not limited to AF441124 REGION: 1..1647 from *Citrus sinensis* and AY917195 REGION: 1..1653 from *Perilla frutescens*.

$C_{20}$ Compounds $C_{20}$ compounds provided herein generally derived from geranylgeraniol pyrophosphate (GGPP) which is made by the condensation of three molecules of IPP with one molecule of DMAPP. An enzyme known to catalyze this step is, for example, geranylgeranyl pyrophosphate synthase. These $C_{20}$ compounds are also known as diterpenes because they are derived from four isoprene units.

FIG. 3 shows schematically how IPP and DMAPP can be combined to produce GGPP, which can be further processed to a diterpene, or can be further processed to produce a carotenoid.

Illustrative examples of nucleotide sequences for geranylgeranyl pyrophosphate synthase include but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MC1276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus acidtrophicus* SB), and (NC_006840, Locus YP_204095; *Vibrio fischeri* ES114).

Alternatively, GGPP can also be made by adding IPP to FPP. Illustrative examples of nucleotide sequences encoding an enzyme capable of this reaction include but are not limited to: (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

GGPP is then subsequently converted to a variety of $C_{20}$ isoprenoids. Illustrative examples of $C_{20}$ compounds include but are not limited to:

Geranylgeraniol
  Geranylgeraniol, whose structure is

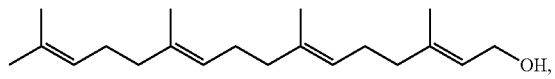 [SMILES: CC(C)=CCC/C(C)=C/CC/C(C)=C/CC/C(C)=C/CO]

is a constituent of wood oil from *Cedrela toona* and of linseed oil. Geranylgeraniol can be made by e.g., adding to the expression constructs a phosphatase gene after the gene for a GGPP synthase.
Abietadiene
  Abietadiene encompasses the following isomers:

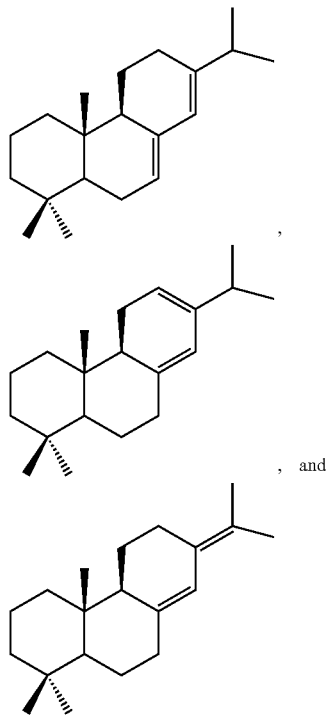

, and and is found in trees such as *Abies grandis*. Abietadiene is made by abietadiene synthase. An illustrative example of a suitable nucleotide sequence includes but are not limited to: (U50768; *Abies grandis*) and (AY473621; *Picea abies*).
$C_{20+}$ Compounds
  $C_{20+}$ compounds are also within the scope provided herein. Illustrative examples of such compounds include sesterterpenes ($C_{25}$ compound made from five isoprene units), triterpenes ($C_{30}$ compounds made from six isoprene units), and tetraterpenes ($C_{40}$ compound made from eight isoprene units).
  These compounds are made by using similar methods described herein and substituting or adding nucleotide sequences for the appropriate synthase(s).
High Yields of Isoprenoid Compounds
  Provided herein are compositions and methods for a robust production of isoprenoids by culturing or maintaining the host cells under conditions in which ethanol is used as a carbon source. Using the methods described herein, the host cells produce more than about 5 grams of isoprenoid per liter of fermentation reaction mixture (5 g/L). In other embodiments, more than about 10 g/L, more than about 15 g/L, more than about 20 g/L, more than about 25 g/L is produced, or more than about 30 g/L of isoprenoid is produced.

Alternatively isoprenoid production can be expressed in terms of specific productivity instead of yields. For example, using the methods described herein, the host cells produce more about 50 milligrams of isoprenoid per gram of dry host cells. In other embodiments, more than about 100 milligrams per gram dry cell weight, more than about 150 milligrams per gram dry cell weight, more than about 200 milligrams per gram dry cell weight, more than about 250 milligrams per gram dry cell weight, more than about 500 milligrams per gram dry cell weight, more than about 750 milligrams per gram dry cell weight, or more than about 1000 milligrams per gram dry cell weight of isoprenoid is produced.
  Whether the production level is expressed in terms of yield or specific productivity, production occurs in less than about 120 hours, less than about 96 hours, less than about 72 hours, preferably less than about 48 hours, or even less than about 24 hours.
  The methods provided herein can be carried out in a batch, a fed-batch, or a continuous process. A batch process is typically a closed process where all of the raw materials are added at the beginning of the process. A fed-batch process is typically a closed process where the carbon source and/or other substrates are added in increments throughout the process. A fed-batch process allows for greater control of the medium and the growth of the microorganisms. A continuous process can be considered an open system where medium is continuously added and product is simultaneously removed.
  Processes in between fed-batch and continuous processes can also be used. For example, in one embodiment, the process is begun as a fed-batch process, and an organic layer, is placed in contact with the culturing medium while the process continues. Isoprenoids, which typically have a higher solubility in an organic solution than in an aqueous solution, are extracted out of the medium into the organic layer. Because product is removed from the medium, this method has characteristics of both a fed-batch and a continuous process.
  Product removal through an organic overlay (e.g. dodecane, isopropyl myristate, methyl oleate and the like) can often lead to increases in isoprenoid production. Product removal can lead to production increases and is desirable particularly where product accumulation leads to pathway inhibition. In certain embodiments, the organic layer can be formed by the isoprenoid product itself. This occurs where the isoprenoid is produced in excess of its saturation point and form a layer separable from the aqueous medium.
  In some embodiments, ethanol is the sole carbon source for host cells. In other embodiments, the carbon source includes both ethanol and a non-ethanol carbon source. In still other embodiments, the non-ethanol carbon source is a carbohydrate.
  Illustrative examples of carbohydrates include monosaccharides, disaccharides, and combinations thereof. Some non-limiting examples of suitable monosaccharides include glucose, galactose, mannose, fructose, ribose, and combinations thereof. Some non-limiting examples of suitable disaccharides include sucrose, lactose, maltose, trehalose, cellobiose, and combinations thereof. Some non-limiting examples of suitable polysaccharides include starch, glycogen, cellulose, chitin, and combinations thereof. Other sources of carbohydrates include cane juice and molasses.
  In general, polysaccharides are first converted into monosaccharides and oligosaccharides by chemical means or by enzymatic methods before they used as a source of carbon for host cells. For instance, cellulose can be converted into glucose by the enzyme cellulase. In certain embodiments, after the breakdown of the polysaccharide, the monosaccharide and/or oligosaccharide constitute at least about 50% by weight of the carbon source as determined at the beginning of the fermentation. In other embodiments, the monosaccharide and/or oligosaccharide constitute at least about 80% or even 90% by weight of the carbon source as determined at the beginning of the fermentation, such that the fermentation medium is essentially free of cellulose.

In certain embodiments, the host cells are exogenously provided ethanol as a carbon source. In other embodiments, the ethanol that is consumed by the host cells as the carbon source was made by the host cells. In other words, the host cells are provided a non-ethanol carbon source (typically a carbohydrate) which is converted by the host cells into ethanol and the ethanol is subsequently consumed by the host cells.

The host cells' use of ethanol can be quantified in a number of ways. In one method, ethanol concentration is used. In addition to being a carbon source, the presence of ethanol in the medium also has the beneficial effects of deterring microbial contaminants.

Thus, in one embodiment, the ethanol concentration in the medium is at least about 1 gram per liter of medium for at least 4 hours. The ethanol concentration can be determined by any method known in the art. It can be measured directly by sampling the medium or indirectly by sampling the offgas. If an indirect method is used such as offgas analysis by mass spectrophotometer, a correlation first be must be established between the offgas measurements in parts per million and the direct measurements of ethanol in the medium. In other embodiments, the ethanol concentration in the medium is between about 1 and about 5 grams, between about 1 and about 10 grams, or between about 1 and about 20 grams per liter of medium. In still other embodiments, the ethanol concentration in the medium is greater than about 10 grams per liter of medium or greater than about 20 grams per liter of medium. In yet other embodiments, the above ethanol concentrations are maintained for at least 6 hours, 8 hours, 10 hours, 12 hours, 24 hours, or 48 hours.

However, host cells can be using ethanol as a carbon source but still have undetectable levels of ethanol or have ethanol concentration close to zero. For example, this can occur when the host cells are consuming ethanol as fast as the ethanol is being supplied. As a result, provided herein are alternative measures for the host cells' ethanol utilization.

In another embodiment, the host cells have a specific ethanol consumption rate of at least 0.01 gram of ethanol per gram of dry cell weight per hour. In other embodiments, the specific ethanol consumption rate is between about 0.01 and about 0.20 gram of ethanol, or between about 0.02 and about 0.10 gram of ethanol per gram of dry cell weight per hour. In still other embodiments, the specific ethanol consumption rate is greater than about 0.10 gram of ethanol per gram of dry cell weight per hour. The specific ethanol consumption rate is maintained for at least 4 hours, 6 hours, 8 hours, 10 hours, 12 hours, 24 hours, or 48 hours.

Alternatively, specific ethanol consumption rate is expressed in terms of grams of ethanol per gram of dry cell weight per day. In some embodiments, the host cells have a specific ethanol consumption rate of at least 0.2 grams of ethanol per gram of dry cell weight per day. In some embodiments, the specific ethanol consumption rate is between about 0.2 and about 5 grams or between about 0.5 and about 3 of ethanol per gram of dry cell weight per day. In other embodiments, the specific ethanol consumption rate is greater than about 3 grams of ethanol per gram of dry cell weight per day.

In certain embodiments, the cells are cultured or maintained under conditions that are not limited by oxygen. In other words, the cells are under aerobic conditions.

However, maintaining fully aerobic conditions can be challenging particularly in large scale processes oxygen due to limitations of mass transfer and the relatively low solubility of oxygen in aqueous solutions. For example, if air is used to sparge into tanks, the solubility of oxygen in water is 9 milligrams per liter at 20° C. If pure oxygen is used instead of air, then the solubility increases to 43 milligrams per liter. In either case (sparging air or pure oxygen), this amount of oxygen is depleted in seconds by an active and concentrated microbial population unless oxygen is continuously supplied. In comparison, the amounts of other nutrients that are used by the cells during the same period (seconds, e.g., less than a minute) are negligble compared to the bulk concentrations.

We have found that the host cells provided herein are able to tolerate some period of oxygen limitation is and still make high levels of isoprenoid compounds. This flexibility allows for a more economical process by providing savings in terms of tank design, decreased demain for oxygen gas, lower energy costs for aeration and the like. Moreover, under certain circumstances, oxygen limitation appears to be beneficial. Without being bound by theory, cell growth under oxygen limited conditions appears to allow more of the carbon to be directed to product instead of biomass or loss through carbon dioxide.

As a consequence, in certain other embodiments, the host cells are cultured or maintained under conditions that are oxygen limited. The periods of oxygen limitation include at least 4 hours, at least 6 hours, at least 8 hours, at least 10 hours, at least 12 hours, at least 24 hours, or at least 48 hours.

Oxygen limitation occurs when the specific growth rate of the host cells is less than the maximum specific growth rate where oxygen is not limiting (e.g., provided in excess). Specific growth rate is the rate of growth of cells per unit of biomass per unit time and has the units of reciprocal time (1/t). The maximum specific growth rate for cells in a culture medium relates to the effect of a substrate concentration on growth rate which in this case is oxygen. Generally, cells will grow slowly at a low level of the substrate, and as the level of the substrate in the medium increases, so does the rate of cell growth. However, the rate of cell growth does not continue to rise indefinitely, and at high levels of substrate, a given increase in the amount of substrate will produce a smaller and smaller increase in the rate of cell growth. Therefore, the growth rate ultimately reaches a limit, which is often referred to as the maximum specific growth rate.

A theoretical treatment of the relationship between growth rates in culture is well known to those skilled in the art, and is referred to as the Monod equation. See, for example, Pirt, Principles of Microbe and Cell Cultivation, Wiley, N Y, 1975, pages 4-10. In this theoretical treatment, the maximum specific rate is an asymptotic limit that is never reached until an infinite level of substrate is reached. In practice, however, the maximum specific growth rate can be considered as being obtained when the conditions under investigation (e.g., a substrate level such as oxygen) support the fastest initial growth rate. For instance, in a fed-batch reactor, the initial condition where all substrates required for growth (e.g. nutrients and oxygen) are supplied in excess and fermentation occurs at the optimal temperature for the host cell is treated as the conditions for the maximum growth rate. See, for example, Lee et al. (1996) *Trends Biotechnol.* 14: 98-105 and Korz et al. (1995) *J Biotechnology* 39:59-65. Maximum specific growth rate is also sometimes referred to as unlimited growth.

In one method, oxygen limitation is quantified by oxygen concentration in the medium and is expressed in terms of dissolved oxygen concentration (DOC). The DOC in the culture medium can be less than about 20%, less than about 15%, less than about 10%, and less than about 5%. In other embodiments the DOC is about 0% or below the level of detection.

However, because oxygen is consumed by the cells relatively rapidly, a DOC of zero can mean that the cells are being cultured under anaerobic conditions (no oxygen) or that the cells are consuming oxygen as fast as it is being supplied. In another method, the cells' use of oxygen is expressed in terms of oxygen uptake rate (OUR; the cells' rate of oxygen consumption per liter of medium) to differentiate between these two possibilities. Suitable oxygen uptake rates include less than about 50 mmoles, less than about 40 mmoles, less than about 30 mmoles, less than about 20 mmoles per liter of medium, or less than about 10 mmoles per liter of medium.

Alternatively, specific oxygen uptake rate (SOUR which is OUR divided by cell density) can be used when normalized values with respect to cell densities is preferred. The amount of microorganism per liter of fermentation, or the density of microorganism, can be measured by measuring the weight of microorganism isolated from a given volume of the fermentation medium. A common measure is the dry weight of cells per liter of fermentation medium. Another method which can be used to monitor the fermentation while it is progressing is by a measurement of the optical density of the medium. A common method is to measure the optical density at a wavelength of 600 nm, referred to the $OD_{600}$, or the OD. The OD can be correlated to a the density of a specific type of organism within a specific medium, but the specific relationship between OD and amount of microorganism per volume will not generally be applicable across all types of organisms in all types of media. A calibration curve can be created by measuring the OD and the dry cell weight over a range of cell densities. In some cases, these correlations can be used in different fermentation of the same or similar microorganisms in the same or similar media. Suitable specific oxygen uptake rates include less than about 30 mmoles, less than about 25 mmoles, less than about 20 mmoles, less than about 15 mmoles, less than about 10 mmoles, or less than about 5 mmoles per gram of dry cell weight per hour.

We have also found that the host cells provided herein are able to tolerate some period of phosphate limitation and still make high levels of isoprenoid compounds. Without being bound by theory, cell growth under phosphate limited conditions appears to allow more of the carbon to be directed to product instead of biomass. Suitable concentrations of phosphate in the medium is less than about 5 grams, less than about 4 grams, less than about 3 grams, less than about 2 grams, or less than about 1 gram per liter of medium. In certain embodiments, the phosphate concentration is zero or below the level of detection. The periods of such phosphate limitation include at least 4 hours, at least 6 hours, at least 8 hours, at least 10 hours, at least 12 hours, at least 24 hours, or at least 48 hours.

Host cells can be grown under non-limiting conditions (allowing for maximum specific growth) to build sufficient biomass before limiting conditions (oxygen limited, phosphate limited, or both) are imposed. These limiting conditions include those such that specific growth is less than about 90%, 80%, 75%, 60%, 50%, 40%, 30%, 25%, 20%, 10%, 5%, or 1%, of the maximum specific growth rate.

Although specific embodiments are provided herein, the foregoing description is intended to illustrate and not limit the scope of the embodiments. Other aspects, advantages, and modifications within the scope of the embodiments will be apparent to those skilled in the art.

EXAMPLES

Unless otherwise indicated, conventional techniques of the biosynthetic industry and the like, which are within the skill of the art, may be used to practice the embodiments provided herein. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the art can deduce the correct amount in view of the remaining disclosure herein. Unless indicated otherwise, temperature is reported in degrees Celsius, and pressure is at or near atmospheric pressure at sea level. All reagents, unless otherwise indicated, were obtained commercially. The following examples are intended for illustrative purposes only and do not limit in any way the scope of the embodiments provided herein.

Example 1

This example describes methods for making vectors for the targeted integration of nucleic acids encoding enzymes including enzymes of the MEV pathway into specific chromosomal locations of *Saccharomyces cerevisiae*.

Genomic DNA was isolated from *Saccharomyces cerevisiae* strains Y002 and Y003 (CEN.PK2 background MATA or MATα ura3-52 trp1-289 leu2-3,112 his3Δ1 MAL2-8C SUC2) (van Dijken et al. (2000) *Enzyme Microb. Technol.* 26:706-714), Y007 (S288C background MATA trp1Δ63) (ATCC number 200873), and EG123 (MATA ura3 trp1 leu2 his4 can1) (Michaelis & Herskowitz. (1988) *Mol. Cell. Biol.* 8: 1309-1318). The strains were grown overnight in liquid medium containing 1% Yeast extract, 2% Bacto-peptone, and 2% Dextrose (YPD medium). Cells were isolated from 10 mL liquid cultures by centrifugation at 3,100 rpm, washing of cell pellets in 10 mL ultra-pure water, and re-centrifugation. Genomic DNA was extracted using the Y-DER yeast DNA extraction kit (Pierce Biotechnologies, Rockford, IL) as per manufacturer's suggested protocol. Extracted genomic DNA was re-suspended in 100 uL 10 mM Tris-Cl, pH 8.5, and $OD_{260/280}$ readings were taken on a ND-1000 spectrophotometer (NanoDrop Technologies, Wilmington, DE) to determine genomic DNA concentration and purity.

DNA amplification by Polymerase Chain Reaction (PCR) was done in an Applied Biosystems 2720 Thermocycler (Applied Biosystems Inc., Foster City, CA) using the Phusion High Fidelity DNA Polymerase system (Finnzymes OY, Espoo, Finland) as per manufacturer's suggested protocol. Upon completion of a PCR amplification of a DNA fragment that was to be inserted into the TOPO TA pCR2.1 cloning vector (Invitrogen, Carlsbad, CA), A nucleotide overhangs were created by adding 1 uL of Qiagen Taq Polymerase (Qiagen, Valencia, CA) to the reaction mixture and performing an additional 10 minute, 72° C. PCR extension step, followed by cooling to 4° C. Upon completion of a PCR amplification, 8 uL of a 50% glycerol solution was added to the reaction mix.

Agarose gel electrophoresis was performed using a 1% TBE (0.89 M Tris, 0.89 M boric acid, 0.02 M EDTA sodium salt) agarose gel containing 0.5 ug/mL ethidium bromide, at 120 V, 400 mA for 30 minutes. DNA bands were visualized using ultraviolet light. DNA bands were excised from the gel with a sterile razor blade, and the excised DNA was gel purified using the Zymoclean Gel DNA Recovery Kit (Zymo Research, Orange, CA) according to manufacturer's suggested protocols. The purified DNA was eluted into 10 uL ultra-pure water, and $OD_{260/280}$ readings were taken on a ND-1000 spectrophotometer to determine DNA concentration and purity.

Ligations were performed using 100-500 ug of purified PCR product and High Concentration T4 DNA Ligase (New England Biolabs, Ipswich, MA) as per manufacturer's suggested protocol. For plasmid propagation, ligated constructs were transformed into *Escherichia coli* DH5a chemically competent cells (Invitrogen, Carlsbad, CA) as per manufacturer's suggested protocol. Positive transformants were selected on solid media containing 1.5% Bacto Agar, 1% Tryptone, 0.5% Yeast Extract, 1% NaCl, and an appropriate antibiotic. Isolated transformants were grown for 16 hours in liquid Luria-Bertoni (LB) medium containing appropriate antibiotics at 37° C., and plasmid was isolated and purified using a QIAprep Spin Miniprep kit (Qiagen, Valencia, CA) as per manufacturer's suggested protocol. Constructs were verified by performing diagnostic restriction enzyme digestions, resolving DNA fragments on an agarose gel, and visualizing the bands using ultraviolet light. Select constructs were also verified by DNA sequencing, which was done by Elim Biopharmaceuticals Inc. (Hayward, CA).

Figure 4A:
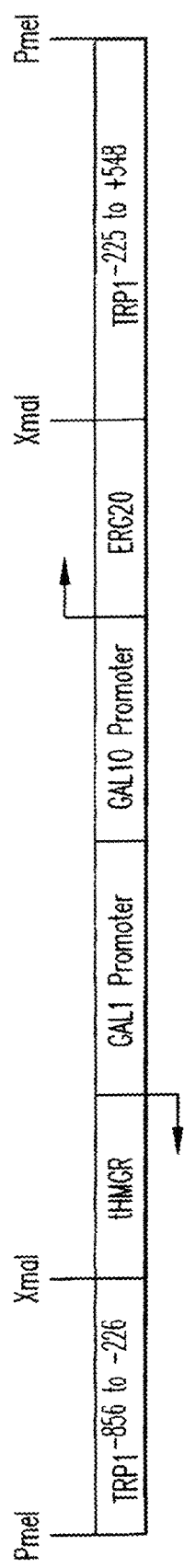

Plasmid pAM489 was generated by inserting the ERG20-$P_{GAL}$-tHMGR insert of vector pAM471 into vector pAM466. Vector pAM471 was generated by inserting DNA fragment ERG20-$P_{GAL}$-tHMGR, which comprises the open reading frame (ORF) of the ERG20 gene of *Saccharomyces cerevisiae* (ERG20 nucleotide positions 1 to 1208; A of ATG start codon is nucleotide 1) (ERG20), the genomic locus containing the divergent GAL1 and GAL10 promoter of *Saccharomyces cerevisiae* (GAL1 nucleotide position −1 to −668) ($P_{GA}$), and a truncated ORF of the HMG1 gene of *Saccharomyces cerevisiae* (HMG1 nucleotide positions 1586 to 3323) (tHMGR), into the TOPO Zero Blunt II cloning vector (Invitrogen, Carlsbad, CA). Vector pAM466 was generated by inserting DNA fragment TRP1$^{-856\ to\ +548}$ which comprises a segment of the wild-type TRP1 locus of *Saccharomyces cerevisiae* that extends from nucleotide position −856 to position 548 and harbors a non-native internal XmaI restriction site between bases −226 and −225, into the TOPO TA pCR2.1 cloning vector (Invitrogen, Carlsbad, CA). DNA fragments ERG20-$P_{GAL}$-tHMGR and TRP1$^{-856\ to\ +548}$ were generated by PCR amplification as outlined in Table 1. For the construction of pAM489, 400 ng of pAM471 and 100 ng of pAM466 were digested to completion using XmaI restriction enzyme (New England Biolabs, Ipswich, MA), DNA fragments corresponding to the ERG20-$P_{GAL}$-tHMGR insert and the linearized pAM466 vector were gel purified, and 4 molar equivalents of the purified insert was ligated with 1 molar equivalent of the purified linearized vector, yielding pAM489. FIG. 4A shows a map of the ERG20-$P_{GAL}$-tHMGR insert, and SEQ ID NO: 1 shows the nucleotide sequence of the insert with flanking TRP1 sequences.

TABLE 1

PCR amplifications performed to generate pAM489

| PCR Round | Template | Primer 1 | Primer 2 | PCR Product |
|---|---|---|---|---|
| 1 | 100 ng of Y003 genomic DNA | 61-67-CPK001-G (SEQ ID NO: 12) | 61-67-CPK002-G (SEQ ID NO: 13) | TRP1$^{-856\ to\ -226}$ |
|  |  | 61-67-CPK003-G (SEQ ID NO: 14) | 61-67-CPK004-G (SEQ ID NO: 15) | TRP1$^{-225\text{-}to\ +548}$ |
|  | 100 ng of EG123 genomic DNA | 61-67-CPK025-G (SEQ ID NO: 36) | 61-67-CPK050-G (SEQ ID NO: 44) | ERG20 |
|  | 100 ng of Y002 genomic DNA | 61-67-CPK051-G (SEQ ID NO: 45) | 61-67-CPK052-G (SEQ ID NO: 46) | PGAL |
|  |  | 61-67-CPK053-G (SEQ ID NO: 47) | 61-67-CPK031-G (SEQ ID NO: 37) | tHMGR |
| 2 | 100 ng each of TRP1$^{-856\ to\ -226}$ and TRP1$^{-225\text{-}to\ +548}$ purified PCR products | 61-67-CPK001-G (SEQ ID NO: 12) | 61-67-CPK004-G (SEQ ID NO: 15) | TRP1$^{-856\ to\ +548}$ |
|  | 100 ng each of ERG20 and $P_{GAL}$ purified PCR products | 61-67-CPK025-G (SEQ ID NO: 36) | 61-67-CPK052-G (SEQ ID NO: 46) | ERG20-PGAL |
| 3 | 100 ng each of ERG20-$P_{GAL}$ and tHMGR purified PCR products | 61-67-CPK025-G (SEQ ID NO: 36) | 61-67-CPK031-G (SEQ ID NO: 37) | ERG20-$P_{GAL}$-tHMGR |

Figure 4B:
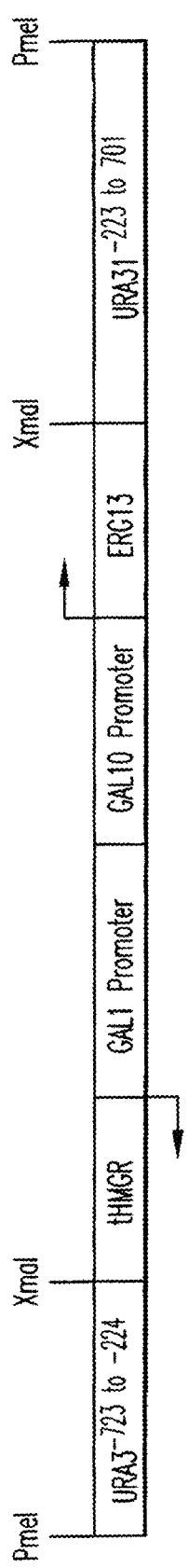

Plasmid pAM491 was generated by inserting the ERG13-$P_{GAL}$-tHMGR insert of vector pAM472 into vector pAM467. Vector pAM472 was generated by inserting DNA fragment ERG13-$P_{GAL}$-tHMGR, which comprises the ORF of the ERG13 gene of *Saccharomyces cerevisiae* (ERG13 nucleotide positions 1 to 1626) (ERG13), the genomic locus containing the divergent GAL1 and GAL10 promoter of *Saccharomyces cerevisiae* (GAL1 nucleotide position −1 to −668) ($P_{GAL}$), and a truncated ORF of the HMG1 gene of *Saccharomyces cerevisiae* (HMG1 nucleotide position 1586 to 3323) (tHMGR), into the TOPO Zero Blunt II cloning vector. Vector pAM467 was generated by inserting DNA fragment URA3$^{-723\ to\ 701}$, which comprises a segment of the wild-type URA3 locus of *Saccharomyces cerevisiae* that extends from nucleotide position −723 to position −224 and harbors a non-native internal XmaI restriction site between bases −224 and −223, into the TOPO TA pCR2.1 cloning vector. DNA fragments ERG13-$P_{GAL}$-tHMGR and URA3$^{-723\ to\ 701}$ were generated by PCR amplification as outlined in Table 2. For the construction of pAM491, 400 ng of pAM472 and 100 ng of pAM467 were digested to completion using XmaI restriction enzyme, DNA fragments corresponding to the ERG13-$P_{GAL}$-tHMGR insert and the linearized pAM467 vector were gel purified, and 4 molar equivalents of the purified insert was ligated with 1 molar equivalent of the purified linearized vector, yielding pAM491. FIG. 4B shows a map of the ERG13-$P_{GAL}$-tHMGR insert, and SEQ ID NO: 2 shows the nucleotide sequence of the insert with flanking URA3 sequences.

(tHMGR), into the TOPO Zero Blunt II cloning vector. Vector pAM468 was generated by inserting DNA fragment ADE1$^{-825\ to\ 653}$, which comprises a segment of the wild-type ADE1 locus of Saccharomyces cerevisiae that extends from nucleotide position –225 to position 653 and harbors a non-native internal XmaI restriction site between bases –226 and –225, into the TOPO TA pCR2.1 cloning vector. DNA fragments IDI1-$P_{GAL}$-tHMGR and ADE1$^{-825\ to\ 653}$ were generated by PCR amplification as outlined in Table 3. For the construction of pAM493, 400 ng of pAM473 and 100 ng

TABLE 2

PCR amplifications performed to generate pAM491

| PCR Round | Template | Primer 1 | Primer 2 | PCR Product |
|---|---|---|---|---|
| 1 | 100 ng of Y007 genomic DNA | 61-67-CPK005-G (SEQ ID NO: 16) | 61-67-CPK006-G (SEQ ID NO: 17) | URA3$^{-723\ to\ -224}$ |
| | | 61-67-CPK007-G (SEQ ID NO: 18) | 61-67-CPK008-G (SEQ ID NO: 19) | URA3$^{-223\ to\ 701}$ |
| | 100 ng of Y002 genomic DNA | 61-67-CPK032-G (SEQ ID NO: 38) | 61-67-CPK054-G (SEQ ID NO: 48) | ERG13 |
| | | 61-67-CPK052-G (SEQ ID NO: 46) | 61-67-CPK055-G (SEQ ID NO: 49) | $P_{GAL}$ |
| | | 61-67-CPK031-G (SEQ ID NO: 37) | 61-67-CPK053-G (SEQ ID NO: 47) | tHMGR |
| 2 | 100 ng each of URA3$^{-723\ to\ -224}$ and URA3$^{-223\ to\ 701}$ purified PCR products | 61-67-CPK005-G (SEQ ID NO: 16) | 61-67-CPK008-G (SEQ ID NO: 19) | URA3$^{-723\ to\ 701}$ |
| | 100 ng each of ERG13 and $P_{GAL}$ purified PCR products | 61-67-CPK032-G (SEQ ID NO: 38) | 61-67-CPK052-G (SEQ ID NO: 46) | ERG13-$P_{GAL}$ |
| 3 | 100 ng each of ERG13-$P_{GAL}$ and tHMGR purified PCR products | 61-67-CPK031-G (SEQ ID NO: 37) | 61-67-CPK032-G (SEQ ID NO: 38) | ERG13-$P_{GAL}$-tHMGR |

Figure 4C:
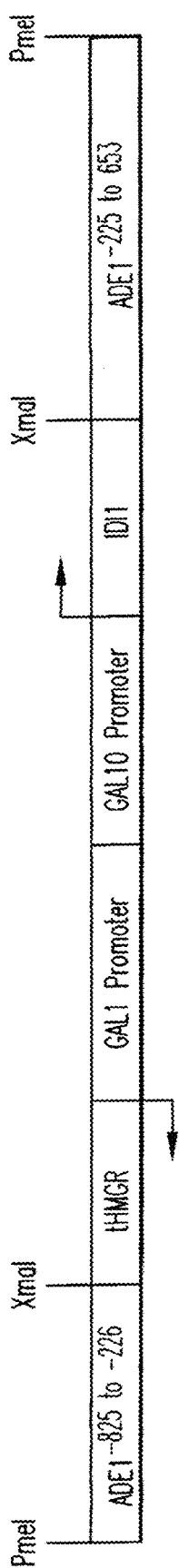

Plasmid pAM493 was generated by inserting the IDI1-$P_{GAL}$-tHMGR insert of vector pAM473 into vector pAM468. Vector pAM473 was generated by inserting DNA fragment IDI1-$P_{GAL}$-tHMGR, which comprises the ORF of the IDI1 gene of Saccharomyces cerevisiae (IDI1 nucleotide position 1 to 1017) (IDI1), the genomic locus containing the divergent GAL1 and GAL10 promoter of Saccharomyces cerevisiae (GAL1 nucleotide position –1 to –668) ($P_{GAL}$), and a truncated ORF of the HMG1 gene of Saccharomyces cerevisiae (HMG1 nucleotide positions 1586 to 3323)

of pAM468 were digested to completion using XmaI restriction enzyme, DNA fragments corresponding to the IDI1-$P_{GAL}$-tHMGR insert and the linearized pAM468 vector were gel purified, and 4 molar equivalents of the purified insert was ligated with 1 molar equivalent of the purified linearized vector, yielding vector pAM493. FIG. 4C shows a map of the IDI1-$P_{GAL}$-tHMGR insert, and SEQ ID NO: 3 shows the nucleotide sequence of the insert with flanking ADE1 sequences.

TABLE 3

PCR amplifications performed to generate pAM493

| PCR Round | Template | Primer 1 | Primer 2 | PCR Product |
|---|---|---|---|---|
| 1 | 100 ng of Y007 genomic DNA | 61-67-CPK009-G (SEQ ID NO: 20) | 61-67-CPK010-G (SEQ ID NO: 21) | ADE1$^{-825\ to\ -226}$ |
| | | 61-67-CPK011-G (SEQ ID NO: 22) | 61-67-CPK012-G (SEQ ID NO: 23) | ADE1$^{-225\ to\ 653}$ |
| | 100 ng of Y002 genomic DNA | 61-67-CPK047-G (SEQ ID NO: 43) | 61-67-CPK064-G (SEQ ID NO: 58) | IDI1 |
| | | 61-67-CPK052-G (SEQ ID NO: 46) | 61-67-CPK065-G (SEQ ID NO: 59) | $P_{GAL}$ |
| | | 61-67-CPK031-G (SEQ ID NO: 37) | 61-67-CPK053-G (SEQ ID NO: 47) | tHMGR |
| 2 | 100 ng each of ADE1$^{-825\ to\ -226}$ and ADE1$^{-225\ to\ 653}$ purified PCR products | 61-67-CPK009-G (SEQ ID NO: 20) | 61-67-CPK012-G (SEQ ID NO: 23) | ADE1$^{-825\ to\ 653}$ |
| | 100 ng each of IDI1 and $P_{GAL}$ purified PCR products | 61-67-CPK047-G (SEQ ID NO: 43) | 61-67-CPK052-G (SEQ ID NO: 46) | IDI1-$P_{GAL}$ |
| 3 | 100 ng each of IDI1-$P_{GAL}$ and tHMGR purified PCR products | 61-67-CPK031-G (SEQ ID NO: 37) | 61-67-CPK047-G (SEQ ID NO: 43) | IDI1-$P_{GAL}$-tHMGR |

Plasmid pAM495 was generated by inserting the ERG10-$P_{GAL}$-ERG12 insert of pAM474 into vector pAM469. Vector pAM474 was generated by inserting DNA fragment ERG10-$P_{GAL}$-ERG12, which comprises the ORF of the ERG10 gene of *Saccharomyces cerevisiae* (ERG10 nucleotide position 1 to 1347) (ERG10), the genomic locus containing the divergent GAL1 and GAL10 promoter of *Saccharomyces cerevisiae* (GAL1 nucleotide position −1 to −668) ($P_{GAL}$), and the ORF of the ERG12 gene of *Saccharomyces cerevisiae* (ERG12 nucleotide position 1 to 1482) (ERG12), into the TOPO Zero Blunt II cloning vector. Vector pAM469 was generated by inserting DNA fragment HIS3$^{-32\ to\ -1000}$-HISMX-HIS3$^{504\ to\ -1103}$, which comprises two segments of the HIS locus of *Saccharomyces cerevisiae* that extend from nucleotide position −32 to position −1000 and from nucleotide position 504 to position 1103, a HISMX marker, and a non-native XmaI restriction site between the HIS3$^{504\ to\ -1103}$ sequence and the HISMX marker, into the TOPO TA pCR2.1 cloning vector. DNA fragments ERG10-$P_{GAL}$-ERG12 and HIS3$^{-32\ to\ -1000}$-HISMX-HIS3$^{504\ to\ -1103}$ were generated by PCR amplification as outlined in Table 4. For construction of pAM495, 400 ng of pAM474 and 100 ng of pAM469 were digested to completion using XmaI restriction enzyme, DNA fragments corresponding to the ERG10-$P_{GAL}$-ERG12 insert and the linearized pAM469 vector were gel purified, and 4 molar equivalents of the purified insert was ligated with 1 molar equivalent of the purified linearized vector, yielding vector pAM495. FIG. 4D shows a map of the ERG10-$P_{GAL}$-ERG12 insert, and SEQ ID NO: 4 shows the nucleotide sequence of the insert with flanking HIS3 sequences.

Plasmid pAM497 was generated by inserting the ERG8-$P_{GAL}$-ERG19 insert of pAM475 into vector pAM470. Vector pAM475 was generated by inserting DNA fragment ERG8-$P_{GAL}$-ERG19, which comprises the ORE of the ERG8 gene of *Saccharomyces cerevisiae* (ERG8 nucleotide position 1 to 1512) (ERG8), the genomic locus containing the divergent GAL1 and GAL10 promoter of *Saccharomyces cerevisiae* (GAL1 nucleotide position −1 to −668) ($P_{GAL}$), and the ORE of the ERG19 gene of *Saccharomyces cerevisiae* (ERG19 nucleotide position 1 to 1341) (ERG19), into the TOPO Zero Blunt 11 cloning vector. Vector pAM470 was generated by inserting DNA fragment LEU2$^{-100\ to\ 450}$HISMX-LEU2$^{1096\ to\ 1770}$ which comprises two segments of the LEU2 locus of *Saccharomyces cerevisiae* that extend from nucleotide position −100 to position 450 and from nucleotide position 1096 to position 1770, a HISMX marker, and a non-native XmaI restriction site between the LEU2$^{1096\ to\ 1770}$ sequence and the HISMX marker, into the TOPO TA pCR2.1 cloning vector. DNA fragments ERG8-$P_{GAL}$-ERG19 and LEU2$^{-100\ to\ 450}$-HISMX-LEU2$^{1096\ to\ 1770}$ were generated by PCR amplification as outlined in Table 5. For the construction of pAM497, 400 ng of pAM475 and 100 ng of pAM470 were digested to completion using XmaI restriction enzyme, DNA fragments corresponding to the ERG8-$P_{GAL}$-ERG19 insert and the linearized pAM470 vector were purified, and 4 molar equivalents of the purified insert was ligated with 1 molar equivalent of the purified linearized vector, yielding vector pAM497. FIG. 4E for a map of the ERG8-$P_{GAL}$-ERG19 insert, and SEQ ID NO: 5 shows the nucleotide sequence of the insert with flanking LEU2 sequences.

TABLE 4

PCR reactions performed to generate pAM495

| PCR Round | Template | Primer 1 | Primer 2 | PCR Product |
|---|---|---|---|---|
| 1 | 100 ng of Y007 genomic DNA | 61-67-CPK013-G (SEQ ID NO: 24) | 61-67-CPK014alt-G (SEQ ID NO: 25) | HIS3$^{-32\ to\ -1000}$ |
| | | 61-67-CPK017-G (SEQ ID NO: 28) | 61-67-CPK018-G (SEQ ID NO: 29) | HIS3$^{504\ to\ -1103}$ |
| | | 61-67-CPK035-G (SEQ ID NO: 39) | 61-67-CPK056-G (SEQ ID NO: 50) | ERG10 |
| | | 61-67-CPK057-G (SEQ ID NO: 51) | 61-67-CPK058-G (SEQ ID NO: 52) | $P_{GAL}$ |
| | | 61-67-CPK040-G (SEQ ID NO: 40) | 61-67-CPK059-G (SEQ ID NO: 53) | ERG12 |
| | 10 ng of plasmid pAM330 DNA ** | 61-67-CPK015alt-G (SEQ ID NO: 26) | 61-67-CPK016-G (SEQ ID NO: 27) | HISMX |
| 2 | 100 ng each of HIS3$^{504\ to\ -1103}$ and HISMX PCR purified products | 61-67-CPK015alt-G (SEQ ID NO: 26) | 61-67-CPK018-G (SEQ ID NO: 29) | HISMX-HIS3$^{504\ to\ -1103}$ |
| | 100 ng each of ERG10 and $P_{GAL}$ purified PCR products | 61-67-CPK035-G (SEQ ID NO: 39) | 61-67-CPK058-G (SEQ ID NO: 52) | ERG10-$P_{GAL}$ |
| 3 | 100 ng each of HIS3$^{-32\ to\ -1000}$ and HISMX-HIS3$^{504\ to\ -1103}$ purified PCR products | 61-67-CPK013-G (SEQ ID NO: 24) | 61-67-CPK018-G (SEQ ID NO: 29) | HIS3$^{-32\ to\ -1000}$-HISMX-HIS3$^{504\ to\ -1103}$ |
| | 100 ng each of ERG10-$P_{GAL}$ and ERG12 purified PCR products | 61-67-CPK035-G (SEQ ID NO: 39) | 61-67-CPK040-G (SEQ ID NO: 40) | ERG10-$P_{GAL}$-ERG12 |

** The HISMX marker in pAM330 originated from pFA6a-HISMX6-PGAL1 as described by van Dijken et al. ((2000) Enzyme Microb. Technol. 26(9-10):706-714).

TABLE 5

PCR reactions performed to generate pAM497

| PCR Round | Template | Primer 1 | Primer 2 | PCR Product |
|---|---|---|---|---|
| 1 | 100 ng of Y007 genomic DNA | 61-67-CPK019-G (SEQ ID NO: 30) | 61-67-CPK020-G (SEQ ID NO: 31) | LEU2$^{-100\ to\ 450}$ |
| | | 61-67-CPK023-G (SEQ ID NO: 34) | 61-67-CPK024-G (SEQ ID NO: 35) | LEU2$^{1096\ to\ 1770}$ |
| | 10 ng of plasmid pAM330 DNA ** | 61-67-CPK021-G (SEQ ID NO: 32) | 61-67-CPK022-G (SEQ ID NO: 33) | HISMX |
| | 100 ng of Y002 genomic DNA | 61-67-CPK041-G (SEQ ID NO: 41) | 61-67-CPK060-G (SEQ ID NO: 54) | ERG8 |
| | | 61-67-CPK061-G (SEQ ID NO: 55) | 61-67-CPK062-G (SEQ ID NO: 56) | P$_{GAL}$ |
| | | 61-67-CPK046-G (SEQ ID NO: 42) | 61-67-CPK063-G (SEQ ID NO: 57) | ERG19 |
| 2 | 100 ng each of LEU2$^{1096\ to\ 1770}$ and HISMX purified PCR products | 61-67-CPK021-G (SEQ ID NO: 32) | 61-67-CPK024-G (SEQ ID NO: 35) | HISMX-LEU2$^{1096\ to\ 1770}$ |
| | 100 ng each of ERG8 and P$_{GAL}$ purified PCR products | 61-67-CPK041-G (SEQ ID NO: 41) | 61-67-CPK062-G (SEQ ID NO: 56) | ERG8-P$_{GAL}$ |
| 3 | 100 ng of LEU2$^{-100\ to\ 450}$ and HISMX-LEU2$^{1096\ to\ 1770}$ purified PCR products | 61-67-CPK019-G (SEQ ID NO: 30) | 61-67-CPK024-G (SEQ ID NO: 35) | LEU2$^{-100\ to\ 450}$-HISMX-LEU2$^{1096\ to\ 1770}$ |
| | 100 ng each of ERG8-P$_{GAL}$ and ERG19 purified PCR products | 61-67-CPK041-G (SEQ ID NO: 41) | 61-67-CPK046-G (SEQ ID NO: 42) | ERG8-P$_{GAL}$-ERG19 |

** The HISMX marker in pAM330 originated from pFA6a-HISMX6-PGAL1 as described by van Dijken et al. ((2000) Enzyme Microb. Technol. 26(9-10):706-714).

Example 2

This example describes methods for making plasmids and DNA fragments useful in the embodiments provided herein.

Plasmid pAM584 was generated by inserting DNA fragment GAL7$^{4\ to\ 1021}$-HPH-GAL1$^{1637\ to\ 2587}$ into the TOPO ZERO Blunt II cloning vector (Invitrogen, Carlsbad, CA). DNA fragment GAL7$^{4\ to\ 1021}$HPH-GAL1$^{1637\ to\ 2587}$ comprises a segment of the ORF of the GAL7 gene of Saccharomyces cerevisae (GAL7 nucleotide positions 4 to 1021) (GAL7$^{4\ to\ 1021}$) the hygromycin resistance cassette (HPH), and a segment of the 3' untranslated region (UTR) of the GAL1 gene of Saccharomyces cerevisiae (GAL1 nucleotide positions 1637 to 2587). The DNA fragment was generated by PCR amplification as outlined in Table 6. FIG. 4F shows a map and SEQ ID NO: 9 the nucleotide sequence of DNA fragment GAL7$^{4\ to\ 1021}$-HPH-GAL1$^{1637\ to\ 2587}$.

DNA fragment GAL80$^{-50\ to\ -1}$-NatR-GAL80$^{1309\ to\ 1358}$ was generated by PCR amplification. The DNA fragments includes the nourseothricin resistance selectable marker gene of Streptomyces noursei (NatR) flanked by two segments of 50 nucleotides each that map immediately upstream and immediately downstream of the coding region of the GAL80 gene of Saccharomyces cerevisiae (GAL80 nucleotide position -50 to -1 and 1309 to 1358; GAL80$^{-50\ to\ -1}$ and GAL80$^{1309\ to\ 1358}$ respectively). FIG. 4F shows a map, and SEQ ID NO: 8 the nucleotide sequence, of DNA fragment GAL80$^{-50\ to\ -1}$-NatR-GAL80$^{1309\ to\ 1358}$.

DNA fragment GAL1$^{1\ to\ 48}$-NatR-GAL1$^{1500\ to\ 1550}$ was generated by PCR amplification. The DNA fragment includes the nourseothricin resistance selectable marker gene of Streptomyces noursei (NatR) flanked by two segments of 40 to 50 nucleotides each that map to the 5' and the 3' end of the coding region of the GAL1 gene of Saccharomyces cerevisiae (GAL1 nucleotide position 1 to 48 and 1500 to 1550; GAL1$^{1\ to\ 48}$ and GAL1$^{1500\ to\ 1550}$, respec-

TABLE 6

PCR reactions performed to generate pAM584

| PCR Round | Template | Primer 1 | Primer 2 | PCR Product |
|---|---|---|---|---|
| 1 | 100 ng of Y002 genomic DNA | 91-014-CPK236-G (SEQ ID NO: 65) | 91-014-CPK237-G (SEQ ID NO: 66) | GAL7$^{4\ to\ 1021}$ |
| | | 91-014-CPK232-G (SEQ ID NO: 63) | 91-014-CPK233-G (SEQ ID NO: 64) | GAL1$^{1637\ to\ 2587}$ |
| | 10 ng of plasmid pAM547 DNA ** | 91-014-CPK231-G (SEQ ID NO: 62) | 91-014-CPK238-G (SEQ ID NO: 67) | HPH |
| 2 | 100 ng each of GAL7$^{4\ to\ 1021}$ and HPH purified PCR products | 91-014-CPK231-G (SEQ ID NO: 62) | 91-014-CPK236-G (SEQ ID NO: 65) | GAL7$^{4\ to\ 1021}$-HPH |
| 3 | 100 ng of each GAL1$^{1637\ to\ 2587}$ and GAL7$^{4\ to\ 1021}$-HPH purified PCR products | 91-014-CPK233-G (SEQ ID NO: 64) | 91-014-CPK236-G (SEQ ID NO: 65) | GAL7$^{4\ to\ 1021}$-HPH-GAL1$^{1637\ to\ 2587}$ |

** Plasmid pAM547 was generated synthetically, and comprises the HPH cassette, which consists of the coding sequence for the hygromycin B phosphotransferase of Escherichia coli flanked by the promoter and terminator of the Tef1 gene of Kluyveromyces lactis.

tively). FIG. 4G shows a map, and SEQ ID NO: 68 the nucleotide sequence of DNA fragment GAL1$^{1\ to\ 48}$-NatR-GAL1$^{1500\ to\ 1550}$.

Expression plasmid pAM353 was generated by inserting a nucleotide sequence encoding a β-farnesene synthase into the pRS425-Gal1 vector (Mumberg et. al. (1994) *Nucl. Acids. Res.* 22(25): 5767-5768). The nucleotide sequence insert was generated synthetically, using as a template the coding sequence of the β-farnesene synthase gene of *Artemisia annua* (GenBank accession number AY835398) codon-optimized for expression in *Saccharomyces cerevisiae* (SEQ ID NO: 10). The synthetically generated nucleotide sequence was flanked by 5' BamHI and 3' XhoI restriction sites, and could thus be cloned into compatible restriction sites of a cloning vector such as a standard pUC or pACYC origin vector. The synthetically generated nucleotide sequence was isolated by digesting to completion the DNA synthesis construct using BamHI and XhoI restriction enzymes. The reaction mixture was resolved by gel electrophoresis, the approximately 1.7 kb DNA fragment comprising the β-farnesene synthase coding sequence was gel extracted, and the isolated DNA fragment was ligated into the BamHI XhoI restriction site of the pRS425-Gal1 vector, yielding expression plasmid pAM353.

Figure 5:
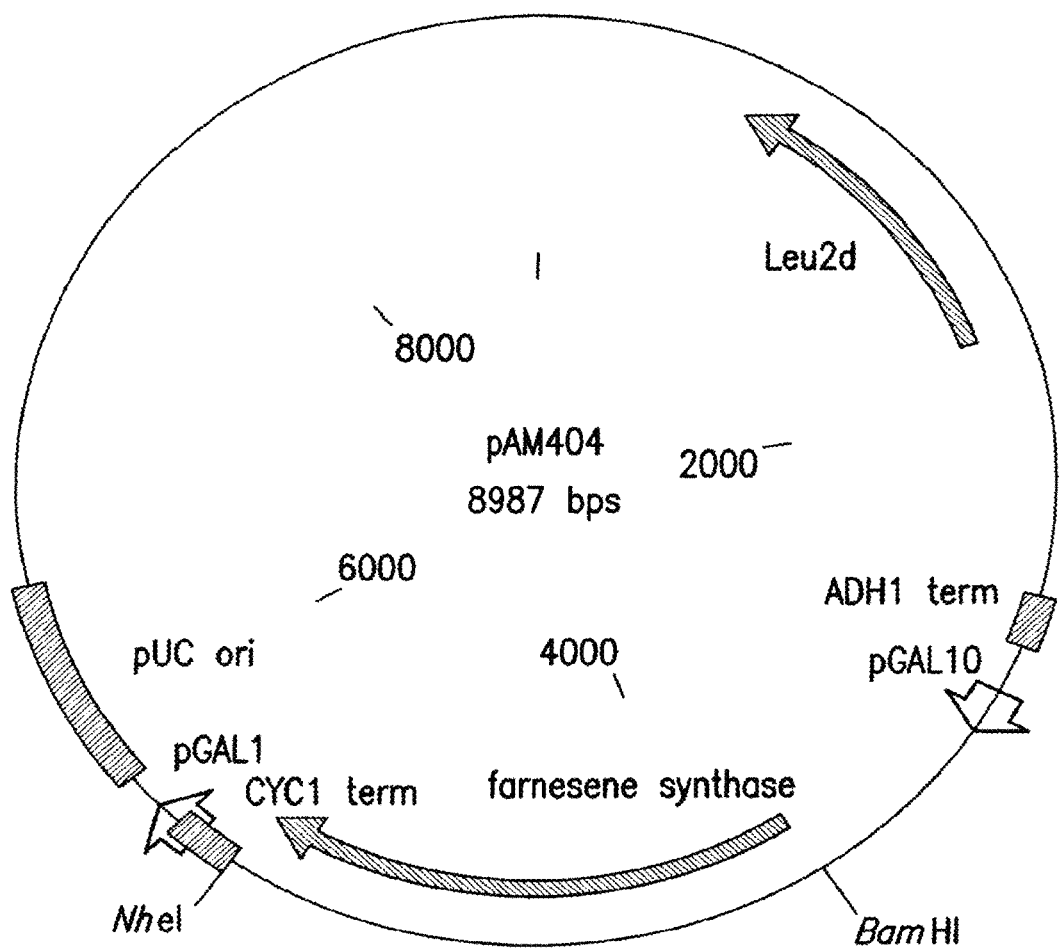
FIG. 5 shows a map of plasmid pAM404.

Expression plasmid pAM404 was generated by inserting a nucleotide sequence encoding the 0-farnesene synthase of *Artemisia annua*, codon-optimized for expression in *Saccharomyces cerevisiae*, into vector pAM178 (SEQ ID NO: 69). The nucleotide sequence encoding the β-farnesene synthase was PCR amplified from pAM353 using primers 52-84 pAM326 BamHI (SEQ ID NO: 71) and 52-84 pAM326 NheI (SEQ ID NO: 72). The resulting PCR product was digested to completion using BamHI and NheI restriction enzymes, the reaction mixture was resolved by gel electrophoresis, the approximately 1.7 kb DNA fragment comprising the β-farnesene synthase coding sequence was gel extracted, and the isolated DNA fragment was ligated into the BamHI NheI restriction site of vector pAM178, yielding expression plasmid pAM404 (see FIG. 5 for a plasmid map).

Example 3

This example describes the generation of *Saccharomyces cerevisiae* strains useful in the embodiments provided herein.

*Saccharomyces cerevisiae* strains CEN.PK2-1C Y002 and Y003 (MATA or MATalpha; ura3-52; trp1-289; leu2-3,112; his3Δ1; MAL2-8C; SUC2) (van Dijken et al. (2000) *Enzyme Microb. Technol.* 26(9-10):706-714) were prepared for introduction of inducible MEV pathway genes by replacing the ERG9 promoter with the *Saccharomyces cerevisiae* MET3 promoter, and the ADE1 ORF with the *Candida glabrata* LEU2 gene (CgLEU2). This was done by PCR amplifying the KanMX-$P_{MET3}$ region of vector pAM328 (SEQ ID NO: 6), which comprises the $P_{MET3}$ promoter preceded by the kanamycin resistance marker flanked by the promoter and terminator of the Tef1 gene of *Kluyveromyces lactis*, using primers 50-56-pw100-G (SEQ ID NO: 10) and 50-56-pw101-G (SEQ ID NO: 11), which include 45 base pairs of homology to the native ERG9 promoter, transforming 10 ug of the resulting PCR product into exponentially growing Y002 and Y003 cells using 40% w/w Polyethelene Glycol 3350 (Sigma-Aldrich, St. Louis, MO), 100 mM Lithium Acetate (Sigma-Aldrich, St. Louis, MO), and 10 ug Salmon Sperm DNA (Invitrogen Corp., Carlsbad, CA), and incubating the cells at 30° C. for 30 minutes followed by heat shocking them at 42° C. for 30 minutes (Schiestl and Gietz (1989) *Curr. Genet.* 16:339-346). Positive recombinants were identified by their ability to grow on rich medium containing 0.5 ug/mL Geneticin (Invitrogen Corp., Carlsbad, CA), and selected colonies were confirmed by diagnostic PCR. The resultant clones were given the designation Y93 (MAT A) and Y94 (MAT alpha). The 3.5 kb CgLEU2 genomic locus was then amplified from *Candida glabrata* genomic DNA (ATCC, Manassas, VA) using primers 61-67-CPK066-G (SEQ ID NO: 60) and 61-67-CPK067-G (SEQ ID NO: 61), which contain 50 base pairs of flanking homology to the ADE1 ORF, and 10 ug of the resulting PCR product were transformed into exponentially growing Y93 and Y94 cells, positive recombinants were selected for growth in the absence of leucine supplementation, and selected clones were confirmed by diagnostic PCR. The resultant clones were given the designation Y176 (MAT A) and Y177 (MAT alpha).

Strain Y188 was generated by digesting pAM491 and pAM495 plasmid DNA to completion using PmeI restriction enzyme (New England Biolabs, Beverly, MA), and introducing the purified DNA inserts into exponentially growing Y176 cells. Positive recombinants were selected for by growth on medium lacking uracil and histidine, and integration into the correct genomic locus was confirmed by diagnostic PCR.

Strain Y189 was generated by digesting pAM489 and pAM497 plasmid DNA to completion using PmeI restriction enzyme, and introducing the purified DNA inserts into exponentially growing Y177 cells. Positive recombinants were selected for by growth on medium lacking tryptophan and histidine, and integration into the correct genomic locus was confirmed by diagnostic PCR.

Approximately $1 \times 10^7$ cells from strains Y188 and Y189 were mixed on a YPD medium plate for 6 hours at room temperature to allow for mating. The mixed cell culture was plated to medium lacking histidine, uracil, and tryptophan to select for growth of diploid cells. Strain Y238 was generated by transforming the diploid cells using pAM493 plasmid DNA that had been digested to completion using PmeI restriction enzyme, and introducing the purified DNA insert into the exponentially growing diploid cells. Positive recombinants were selected for by growth on medium lacking adenine, and integration into the correct genomic locus was confirmed by diagnostic PCR.

Haploid strain Y211 (MAT alpha) was generated by sporulating strain Y238 in 2% potassium acetate and 0.02% Raffinose liquid medium, isolating approximately 200 genetic tetrads using a Singer Instruments MSM300 series micromanipulator (Singer Instrument LTD, Somerset, UK), identifying independent genetic isolates containing the appropriate complement of introduced genetic material by their ability to grow in the absence of adenine, histidine, uracil, and tryptophan, and confirming the integration of all introduced DNA by diagnostic PCR.

Strain Y227 was generated from strain Y211 by rendering the strain capable of converting FPP to amorpha-4,11-diene. To this end, exponentially growing Y211 cells were transformed with expression plasmid pAM426 (SEQ ID NO: 7), which comprises a GAL1 promoter operably linked to the coding sequence of an amorpha-4,11-diene synthase gene that is codon-optimized for expression in *Saccharomyces cerevisiae* (Merke et al. (2000) *Ach. Biochem. Biophys.* 381:173-180). Host cell transformants were selected on complete synthetic defined media lacking leucine.

Strain Y293 was generated from strain Y227 by deleting the coding sequence of the GAL80 gene, and thus rendering the GAL promoters in the strain constitutively active. To this end, exponentially growing Y227 cells were transformed with DNA fragment GAL80$^{-50\ to\ -1}$-NatR-GAL80$^{1309\ to\ 1358}$ Host cell transformants were selected on YPD agar containing 100 µg/ml nourseothricin, single colonies were picked, and integration into the correct genomic locus was confirmed by diagnostic PCR.

Strain Y337 was generated from strain Y227 by rendering the strain unable to catabolize galactose. To this end, pAM584 plasmid DNA was digested to completion using PmeI restriction enzyme, and the purified DNA insert GAL7$^{4\ to\ 1021}$-HPH-GAL1$^{1637\ to\ 2587}$ was introduced into exponentially growing Y227 cells. Positive recombinants were selected for by growth on YPD agar containing hygromycin B (Sigma, St. Louis, MO). Integration into the correct genomic locus was confirmed by diagnostic PCR and by testing the strain for inability to use galactose as a carbon source.

Strain Y351 was generated from strain Y211 by rendering the strain unable to catabolize galactose. To this end, pAM584 plasmid DNA was digested to completion using PmeI restriction enzyme, and the purified DNA insert GAL7$^{4\ to\ 1021}$-HPH-GAL1$^{1637\ to\ 2587}$ was introduced into exponentially growing Y211. Host cell transformants were selected on YPD agar containing hygromycin B. Integration into the correct genomic locus was confirmed by diagnostic PCR and by testing the strain for inability to use galactose as a carbon source.

Strain Y352 was generated from strain Y351 by rendering the strain able to produce β-farnesene synthase. To this end, exponentially growing Y351 cells were transformed with expression plasmid pAM404. Host cell transformants were selected on complete synthetic defined media lacking leucine.

Strain Y283 was generated from strain Y227 by deleting the coding sequence of the GAL1 gene and thus rendering the strain unable to catabolize galactose. To this end, exponentially growing Y227 cells were transformed with DNA fragment GAL1$^{1\ to\ 48}$-NatR-GAL1$^{1500\ to\ 1550}$ Host cell transformants were selected on YPD agar containing 100 µg/mL nourseothricin, single colonies were picked, and integration into the correct genomic locus was confirmed by diagnostic PCR and by growing the strain on agar containing glycerol and 2-deoxygalactose (a functional GAL1p would convert the latter into a toxin).

Strain Y221 was generated from strain Y211 by transforming exponentially growing Y211 cells with vector pAM178 (SEQ ID NO: 69). Positive transformants were selected for by growth on complete synthetic medium lacking leucine.

Strain Y290 was generated from strain Y221 by deleting the coding sequence of the GAL80 gene, and thus rendering the GAL promoters in the strain constitutively active.

Strain Y318 was generated from strain Y290 by screening colonies for loss of the pAM178 vector.

Strain 409 was generated from strain Y318 by rendering the strain able to produce β-farnesene synthase in the presence of galactose. To this end, exponentially growing Y318 cells were transformed with expression plasmid pAM404. Host cell transformants were selected on complete synthetic defined media lacking leucine.

Strain Y419 was generated from strain Y409 by rendering the GAL promoters in the strain constitutively active and able to express higher levels of GAL4p in the presence of glucose (i.e., able to more efficiently drive expression off galactose-inducible promoters in the presence of glucose, as well as assure that there is enough Gal4p transcription factor to drive expression from all the galactose-inducible promoters in the cell). To this end, the KanMX marker at the ERG9 locus in strain Y409 was replaced by a DNA fragment that comprised the ORF of the GAL4 gene of *Saccharomyces cerevisiae* under the control of an "operative constitutive" version of its native promoter (Griggs & Johnston (1991) *PNAS* 88(19):8597-8601) and the GAL4 terminator (P$_{Gal4OC}$-GAL4-T$_{GAL4}$), and the nourseothricin resistance selectable marker gene of *Streptomyces noursei* (NatR) flanked by the promoter and terminator of the Tef1 gene of *Kluyveromyces lactis*.

Strain Y677 was generated from strain Y419 by introducing another copy of the coding region of mevalonate kinase under the control of P$_{GAL}$1 at the GAL80 locus.

Cell banks of strains Y293, Y283, Y352 and Y677 were prepared by growing the cells in seed medium at 30° C. until they reached an OD$_{600}$ of between 2 to 5. At that time, the flasks were placed on ice. Three parts culture and 2 parts ice cold sterile 50% glycerol were combined, and 1 mL aliquots of this mixture were frozen at −80° C. in cyrovials. The same procedure was used for strain Y337, however the OD$_{600}$ for that strain was 13.6 at the time it was frozen.

Example 4

This example describes the production of amorpha-4,11-diene by host cells in fed batch, carbon-restricted fermentation with a glucose only feed.

Y337 seed cultures were prepared by inoculating a 1 mL frozen vial into a 250 mL flask containing 50 mL seed medium (Table 7). After ~24 hours of growth at 30° C., 0.5 mL of the culture was sub-cultured into additional 250 mL flasks each containing 50 mL seed medium. The seed cultures were grown at 30° C. overnight to an OD$_{600}$ of approximately 3 to 12. Flasks were pooled and used to inoculate bioreactors containing batch medium (Table 8) at 10% v/v.

TABLE 7

| Seed medium | |
|---|---|
| Component | Seed Medium |
| tap water (mL/L) | 350 |
| 2x batch base (mL/L) $^{a)}$ | 500 |
| 715 g/L glucose monohydrate (mL/L) $^{b)}$ | 30 |
| Yeast vitamin solution (mL/L) (Table 9) | 12 |
| Yeast trace metals solution (mL/L) (Table 9) | 10 |
| succinate (0.5M, pH 5.0) (mL/L) $^{c)}$ | 100 |

$^{a)}$ 16 g/L KH$_2$PO$_4$, 30 g/L (NH$_4$)$_2$SO$_4$, and 12.3 g/L MgSO$_4$*7H$_2$O (Note: no heating while mixing these components)
$^{b)}$ The glucose monohydrate stock solution was prepared by dissolving the sugar in water with heating, allowing the solution to cool, and filter sterilizing.
$^{c)}$ The succinate stock solution was prepared by dissolving succinic acid in water with heating, letting the solution cool, adjusting the pH to 5.05 with NaOH, and sterilizing the solution by autoclaving (45 minutes at 121° C.).

TABLE 8

| Bioreactor batch medium | |
|---|---|
| Component | Batch Medium |
| tap water (mL/L) | 350 |
| 2x batch base (mL/L) (Table 7) | 500 |
| glucose (g/L) | 19.5 |
| Yeast vitamin solution (mL/L) (Table 9) | 12 |
| Yeast trace metals solution (mL/L) (Table 9) | 10 |

Batch medium was prepared by combining 2x batch base with tap water in a 2L bioreactor, autoclaving the unit, and in a sterile hood bringing the volume of the solution to 90% of final by adding concentrated filter-sterilized stock solutions of sugar, vitamins, and trace metals. The remaining 10% of starting volume was from the seed culture.

TABLE 9

Vitamin and trace metals stock solutions

| Component | Yeast vitamin solution (g/L) [a] |
|---|---|
| Biotin | 0.05 |
| calcium pantothenate | 1 |
| nicotinic acid | 1 |
| Myoinositol | 25 |
| thiamine HCl | 1 |
| pyridoxol HCl | 1 |
| p-aminobenzoic acid | 0.2 |

| Component | Yeast trace metals solution (g/L) [b] |
|---|---|
| $ZnSO_4 \cdot 7H_2O$ | 5.75 |
| $MnCl_2 \cdot 4H_2O$ | 0.32 |
| $CuSO_4$ anhydrous | 0.32 |
| $CoCl_2 \cdot 6H_2O$ | 0.47 |
| $Na_2MoO_4 \cdot 2H_2O$ | 0.48 |
| $CaCl_2 \cdot 2H_2O$ | 2.9 |
| $FeSO_4 \cdot 7H_2O$ | 2.8 |
| 0.5M EDTA | 80 (mL/L) |

[a] Biotin was first dissolved in 10 mL of 5M NaOH, and then added to DI water (750 mL/L). The pH was adjusted to 6.5 using 5M NaOH or HCl, and again adjusted after the addition of each vitamin. After all vitamins were dissolved, the solution was brought to final volume with DI water, and filter sterilized. The bottle was covered in aluminum foil and stored at 4° C.
[b] EDTA was first added to DI water (750 mL/L) before the $ZnSO_4$ was dissolved. The pH was adjusted to 6.0 using 5M NaOH, and again adjusted after the addition of each metal. After all metals were dissolved, the pH was adjusted to 4.0 using 5M HCl, and the solution was brought to the final volume with DI water, and filter sterilized. The bottle was covered in aluminum foil and stored at 4° C.

The pH of the fermentation was controlled automatically and maintained at pH 5 with the addition of 10 N $NH_4OH$. Temperature was maintained at 30° C. Airflow was supplied at a rate of 1 LPM. Dissolved oxygen was maintained at 40% with an agitation cascade followed by oxygen enrichment. Foam was controlled with Biospumex antifoam 200 K.

The bioreactor culture was allowed to grow until glucose in the batch medium was depleted, at which point, an exponential glucose feed was initiated for which glucose feed medium (Table 10) was pumped into the bioreactor at the rate defined by the following equations:

$$F = V \mu_{set} S_B e^{\mu_{set}(t-t_0)}$$

$$V = V_0 + V_{feed}$$

F is the substrate mass flow rate (g/hr), V is the liquid volume in the bioreactor at a given time (L), $S_B$ is the concentration of substrate in the batch media (20 g/L), $\mu_{set}$ is the specific feed rate (0.087 hr$^{-1}$), t is the batch age (hr), $t_0$ is the batch age when the feed was initiated (hr), $V_0$ is the initial volume in the bioreactor, and $V_{feed}$ is the total volume of feed added to the bioreactor at a given time (L). The exponential feed phase continued until the ratio of F/V reached a preset maximum feed rate (Table 11). After reaching this maximum, the ratio of F/V was maintained constant for the remainder of the process at a preset stationary feed rate (Table 11).

TABLE 10

Bioreactor feed media

| Component | Glucose Feed Medium [a] | Mixed Feed Medium [b] |
|---|---|---|
| Base Medium | | |
| glucose monohydrate (g/L) [a] | 650 | 425 |
| $KH_2PO_4$ (g/L) | 9 | 9 |
| $MgSO_4 \cdot 7H2O$ (g/L) | 5.12 | 5.12 |
| $K_2SO_4$ (g/L) | 3.5 | 3.5 |
| $Na_2SO_4$ (g/L) | 0.28 | 0.28 |
| Supplmentary Components | | |
| Yeast vitamin solution (mL/L) (Table 9) | 12 | 12 |
| Yeast trace metals solution (mL/L) (Table 9) | 10 | 10 |
| 95% (v/v) ethanol (mL/L) | 0 | 237 |

[a] Glucose feed medium was prepared by mixing glucose monohydrate, $KH_2PO_4$, $MgSO_4 \cdot 7H2O$, $K_2SO_4$, and $Na_2SO_4$ in 38° C. tap water, cooling the solution, filter sterilizing, adding the supplementary components (concentrated filter-sterilized stock solutions of trace metals and vitamins) in a sterile hood, and bringing the solution to final volume by adding sterile water.
[b] Mixed feed medium was prepared by mixing glucose, $KH_2PO_4$, $MgSO_4 \cdot 7H2O$, $K_2SO_4$, and $Na_2SO_4$ in 300 mL of 38° C. tap water, heating the mixture to approximately 100° C. to fully dissolve the sugar and salts, adding water to bring the volume to 750 mL, cooling the solution, filter sterilizing using a 0.2 micron filter, adding first 237 mL of 95% (v/v) ethanol and adding the supplementary components (concentrated filter-sterilized stock solutions of trace metals and vitamins) in a sterile hood, and bringing the solution to the final volume of 1 L by adding sterile water.

Production of amorpha-4,11-diene was induced at an $OD_{600}$ of 50 about 24 hours after inoculation with the addition of 10 g/L galactose to the bioreactor and feed bottle (22.2 mL of a 450 g/L galactose stock solution per liter culture volume). In addition, 0.25 g/L methionine was added to the bioreactor and 1 g/L methionine was added to the feed bottle to repress transcription of the ERG9 gene (10 mL of a 25 g/L methionine stock solution per liter culture volume and 40 mL of a 25 g/L methionine stock solution per liter feed volume), and 10% v/v of autoclaved methyl oleate was added to the bioreactor to capture the amorpha-4,11-diene. (The 450 g/L galactose stock solution was prepared by dissolving the sugar in water with heating, allowing the solution to cool, and filter sterilizing. The 25 g/L methionine stock solution was prepared by dissolving methionine in water, and filter sterilizing the solution.)

Samples were taken at various time points and diluted at a ratio of 1:20 into methanol. Each diluted sample was vortexed for 30 minutes, and culture debris was spun down. Amorpha-4,11-diene titers were determined by transferring 5 to 10 uL of the supernatant to a clean glass vial containing 990 to 995 uL ethyl acetate spiked with trans-caryophyllene as an internal standard. The ethyl acetate samples were analyzed on an Agilent 7890N gas chromatograph equipped with a flame ionization detector (Agilent Technologies Inc., Palo Alto, CA). Compounds in a 1 uL aliquot of each sample were separated using a DB Wax column (Agilent Technologies, Inc., Palo Alto, CA), helium carrier gas, and the following temperature program: 220° C. hold for 3 minutes, increasing temperature at 100° C./minute to a temperature of 260° C. Using this protocol, amorpha-4,11-diene has a retention time of approximately 3.4 minutes. Amorpha-4,11-diene titers were calculated by comparing generated peak areas against a quantitative calibration curve of purified amorpha-4,11-diene in trans-caryophyllene-spiked ethyl acetate.

Figure 6:
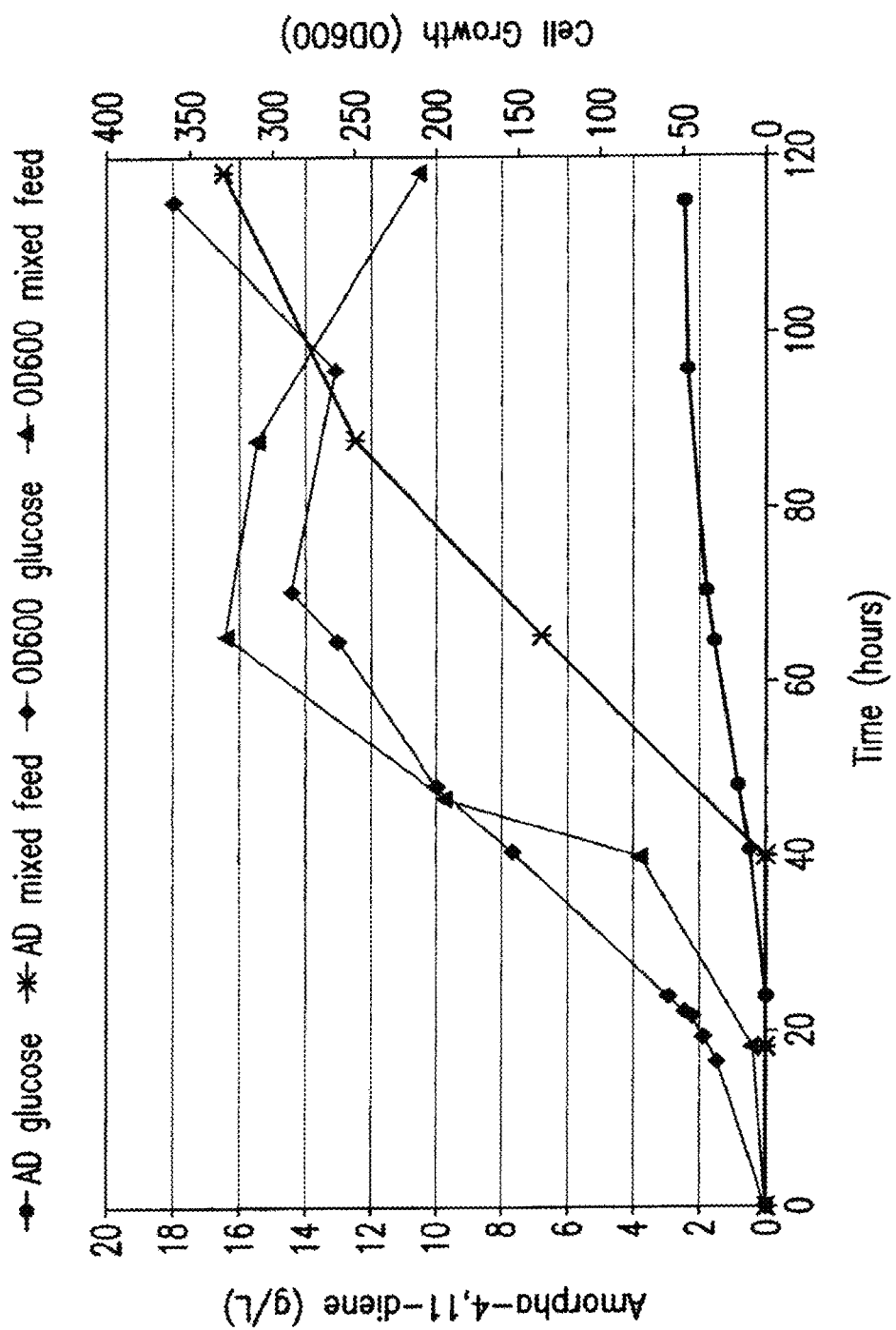
FIG. 6 shows cell growth and amorpha-4,11-diene (AD) production by strain Y337 under carbon restriction using either a glucose feed or a glucose/ethanol mixed feed.

As shown in Table 11 and FIG. 6, strain Y337 produced 2.4 g/L amorpha-4,11-diene (AD) at 114 hours after the start of the fermentation in the glucose only feed process.

TABLE 11

Amorpha-4,11-diene production by strain Y337 using either a glucose feed or a glucose/ethanol mixed feed

| Glucose in Feed Medium (g/L) | Ethanol in Feed Medium (g/L) | Maximum Feed Rate (g/hr/L) [a] | Stationary Feed Rate (g/hr/L) [a] | Maximum AD Titer (g/L) | Yield at Maximum Titer (mg product/g substrate) |
|---|---|---|---|---|---|
| 545 | 0 | 10 | 10 | 2.4 | 5.4 |
| 340 | 180 | 8.6 | 8.6 | 16.5 | 38.7 |
| 340 | 180 | 8.6 | 4.3 | 12.6 | 50.3 |

[a] g/hr/L is g substrate/hr/L bioreactor volume.

Example 5

This example describes the production of amorpha-4,11-diene by host cells in fed batch, carbon-restricted fermentation with a glucose-ethanol mixed feed.

Y337 seed cultures were prepared and used to inoculate bioreactors as described in Example 4. Fermentations were carried out, and samples were analyzed, essentially as described in Example 4 with the following modifications.

During the early phase of the fermentation, some of the glucose in the batch medium was converted to ethanol. The bioreactor culture was allowed to grow until the glucose and the ethanol in the batch medium was depleted, at which point an exponential feed was initiated for which mixed feed medium (Table 10) was pumped into the bioreactor at the rate defined by the following equations:

$$F = V \mu_{set} S_B e^{\mu_{set}(t-t_0)}$$

$$V = V_0 + V_{feed}$$

F is the substrate mass flow rate (g/hr), V is the liquid volume in the bioreactor at a given time (L), $S_B$ is the concentration of substrate in the batch media (20 g/L), $\mu_{set}$ is the specific feed rate (0.087 hr$^{-1}$), t is the batch age (hr), $t_0$ is the batch age when the feed was initiated (hr), $V_0$ is the initial volume in the bioreactor, and $V_{feed}$ is the total volume of feed added to the bioreactor at a given time (L). The exponential feed phase continued until the ratio of F/V reached a preset maximum feed rate in units of g substrate/hr/L bioreactor volume (Table 11). After reaching this maximum, the ratio of F/V was maintained constant for the remainder of the process at a preset stationary feed rate (Table 11).

Production of amorpha-4,11-diene was induced at an $OD_{600}$ of 77 about 40 hours after inoculation.

As shown in Table 11 and FIG. 6, strain Y337 produced up to 16.5 g/L amorpha-4,11-diene at 118 hours after the start of the fermentation in the mixed glucose and ethanol feed fermentation.

Example 6

This example describes the production of amorpha-4,11-diene by host cells in fed-batch, pulse feed fermentation with an ethanol only feed.

Figure 7A:
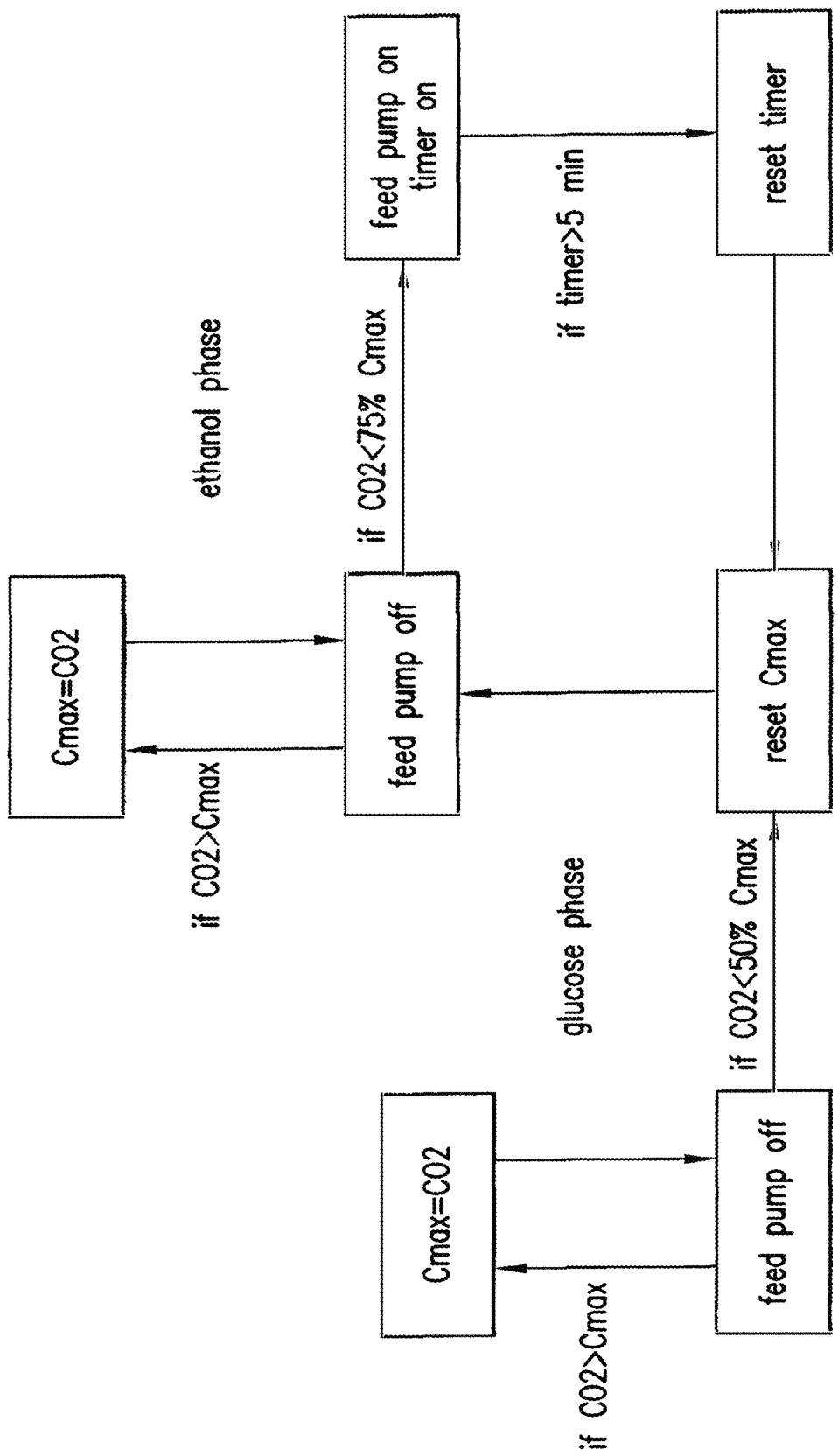
FIG. 7A shows a diagram of a CO2 control feed algorithm.
Figure 7B:
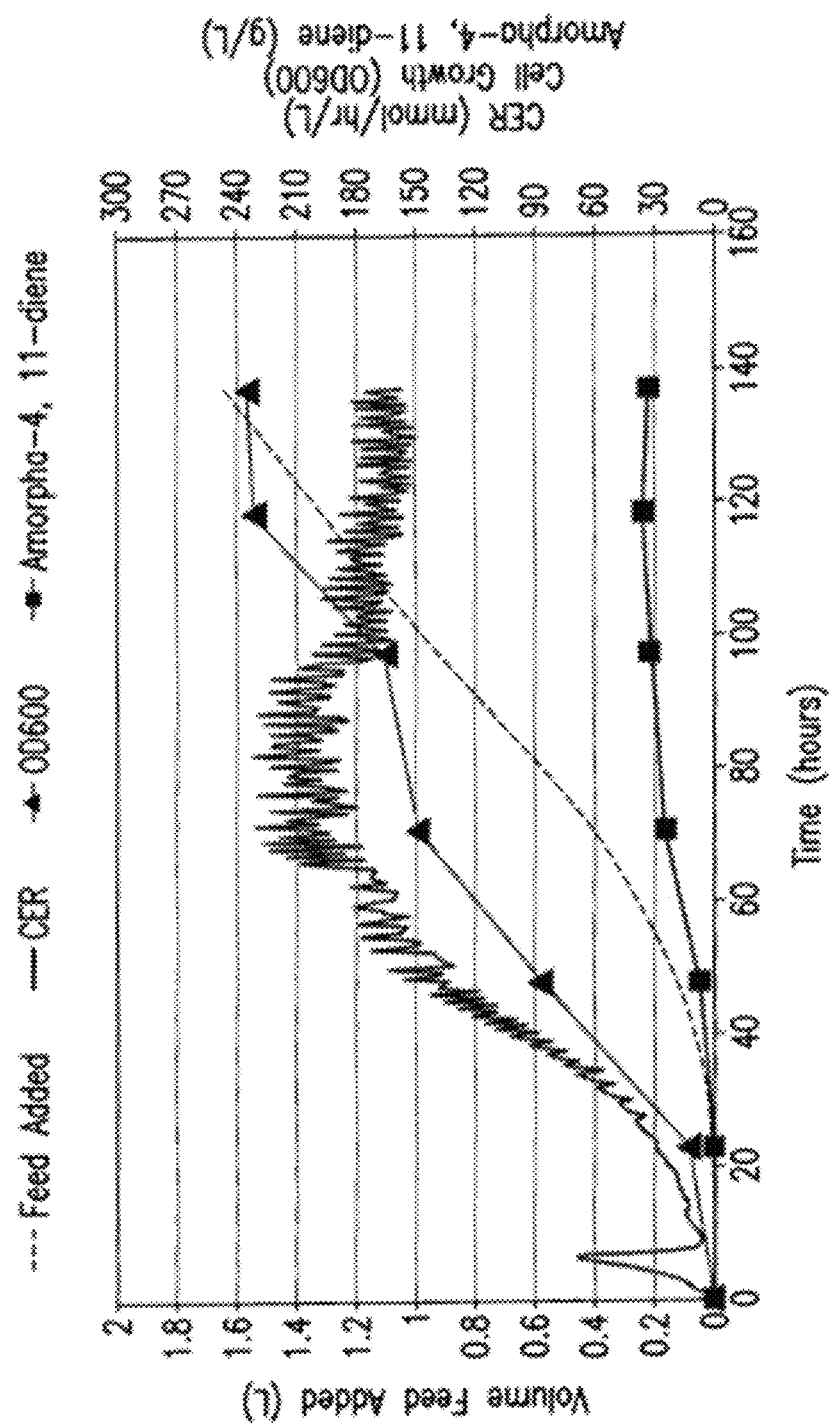
FIG. 7B shows carbon dioxide evolution rate, substrate delivery, growth, and production of amorpha-4,11-diene by strain Y293 using an ethanol pulse feed.

Y293 seed cultures were prepared and used to inoculate bioreactors as described in Example 3. Fermentations were carried out, and samples were analyzed, essentially as described in Example 4 with the following modifications:

During the early phase of the fermentation, some of the glucose in the batch medium was converted to ethanol. The bioreactor culture was allowed to grow until the glucose and the ethanol in the batch medium was depleted, at which point an ethanol pulse feed was initiated. The rate of the feed was controlled by the percent of $CO_2$ in the off-gas (the $CO_2$ evolution rate; CER), which was monitored with an off-gas analyzer and a computer algorithm that assigned a variable ($C_{max}$) to the maximum CER which tracked the maximum value of $CO_2$ percent in off gas. While growing on glucose, the CER evolved rapidly (FIG. 7B). When glucose was depleted from the batch medium, the CER dropped to below 50% of $C_{max}$, and the computer algorithm reset $C_{max}$ to the $CO_2$ value after the drop. When the ethanol produced from the excess glucose in the batch medium was depleted, the CER dropped a second time. The pulse feed was triggered automatically when the CER fell below 75% of the current $C_{max}$. The pump injected 75% (v/v) ethanol into the bioreactor for 5 minutes, delivering approximately 10 g ethanol to the culture. $C_{max}$ was reset to the value of the percent $CO_2$ in the off-gas at the time the pump was turned off and then reassign to track the increases in $CO_2$ evolution, and the pump was reactivated when the CER again fell below 75% of the newly set $C_{max}$. The feed algorithm was iterated throughout the fermentation (FIG. 7A), and ensured that the culture was not overfed with ethanol. Because none of the salts, trace metals, vitamins, sugars, or amino acid solutions were soluble in the ethanol feed, concentrated feed components (Table 12) were combined and injected through a septum in the bioreactor head plate once per day according to how much ethanol volume had been delivered since the previous addition of feed components.

TABLE 12

Concentrated feed components

| Component | Amount (mL/L ethanol) |
|---|---|
| glucose (450 g/L) | 24 |
| methionine (25 g/L) | 40 |
| 10x feed base [a] | 100 |
| Yeast vitamin solution (mL/L) (Table 9) | 12 |
| Yeast trace metals solution (Table 9) | 10 |

[a] 90 g/L $KH_2PO_4$, 51.2 g/L $MgSO_4 \cdot 7H_2O$, 35 g/L $K_2SO_4$, and 2.8 g/L $Na_2SO_4$ Ten hours after the glucose was depleted from the batch medium, 0.25 g/L methionine was added to the bioreactor through the head plate, and 10% v/v of autoclaved methyl oleate was pumped into the vessel. (Since strain Y293 comprises a disrupted GAL80 gene, galactose was not necessary to induce production of amorpha-4,11-diene.)

As shown in FIG. 7B, strain Y293 produced 36 g/L amorpha-4,11-diene.

Example 7

This example describes the production of amorpha-4,11-diene by host cells in fed batch, carbon-restricted fermentation with an ethanol only feed.

Y293 seed cultures were prepared and used to inoculate bioreactors containing batch medium (Table 13) as described in Example 3.

TABLE 13

Bioreactor media

| Component | Batch Medium |
| --- | --- |
| glucose-H2O (715 g/L) (mL/L) | 19.5 |
| (NH4)2SO4 (g/L) | 15 |
| KH2PO4 (g/L) | 26 |
| MgSO4*7H2O (g/L) | 16.4 |
| K2SO4 (g/L) | 7 |
| Na2SO4 (g/L) | 0.56 |
| Yeast vitamin solution (mL/L) (Table 9) | 46.3 |
| Yeast trace metals solution (mL/L) (Table 9) | 38.5 |

Fermentations were carried out, and samples were analyzed, essentially as described in Example 4 with the following modifications:

The bioreactor culture was allowed to grow until glucose in the batch medium was depleted, at which point an exponential feed was initiated for which glucose feed medium (Table 10) was pumped into the bioreactor at the rate defined by the following equations:

$$F = V\mu_{set}S_B e^{\mu_{set}(t-t_0)}$$

$$V = V_0 + V_{feed}$$

F is the substrate mass flow rate (g/hr), V is the liquid volume in the fermentor at a given time (L), $S_B$ is the concentration of substrate in the batch media (20 g/L), $\mu_{set}$ is the specific feed rate (0.087 hr$^{-1}$), t is the batch age (hr), $t_0$ is the batch age when the feed was initiated (hr), $V_0$ is the initial volume in the fermentor, and $V_{feed}$ is the total volume of feed added to the fermentor at a given time (L). The exponential feed continued until the maximum feed rate of 7.1 g/hr/L was reached (OD$_{600}$ of approximately 50). At that point, the feed was switched to an ethanol feed (190 proof), and the feed rate was set to a constant volumetric value of 2.5 g/hr/L for the remainder of the fermentation. With this programmed feed rate, ethanol consumption rates were controlled, and ranged from 0.4 to 1.75 g ethanol/g DCW/day.

Figure 8:
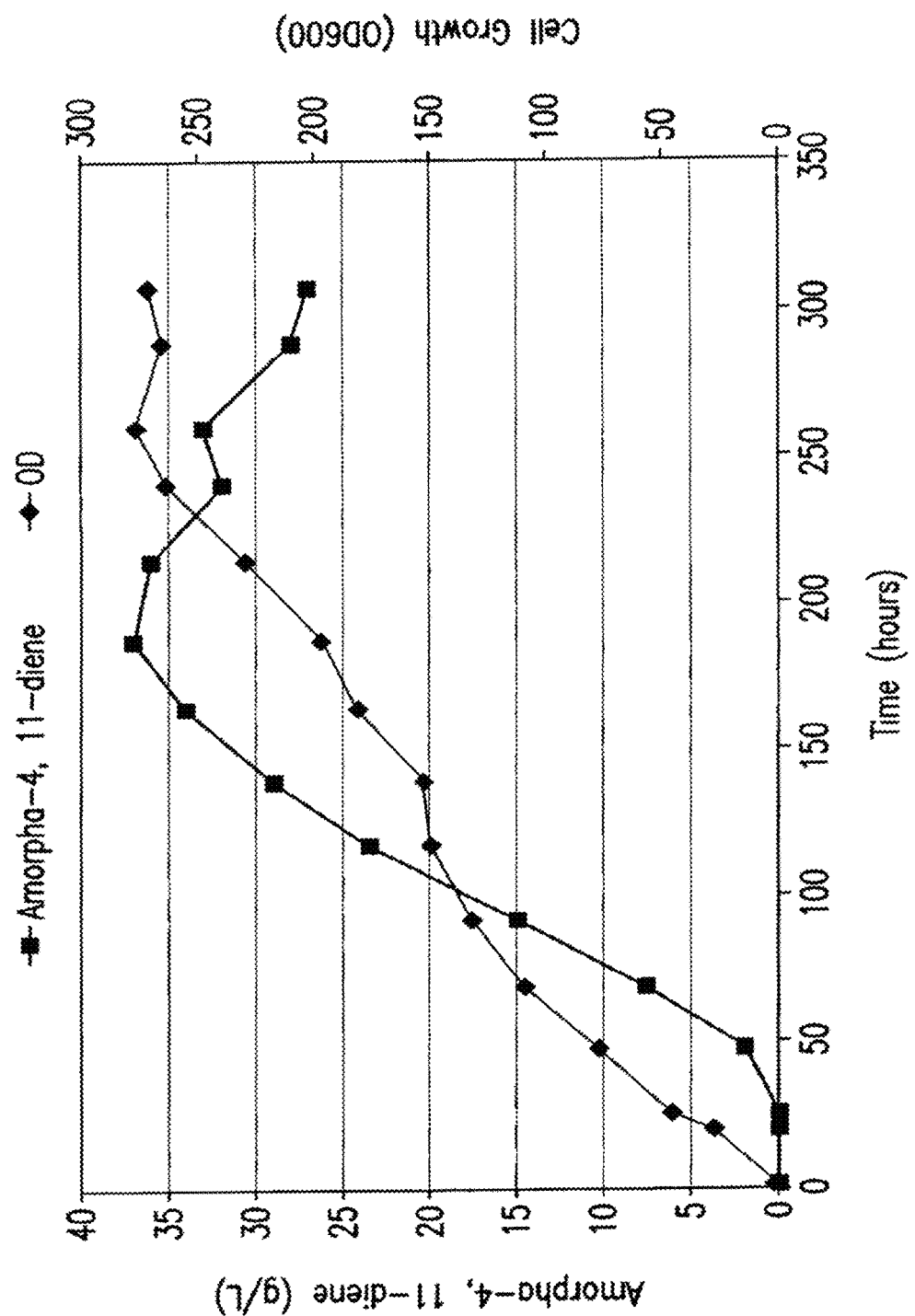
FIG. 8 shows cell growth and amorpha-4,11-diene production by strain Y293 under carbon restriction using a concentrated glucose feed for initial growth followed by an ethanol feed for production.

As shown in FIG. 8, strain Y293 produced 37 g/L amorpha-4,11-diene at 187 hours after the start of fermentation.

Example 8

This example describes the production of farnesene by host cells in fed batch, carbon-restricted fermentation with an ethanol only feed.

Y677 seed cultures were prepared and used to inoculate two bioreactors each containing 630 mL batch medium (Table 14) as described in Example 3. To one of the two bioreactors, 200 mL methyl oleate was added for product capture. Fermentations were carried out, and samples were analyzed, essentially as described in Example 4 with the following modifications:

TABLE 14

Bioreactor media

| Component | Batch Medium |
| --- | --- |
| Glucose (g/L) | 39.03 |
| (NH4)2SO4 (g/L) | 15 |
| KH2PO4 (g/L) | 33.7 |
| MgSO4*7H2O (g/L) | 20.77 |
| K2SO4 (g/L) | 10 |
| Na2SO4 (g/L) | 0.8 |
| Yeast vitamin solution (mL/L) (Table 9) | 32.4 |
| Yeast trace metals solution (mL/L) (Table 9) | 27 |

During the early phase of the fermentations, some of the glucose in the batch medium was converted to ethanol. The bioreactor cultures were allowed to grow until the glucose and the ethanol in the batch media were depleted, at which point, an exponential feed was initiated for which pure ethanol (190 proof) was pumped into the bioreactor at the rate defined by the following equations:

$$F = V\mu_{set}S_B e^{\mu_{set}(t-t_0)}$$

$$V = V_0 + V_{feed}$$

Figure 9A:
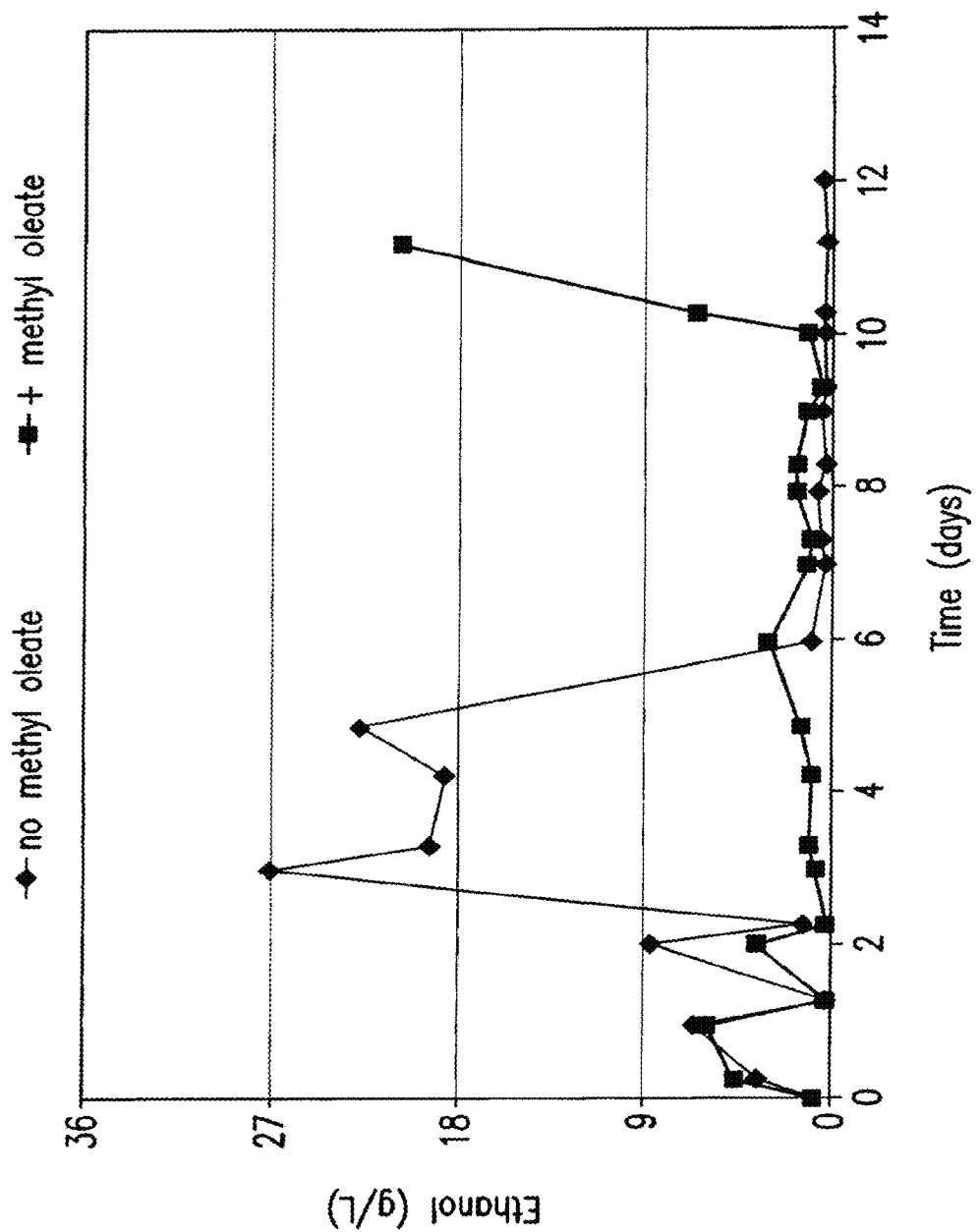
FIGS. 9A through 9E show ethanol production/consumption, feed rate, growth, carbon evolution and oxygen utilization rates, and farnesene production by strain Y677 in fed batch, carbon-restricted fermentation with an ethanol only feed. in the presence or absence of methyl oleate.
Figure 9B:
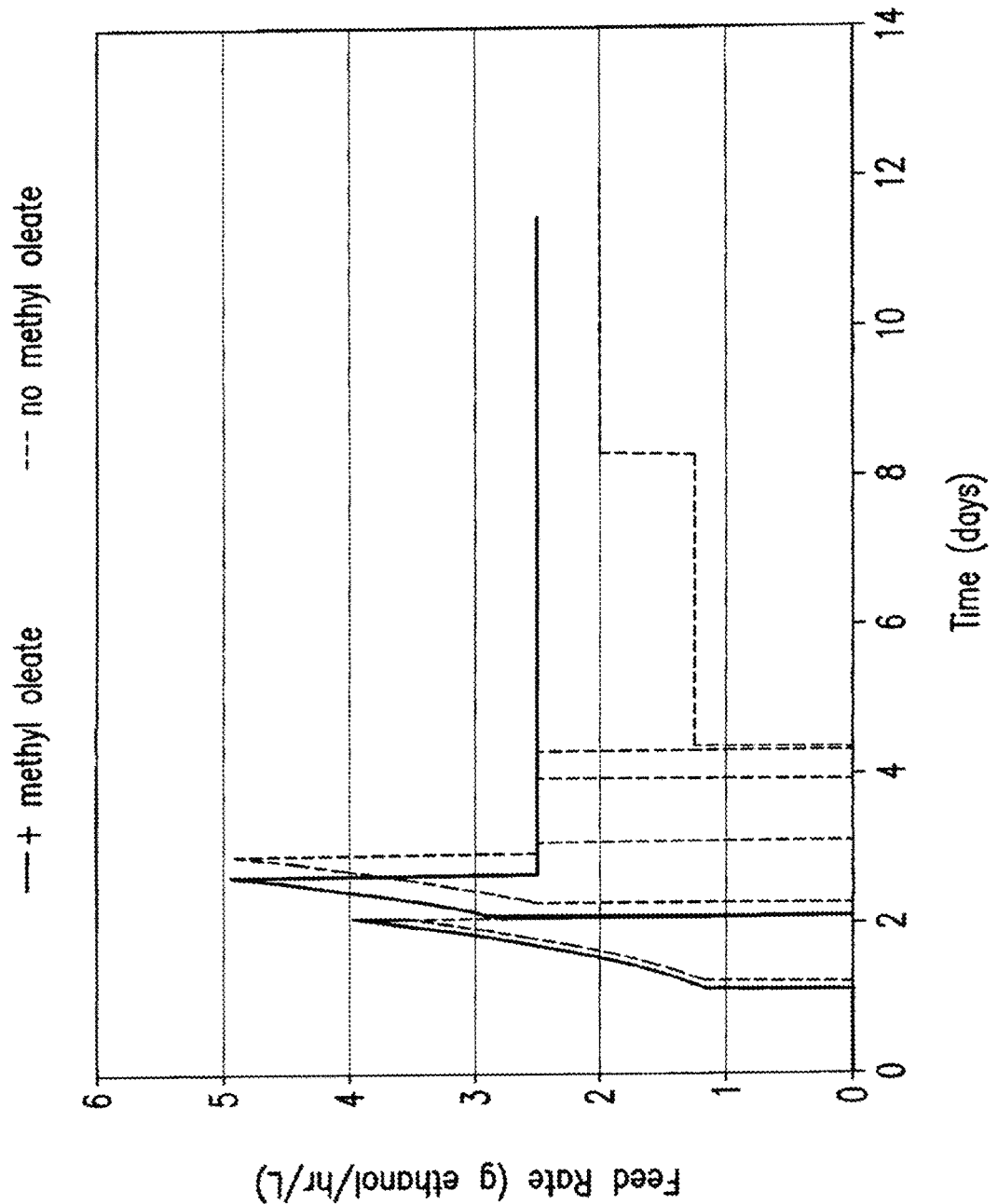
Figure 9C:
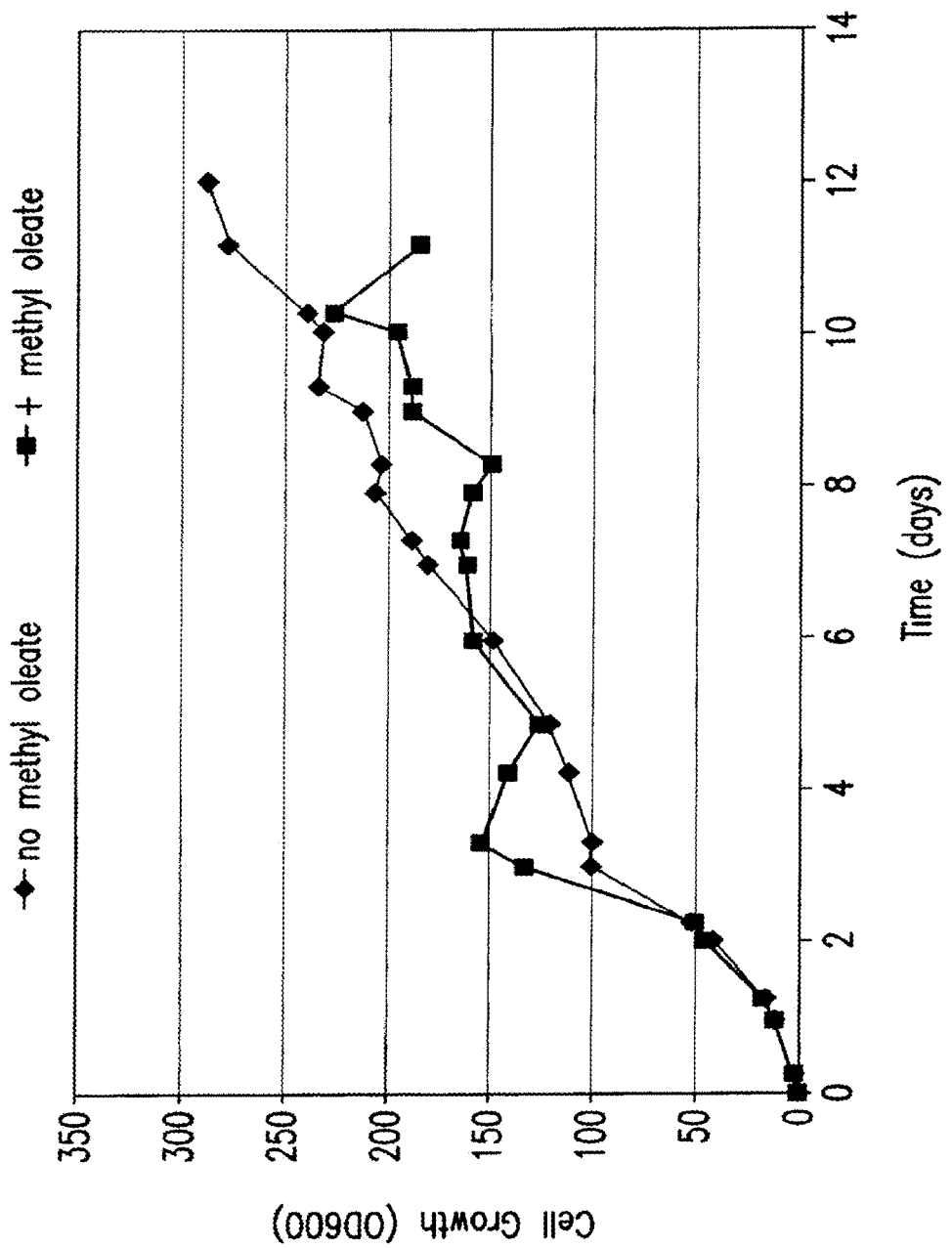

F is the substrate mass flow rate (g/hr), V is the liquid volume in the fermentor at a given time (L), $S_B$ is the concentration of substrate in the batch media (39.03 g/L), $\mu_{set}$ is the specific feed rate (0.058 hr$^{-1}$), t is the batch age (hr), $t_0$ is the batch age when the feed was initiated (hr), $V_0$ is the initial volume in the fermentor (0.7 L), and $V_{feed}$ is the total volume of feed added to the fermentor at a given time (L). The exponential feed phase continued until the ratio of F/V reached a maximum feed rate of 5 g substrate/hr/L bioreactor volume. After reaching this maximum, the ratio of F/V was maintained constant for the remainder of the process at a stationary feed rate of 2.5 g/hr/L. However, as shown in FIG. 9A, the relatively slow rate of ethanol utilization at the beginning of the exponential feed phase resulted in the accumulation of ethanol. This accumulation necessitated manual adjustment of the preset feed rates (FIG. 9B) and an increase in the feed rate doubling time from 12 to 14 hours to maintain a carbon-limited process. Cells grown in the presence of methyl oleate quickly recovered and resumed growth to the preset maximum and stationary feed rates (FIG. 9C). In contrast, the culture that contained no methyl oleate was slower to consume the accumulated ethanol, and thus required a second suspension of the stationary feed followed by a reduction of the stationary feed rate from 2.5 g/hr/L to 1.25 g/hr/L. Overall, strain Y677 had an ethanol consumption rate of 0 to 2.1 g ethanol/g DCW/day in the absence of methyl oleate, and of 0.27-2.9 g ethanol/g DCW/day in the presence of methyl oleate.

Figure 9D:
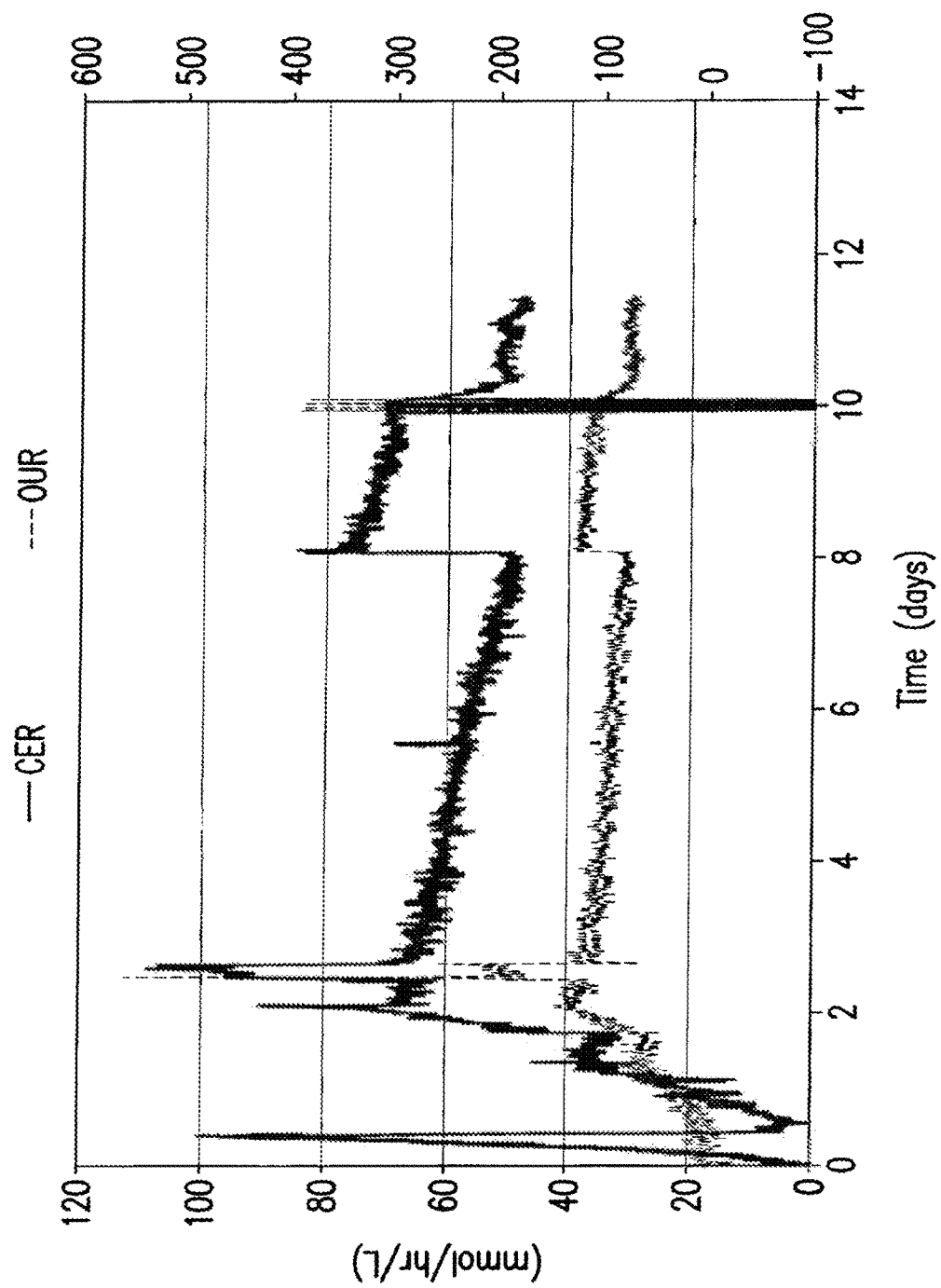

The off gas of the bioreactor was led through a condenser to measure oxygen uptake rate (OUR) and CO$_2$ generation (CER) using an off-gas mass spectrometer. FIG. 9D shows the CER and OUR of strain Y677 in the presence of methyl oleate.

Cell densities and ethanol consumption were monitored by sampling twice a day. At each time point, 1 mL broth samples were taken and diluted 1:1000 in water, and cell density was measured using a spectrophotometer set at 600 nm wavelength.

Levels of ethanol were quantified by HPLC. At each time point, a 1 mL broth sample was taken and diluted 2× in 30 mM sulfuric acid solution (400 uL 30 mM sulfuric acid to 400 uL supernatant for a final concentration of 15 mM sulfuric acid, which matched the concentration of the mobile phase solution). Cells were removed by centrifugation and filtration prior to loading.

Levels of farnesene produced were quantified by GC-FID. At each time point, 100 uL of methyl oleate overlay was taken and diluted 1:40 in ethyl acetate containing 0.001% trans-beta caryophyllene. The mixture was once again diluted 1:100 in ethyl acetate for a final 1:4000 dilution, which fit within the calibration curve for the method. When no methyl oleate was used for product capture, 25 uL culture broth was combined with 975 uL methanol, the mixture was vortexed for five minutes and centrifuged, and finally diluted 1:100 in ethyl acetate containing 0.001% trans-beta caryophyllene before analysis.

Figure 9E:
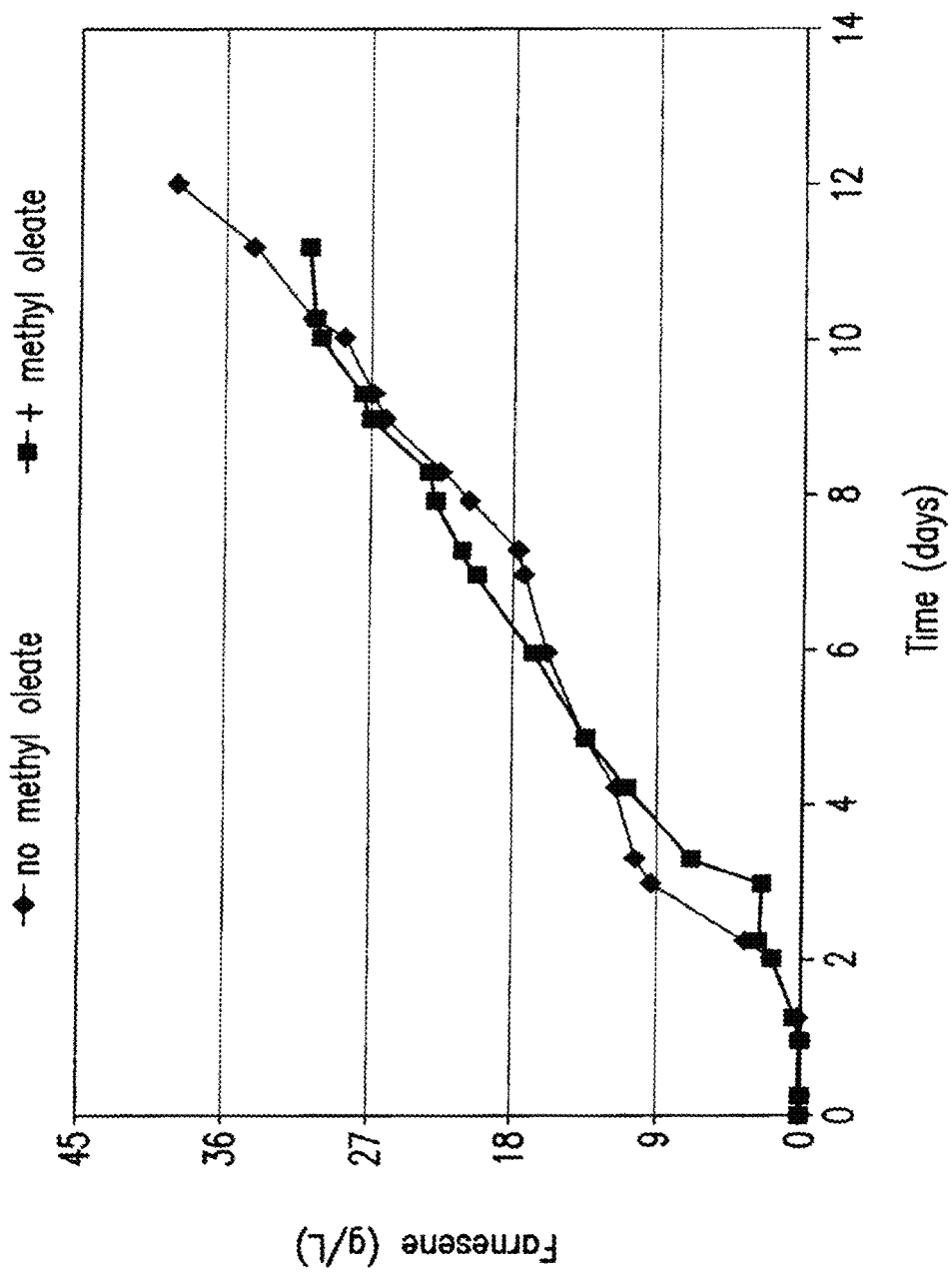

As shown in FIG. 9E, in the presence of methyl oleate strain Y677 reached a peak farnesene titer of 30 g/L, and in the absence of methyl oleate it reached a peak farnesene titer of 40 g/L.

Example 9

This example describes the production of amorpha-4,11-diene and farnesene by host cells in oxygen-restricted fermentation.

Y283 and Y352 seed cultures were prepared and used to inoculate bioreactors containing 800 mL batch medium (Table 15) and 100 mL methyl oleate as described in Example 3.

TABLE 15

Bioreactor media

| Component | Seed Medium | Batch Medium |
|---|---|---|
| glucose (g/L) | 20 | 30 |
| galactose (g/L) | 0 | 5 |
| methionine (g/L) | 0 | 0.25 |
| $(NH_4)_2SO_4$ (g/L) | 15 | 15 |
| $KH_2PO_4$ (g/L) | 8 | 8 |
| $MgSO_4*7H2O$ (g/L) | 6.15 | 6.15 |
| Yeast vitamin solution (mL/L) (Table 9) | 12 | 12 |
| Yeast trace metals solution (mL/L) (Table 9) | 10 | 10 |
| succinate (0.5M, pH 5.0) (mL/L) (Table 7) | 100 | 0 |

Fermentations were carried out in 2L Sartorius Biostat B plus twins with gas-flow ration controllers. The pH was controlled automatically at pH 5.0 with the addition of 15N $NH_4OH$ and 5N $H_2SO_4$. Temperature was maintained at 30° C. and Biospumex 200 K brand antifoam was used to control foam. Bioreactors were inoculated between OD500 of 0.6-1 and allowed to grow on 30 g/L glucose.

The off gas of the bioreactor was led through a condenser to measure oxygen uptake rate (OUR) and $CO_2$ generation (CER) using an off-gas mass spectrometer. The dissolved oxygen (DO) concentration was measured using an $O_2$ sensor probe (Hamilton, OXYFERM FDA 225, Hamilton Company, Reno, NV) with sensitivity between 10 ppb to saturation.

During the initial phase of the fermentation, the bioreactor culture converted the glucose in the batch medium to biomass and ethanol. When the glucose was consumed (8-14 hours after the start of fermentation depending on the availability of oxygen in the culture) glucose repression of the galactose transport and transcription machinery was alleviated, and gene expression off GAL promoters was induced by the galactose in the batch medium. The batch culture continued growth until ethanol produced in the fermentative stage was depleted, at which point a DO spike marked the end of the cultivation period.

For the aerobic process, clean dry air was sparged into the medium at a rate of 1 LPM. The stir rate was initially set to 400 rpm, and a DO feedback control loop and stir cascade program were used to maintain the DO concentration at 40% (Table 16).

For the micro-aerobic processes, gas flow was reduced to 0.25 LPM to minimize the dilution of gases that reach the off gas analyzer and to increase the sensitivity of the mass spectrometer. The rate of oxygen delivery was varied by using different gas-flow ratios of air to nitrogen (Table 16).

For the strict anaerobic process, 100% nitrogen gas was sparged into the aqueous medium at 0.25 LPM prior to inoculation, and a constant stir rate of 400 rpm was maintained throughout the cultivation (Table 16).

TABLE 16 parameters for fermentations of strain Y283

| Process | Conditions | Controlled Parameters | Gas Flow Composition |
|---|---|---|---|
| Aerobic | 40% DO | starting 400 rpm DO feedback control with cascading stir rate | 100% air (21% $O_2$) |
| Microaerobic | 0% DO | no DO feedback control fixed stir rate at 400 rpm | 100% air, 0% N2 |
|  |  |  | 90% air, 10% N2 |
|  |  |  | 80% air, 20% N2 |
|  |  |  | 65% air, 35% N2 |
|  |  |  | 50% air, 50% N2 |
|  |  |  | 50% air, 50% N2 |
|  |  |  | 35% air, 65% N2 |
|  |  |  | 20% air, 80% N2 |
| Anaerobic | No air supplied | fixed stir rate at 400 rpm | 0% air, 100% N2 |

Cell densities and ethanol consumption were monitored by sampling twice a day. At each time point, 1 mL broth samples were taken and diluted 1:100 in water, and cell density was measured using a spectrophotometer set at 600 nm wavelength.

Levels of ethanol and farnesene produced were quantified as described in Example 8 except that the methyl oleaste sample was diluted in ethyl acetate to a final 1:400 dilution instead of 1:4000 dilution.

Figure 10A:
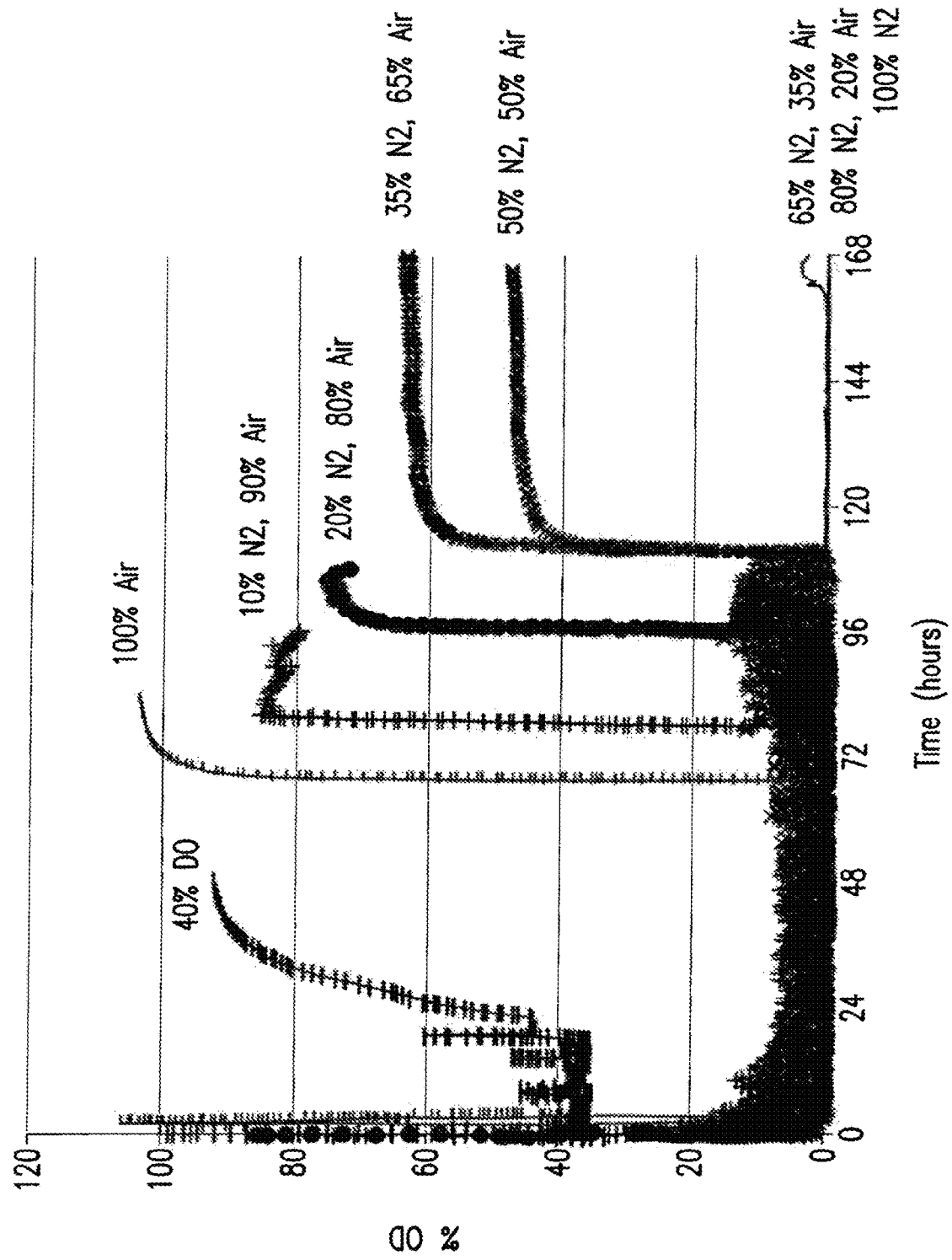
FIGS. 10A through 10D show dissolved oxygen concentration, growth, ethanol production/consumption, and amorpha-4,11-diene production by strain Y283 at different degrees of oxygen limitation.
Figure 10B:
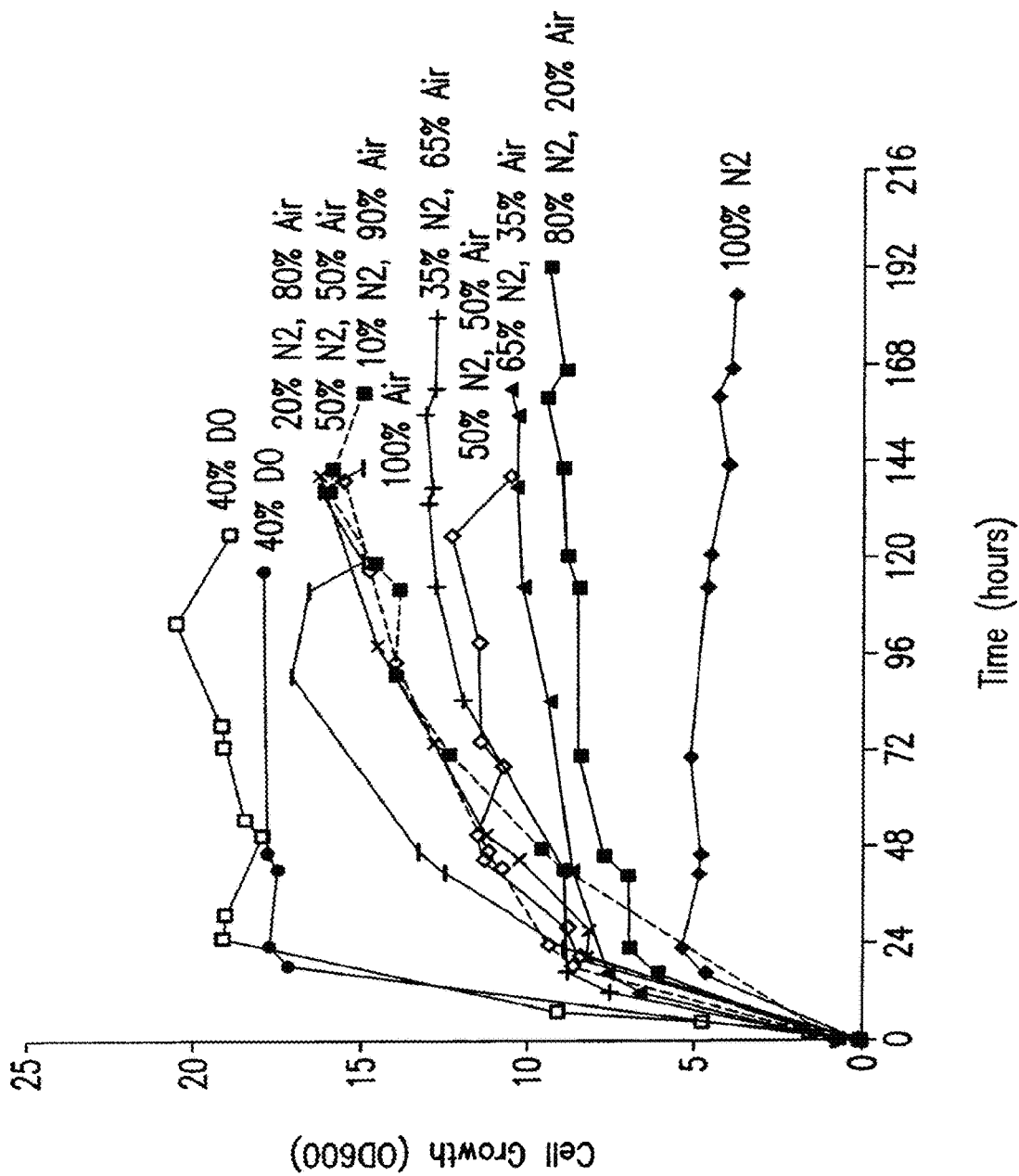
Figure 10C:
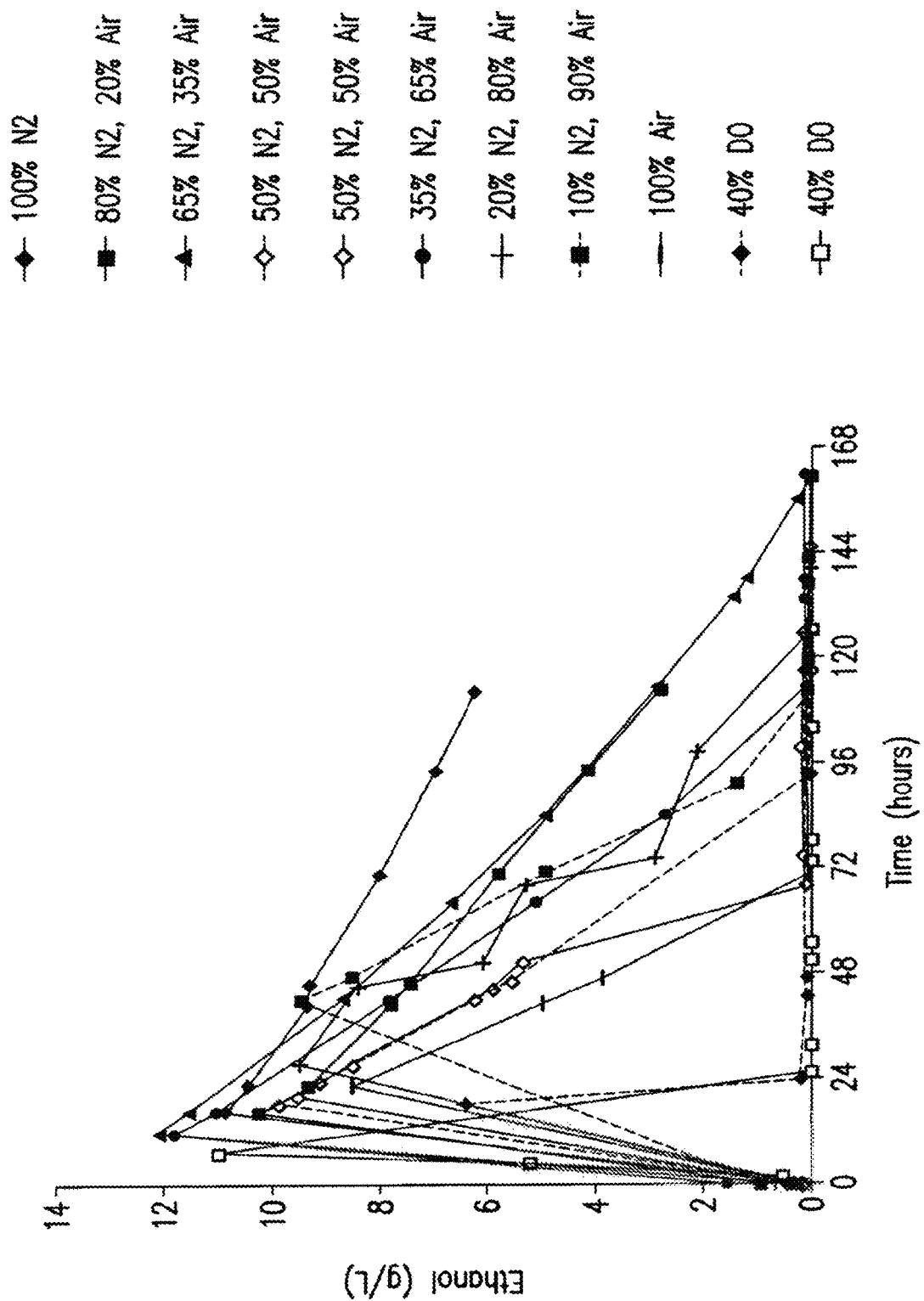
Figure 10D:
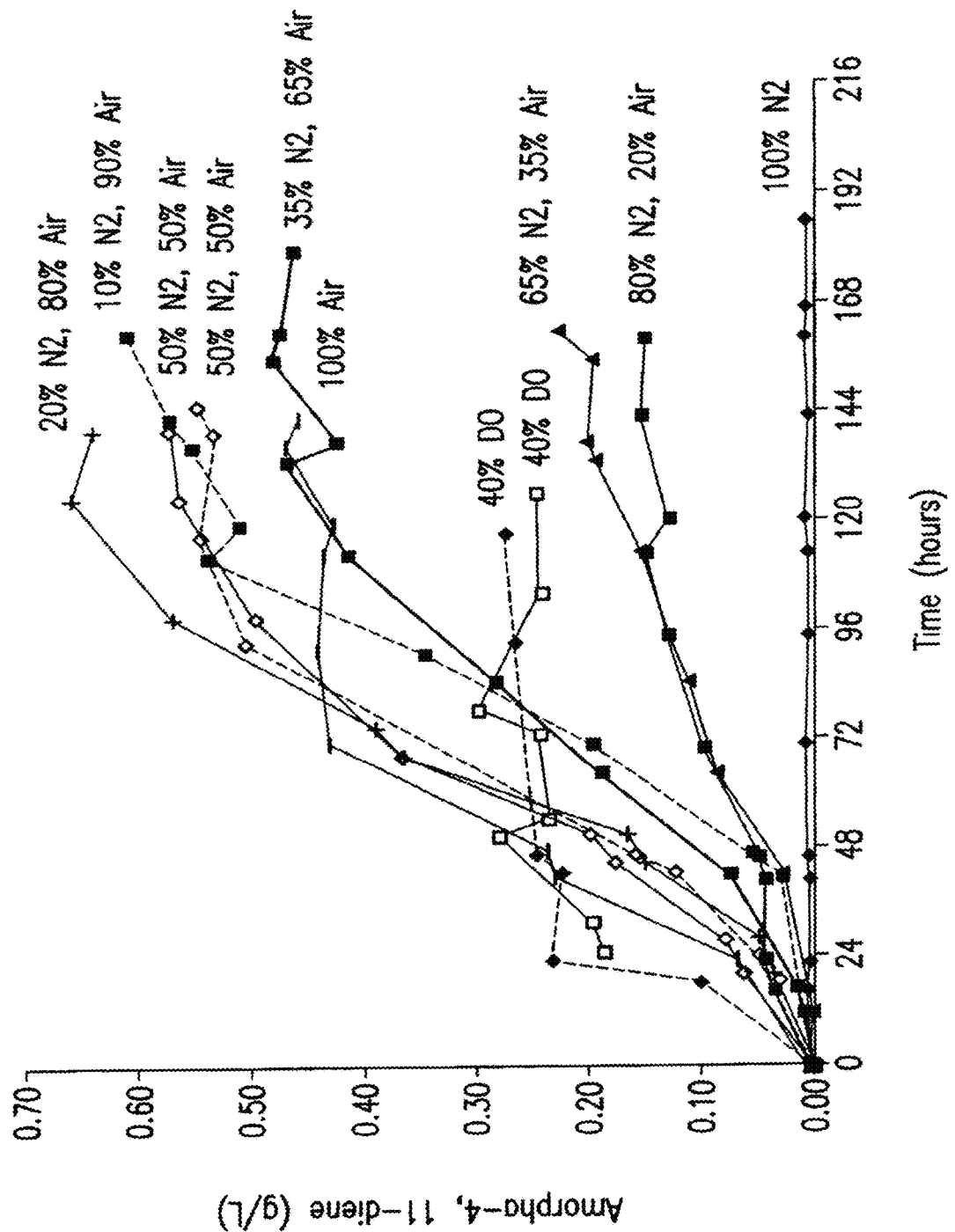

FIG. 10A shows the DO concentrations in the various fermentations of host strain Y283. As shown in FIGS. 10B and 10C, in strain Y283 increased oxygen availability in the culture lead to increased cell growth, increased rate of glucose conversion to ethanol, and increased rate of depletion of ethanol from the medium. Although growth, product formation, and ethanol consumption by strain Y283 were greatest in the fully aerated cultures (DO of 40%), they plateaued after 24 hours. As shown in Table 17, the per cell ethanol consumption rate for all microaerobic processes was between 0.40-0.72 g ethanol/g DCW/day. As shown in FIG. 10D, the best yield of amorpha-4,11-diene relative to carbon input was observed at 80% air and 20% nitrogen.

TABLE 17

Specific ethanol utilization rate (EUR) for microaerobic fermentations

| Gas Ratio | Y283 EUR (g ethanol/g DCW/day) | Y352 EUR (g ethanol/g DCW/day) |
|---|---|---|
| 100% N2 | 0.42 | |
| 80% N2 | 0.40 | |
| 65% N2 | 0.42 | 0.42 |
| 50% N2 | 0.65 | 0.69 |
| 50% N2 | 0.58 | |
| 35% N2 | 0.54 | |
| 20% N2 | 0.57 | |
| 10% N2 | 0.60 | |
| 0% N2 | 0.72 | 0.88 |

EUR was calculated from peak measured ethanol to lowest measured ethanol for the fermentation.

Figure 10E:
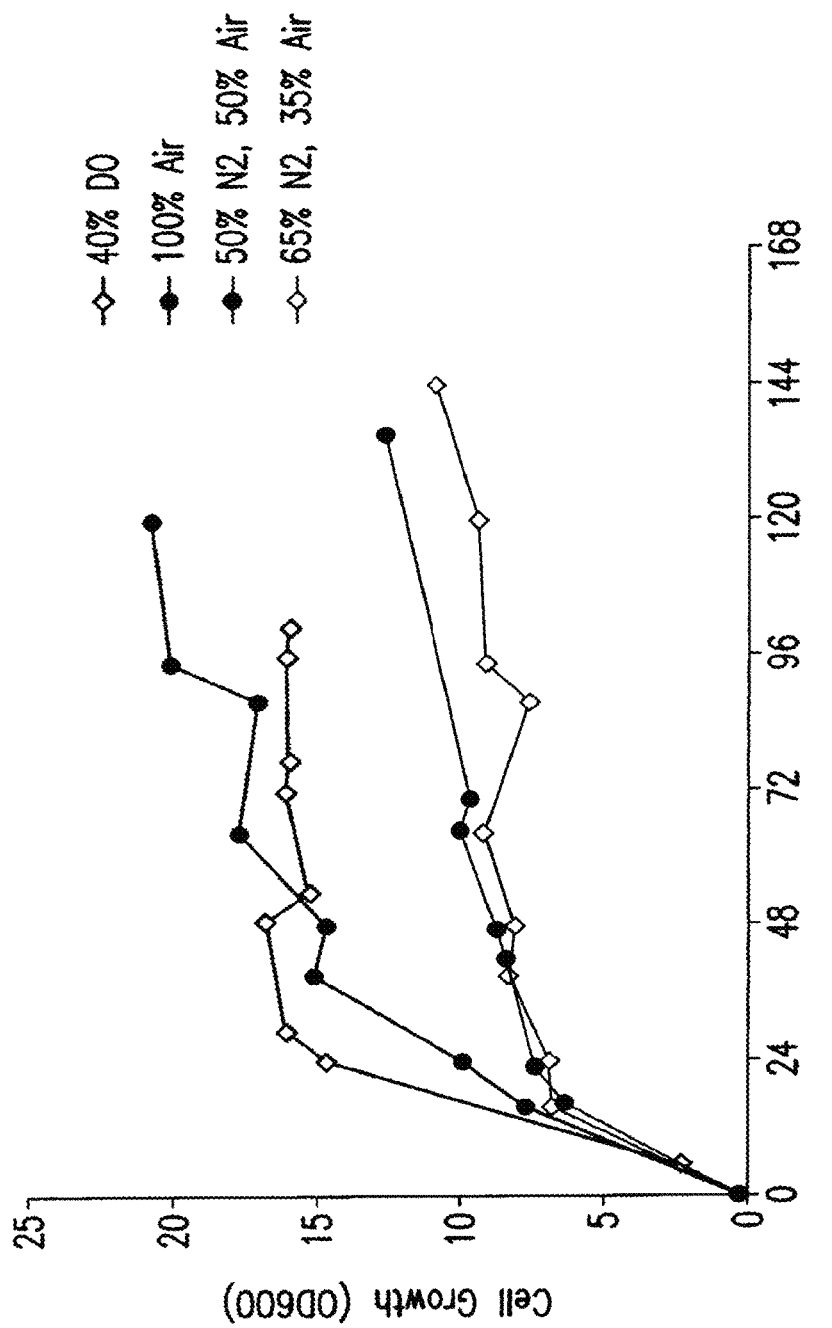
FIGS. 10E through 10G show growth, ethanol production/consumption, and farnesene production by strain Y352 at different degrees of oxygen limitation.
Figure 10F:
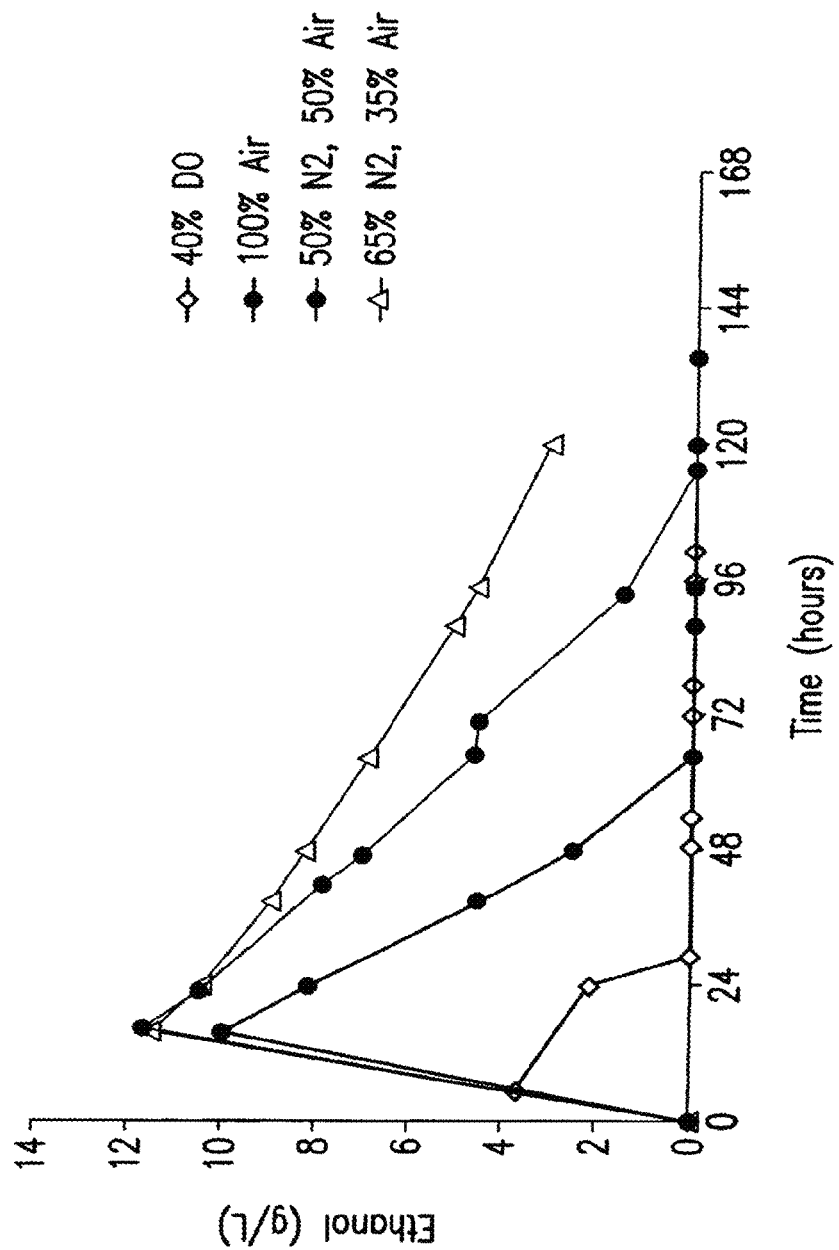
Figure 10G:
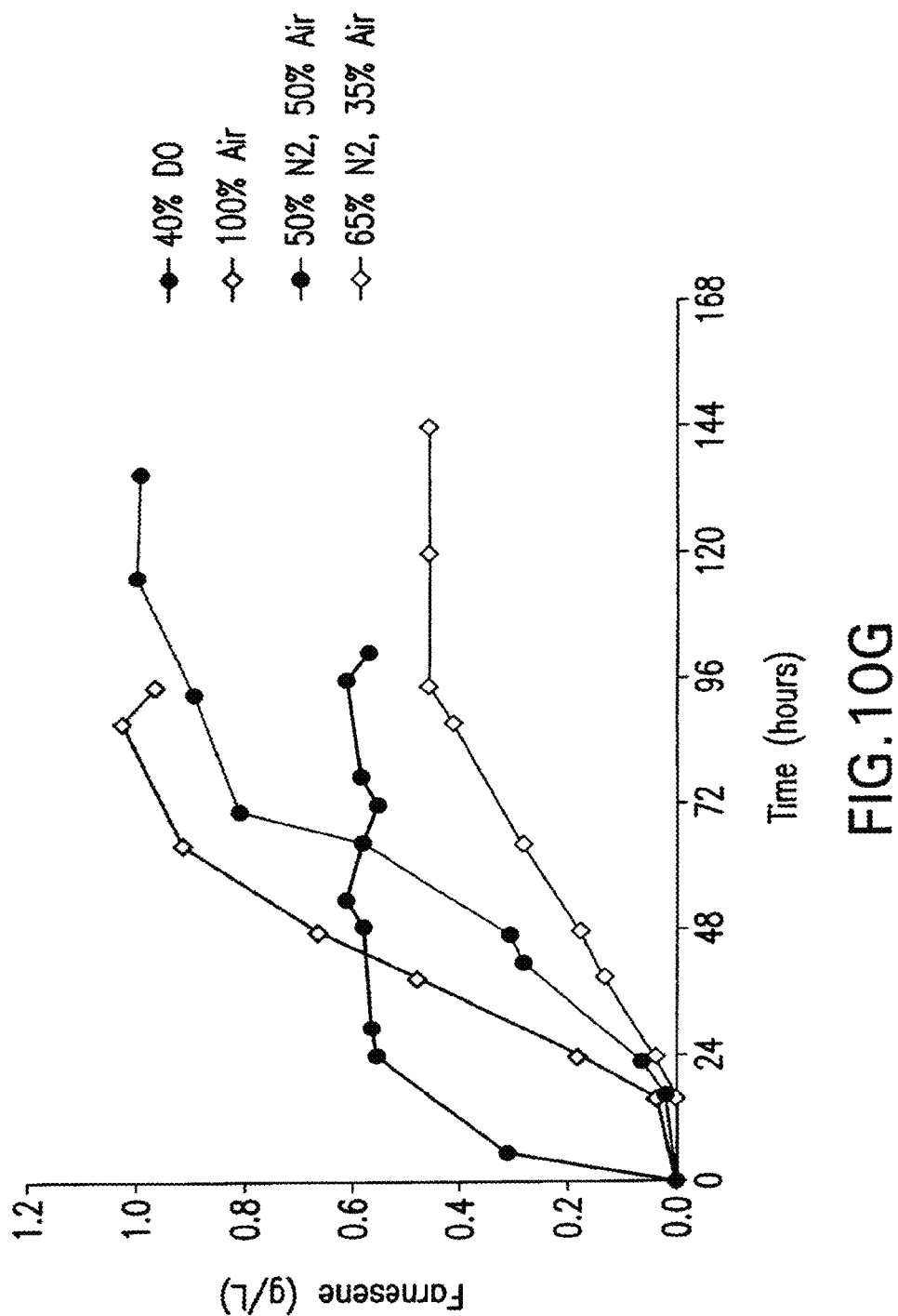

As shown in FIGS. 10E and 10F, in strain Y352 increased oxygen availability in the culture lead to increased cell growth, increased rate of glucose conversion to ethanol, and increased rate of depletion of ethanol from the medium. As shown in Table 17, the per cell ethanol consumption rate for the two microaerobic processes tested was between 0.42-0.88 g ethanol/g DCW/day. As shown in FIG. 10G, although slightly higher yield of farnesene on carbon input was observed at 100% air, production continued over a longer period of time in the microaerobic cultures.

Example 10

This example describes the production of amorpha-4,11-diene by host cells in shake flask cultures with carbon and phosphate restriction.

A stock amyloglucosidase (glucoamylase) enzyme solution was prepared by dissolving solid amyloglucosidase (Sigma A7420-100 MG) in 0.5 M succinate buffer (pH 5.0) to a final enzyme concentration of 100 U/mL, and filter sterilizing the solution.

A Y337 seed culture was prepared by inoculating 1 mL frozen Y337 cells into a 250 mL baffled flask containing 50 mL of phosphate-restricted seed medium (Table 18). The seed culture was grown overnight at 30° C. and 200 rpm.

TABLE 18

Phosphate-restricted shake flask culture media

| Component | Seed Medium (mL/L) | Production Medium (mL/L) |
|---|---|---|
| tap water | 350 | 250 |
| 2X batch base [a] | 500 | 500 (no $KH_2PO_4$) |
| Yeast vitamin solution (Table 9) | 12 | 12 |
| Yeast trace metals solution (Table 9) | 10 | 10 |
| succinate (0.5M, pH 5.0) (Table 7) | 100 | 100 |
| glucose-$H_2O$ (715 g/L) (Table 7) | 30 | 0 |
| Maltrin M-150 (500 g/L) | 0 | 100 |
| galactose (250 g/L) | 0 | 20 |
| methionine (25 g/L) | 0 | 10 |

[a] 1 g/L $KH_2PO_4$, 30 g/L $(NH_4)_2SO_4$, and 12.3 g/L $MgSO_4 \cdot 7H_2O$ (note: no heating while mixing)

The Y337 seed culture was used to inoculate several 250 mL baffled shake flasks to a starting $OD_{600}$ of 0.05. Production flasks contained 40 mL of phosphate-restricted production medium (Table 18). $KH_2PO_4$ was added to each flask from a 100 g/L filter-sterilized stock solution to final concentrations of 0.1, 0.25, 0.5, 0.8, 2, and 8 g/L. Prior to inoculation, 80 μL of freshly thawed 100 U/mL amyloglucosidase filter-sterilized stock solution was added to each flask (final concentration of 0.2 U/mL). Production flasks were incubated at 30° C. and 200 rpm for up to 3 days. Over the course of the culture period, glucose was released by glucoamylase at the constant rate of approximately 20 mg/hour.

Amorpha-4,11-diene titers were determined by transferring 2 to 10 μL of the methyl oleate overlay to a clean glass vial containing 500 μL ethyl acetate spiked with beta- or trans-caryophyllene as an internal standard, and analyzing the ethyl acetate samples as described in Example 4.

Figure 11:
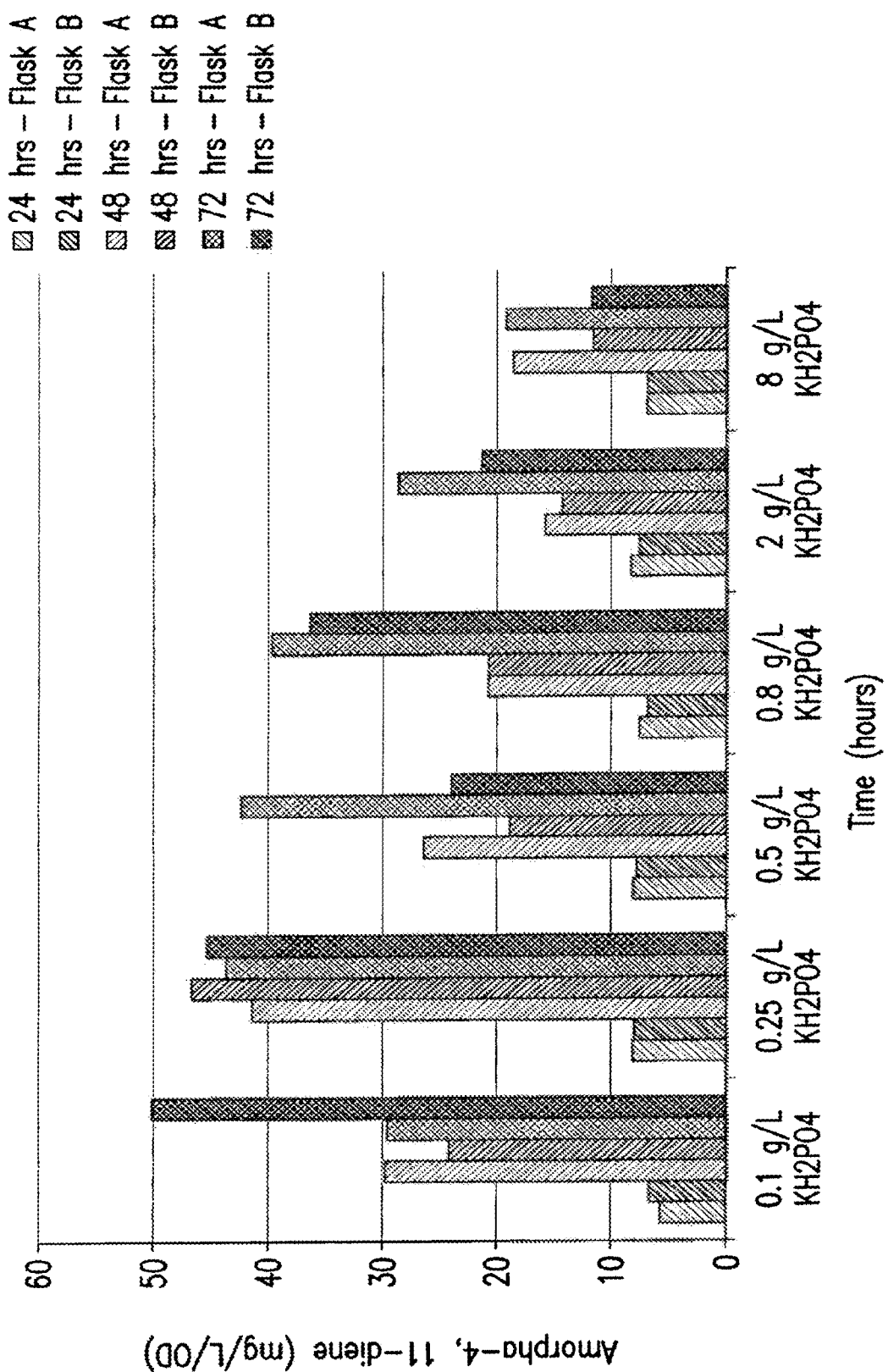
FIG. 11 shows per cell amorpha-4,11-diene productivity by strain Y337 in shake flasks under carbon restriction with varying concentrations of KH2PO4.

As shown in FIG. 11, overall amorpha-4,11-diene titers were comparable at all phosphate concentrations tested except the lowest (0.1 g/L), but cell growth was limited at lower phosphate concentrations, translating into increased per cell production of amorpha-4,11-diene at lower phosphate concentrations.

Example 11

This example describes the production of amorpha-4,11-diene by host cells in fed batch, carbon-restricted fermentation with phosphate restriction and a glucose feed.

Y337 seed cultures were prepared and used to inoculate bioreactors containing phosphate-restricted batch medium (Table 19) as described in Example 3. Fermentations were carried out, and samples were analyzed, essentially as described in Example 4 with the following modifications.

The bioreactor culture was allowed to grow until glucose in the batch medium was depleted, at which point, an exponential feed was initiated for which phosphate-restricted glucose feed medium (Table 19) was pumped into the bioreactors at the rate defined by the following equations:

$$F = V\mu_{set}S_B e^{\mu_{set}(t-t_0)}$$

$$V = V_0 + V_{feed}$$

F is the substrate mass flow rate (g/hr), V is the liquid volume in the bioreactor at a given time (L), $S_B$ is the concentration of substrate in the batch medium (19.5 g/L), $\mu_{set}$ is the specific feed rate (0.087 hr$^{-1}$), t is the batch age (hr), $t_0$ is the batch age when the feed was initiated (hr), $V_0$ is the initial volume in the bioreactor, and $V_{feed}$ is the total volume of feed added to the bioreactor at a given time (L).

Figure 12A:
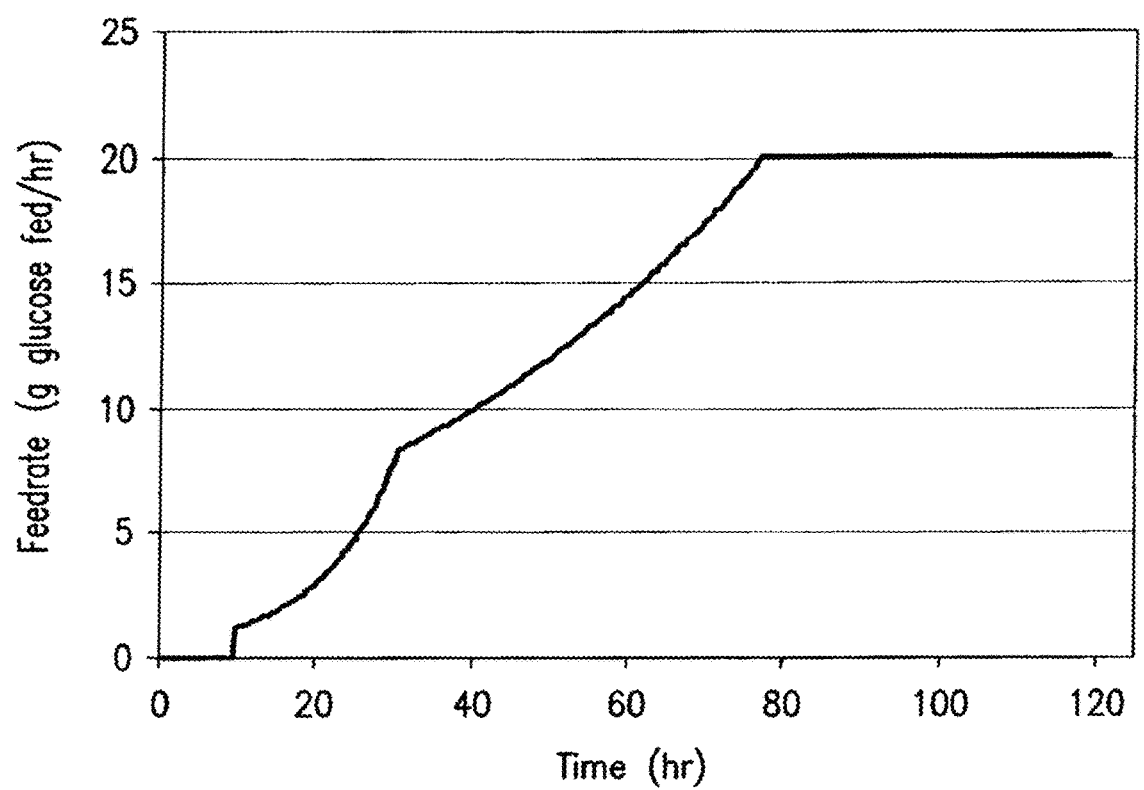
FIG. 12 shows a fed-batch fermentor feed (A), and cell growth (B) and amorpha-4,11-diene production (C) by strain Y337 under carbon- and phosphate-restriction using a glucose feed.

The exponential feed continued until the ratio of F/V reached a preset maximum feed rate (Table 20). After reaching this maximum feed rate, the ratio of F/V was maintained constant for the remainder of the process at a preset stationary feed rate. However, because the volume (V) continued to increase as more feed was added to the bioreactor, the substrate mass flow rate (F) continued to increase until the volume reached the maximum working volume of the bioreactor (approximately 3 times the starting volume). For the rest of the process, the bioreactor volume was held constant by removing cell broth continuously from the reactor, and the substrate mass flow rate (F) was held constant. FIG. 12A shows the glucose feed rate profile of the fermentation.

TABLE 19

Phosphate-restricted bioreactor media

| Component | Seed Medium [a] | Batch Medium [b] | Glucose Feed Medium [c] | Mixed Feed Medium [d] |
|---|---|---|---|---|
| glucose (g/L) | 20 | 19.5 | 578 | 425 |
| (NH$_4$)$_2$SO$_4$ (g/L) | 15 | 15 | 0 | 0 |
| KH$_2$PO$_4$ (g/L) | 1 | See Tables 20 and 21 | See Table 20 | See Table 21 |
| MgSO$_4$*7H2O (g/L) | 6.15 | 6.15 | 5.12 | 5.12 |
| K$_2$SO$_4$ (g/L) | 0 | 0 | 3.5 | 3.5 |
| Na$_2$SO$_4$ (g/L) | 0 | 0 | 0.28 | 0.28 |
| Yeast vitamin solution (mL/L) (Table 9) | 12 | 12 | 12 | 12 |
| Yeast trace metals solution (mL/L) (Table 9) | 10 | 10 | 10 | 10 |
| succinate (0.5M, pH 5.0) (mL/L) (Table 7) | 100 | 0 | 0 | 0 |
| 95% (v/v) ethanol (mL/L) | 0 | 0 | 0 | 237 |

Production of amorpha-4,11-diene was induced at an OD$_{600}$ of approximately 50.

Figure 12B:
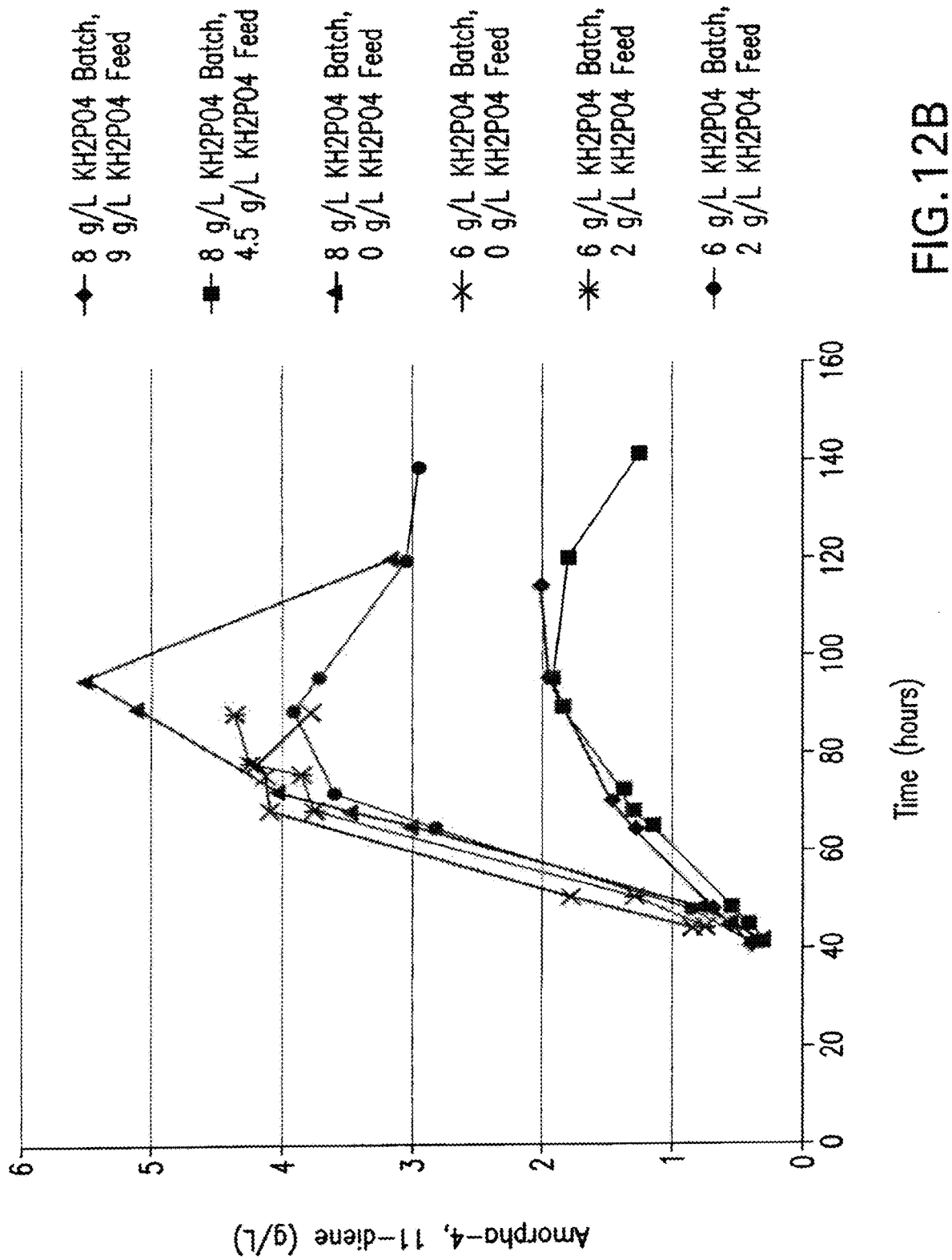
Figure 12C:
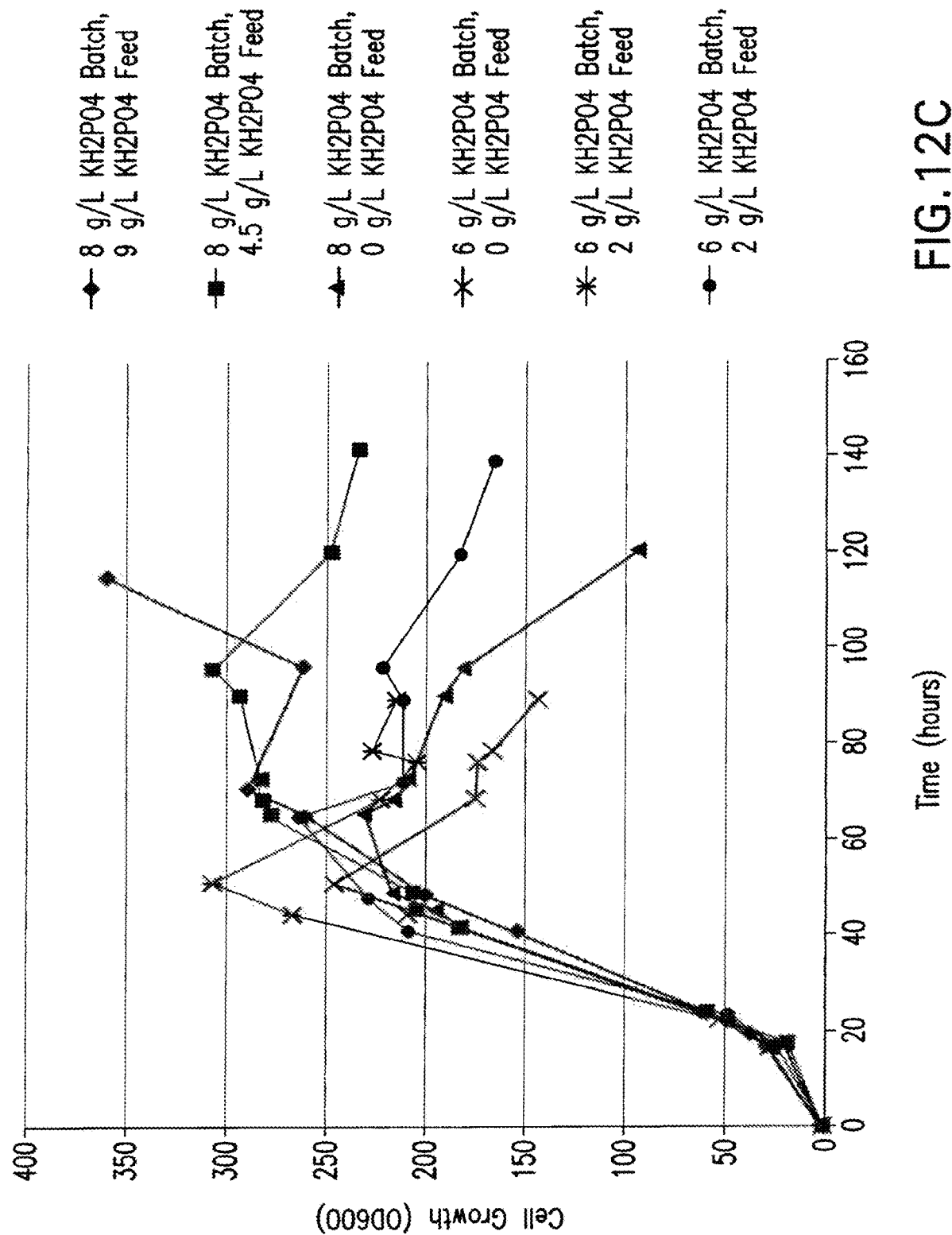

As shown in Table 20 and FIG. 12B, supplying 8 g/L KH$_2$PO$_4$ in the batch medium and no phosphate in the feed medium showed the best amorpha-4,11-diene production at 5.52 g/L. Under these conditions, phosphate in the batch medium was consumed by 40 hours, and cell growth was consequently restricted (i.e., less carbon went to biomass and more carbon went to production of amorpha-4,11-diene) (FIG. 12C).

TABLE 20

Amorpha-4, 11-diene production by strain Y337 with glucose feeds and phosphate restriction

| Batch KH$_2$PO$_4$ (g/L) | Feed KH$_2$PO$_4$ (g/L) | Maximum Feed Rate (g/h/L) [a] | Stationary Feed Rate (g/h/L) [a] | Time to Max Titer (hr) | Maximum OD | Maximum Titer (g/L) |
|---|---|---|---|---|---|---|
| 8 | 9 | 10 | 10 | 114.86 | 360 | 2 |
| 8 | 4.5 | 10 | 10 | 95.62 | 307 | 1.92 |
| 8 | 0 | 10 | 10 | 95.66 | 231 | 5.52 |
| 6 | 0 | 10 | 10 | 78.30 | 246 | 4.2 |
| 6 | 2 | 10 | 10 | 88.98 | 307 | 4.36 |
| 6 | 2 | 10 | 10 | 89.21 | 263 | 3.91 |
| 6 | 2 | 10 | 5 | 119.73 | 274 | 2.98 |

[a] g/hr/L is g substrate/hr/L bioreactor volume.

Example 12

This example describes the production of amorpha-4,11-diene by host cells in fed batch, carbon-restricted fermentation with phosphate restriction and a mixed glucose/ethanol feed.

Y337 seed cultures were prepared and used to inoculate bioreactors containing phosphate-restricted batch medium (Table 19) as described in Example 3. Fermentations were carried out, and samples were analyzed, essentially as described in Example 4 with the following modifications.

During the early phase of the fermentation, some of the glucose in the batch medium was converted to ethanol. The bioreactor culture was allowed to grow until the glucose and the ethanol in the batch medium was depleted, at which point, an exponential feed was initiated for which phosphate-restricted mixed feed medium (Table 19) was pumped into the bioreactor at the rate defined by the following equations:

$$F = V \mu_{set} S_B e^{\mu_{set}(t-t_0)}$$

$$V = V_0 + V_{feed}$$

F is the substrate mass flow rate (g/hr), V is the liquid volume in the bioreactor at a given time (L), $S_B$ is the concentration of substrate in the batch media (20 g/L), $\mu_{set}$ is the specific feed rate (0.087 hr$^{-1}$), t is the batch age (hr), $t_0$ is the batch age when the feed was initiated (hr), $V_0$ is the initial volume in the bioreactor, and $V_{feed}$ is the total volume of feed added to the bioreactor at a given time (L). The exponential feed phase continued until the ratio of F/V reached a preset maximum feed rate in units of g substrate/hr/L bioreactor volume (Table 21). After reaching this maximum, the ratio of F/V was maintained constant for the remainder of the process at a preset stationary feed rate (Table 21).

Production of amorpha-4,11-diene was induced at an OD$_{600}$ of approximately 50.

Figure 13A:
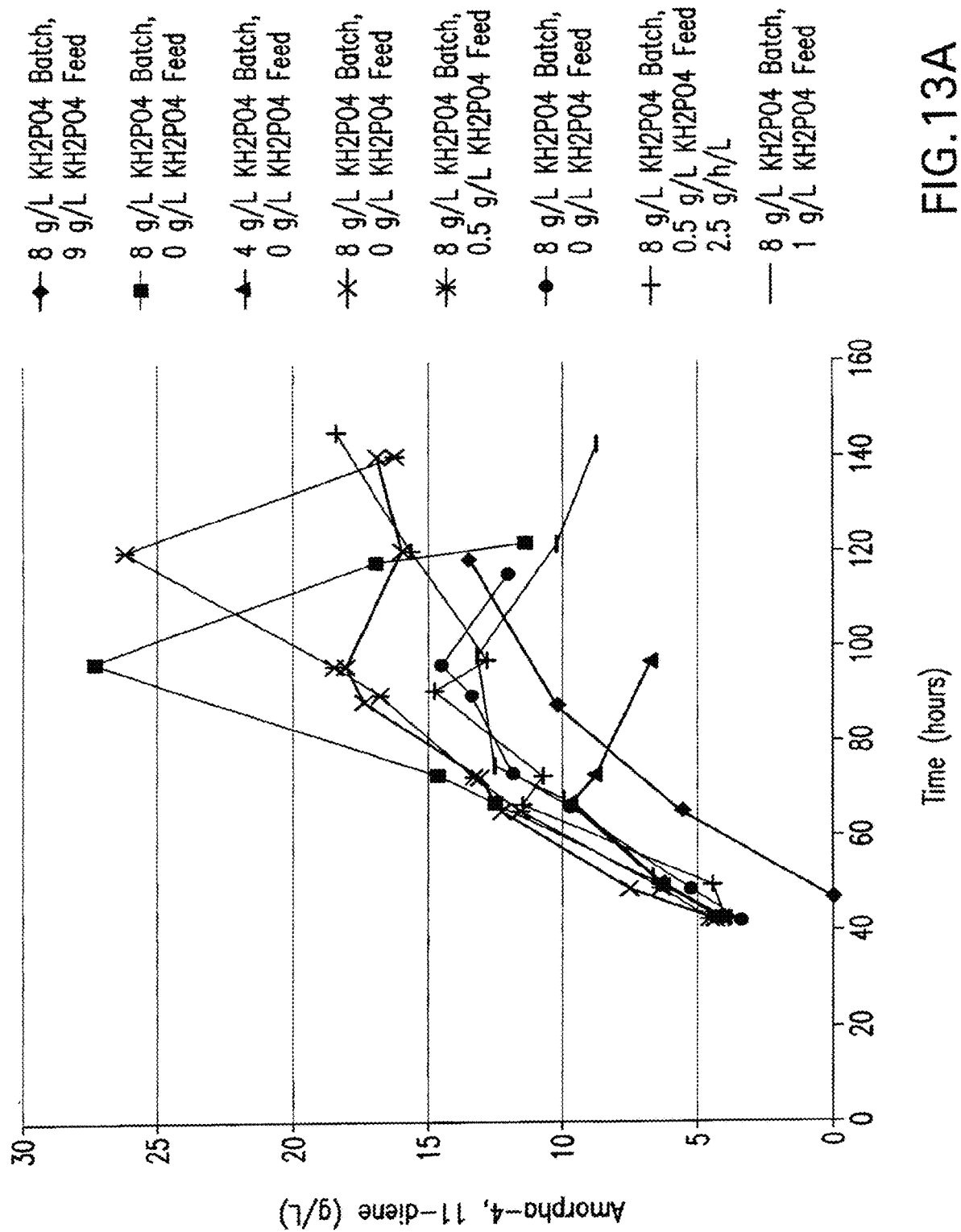
FIG. 13 shows cell growth (A) and amorpha-4,11-diene production (B) by strain Y337 under carbon- and phosphate-restriction using a glucose/ethanol mixed feed.
Figure 13B:
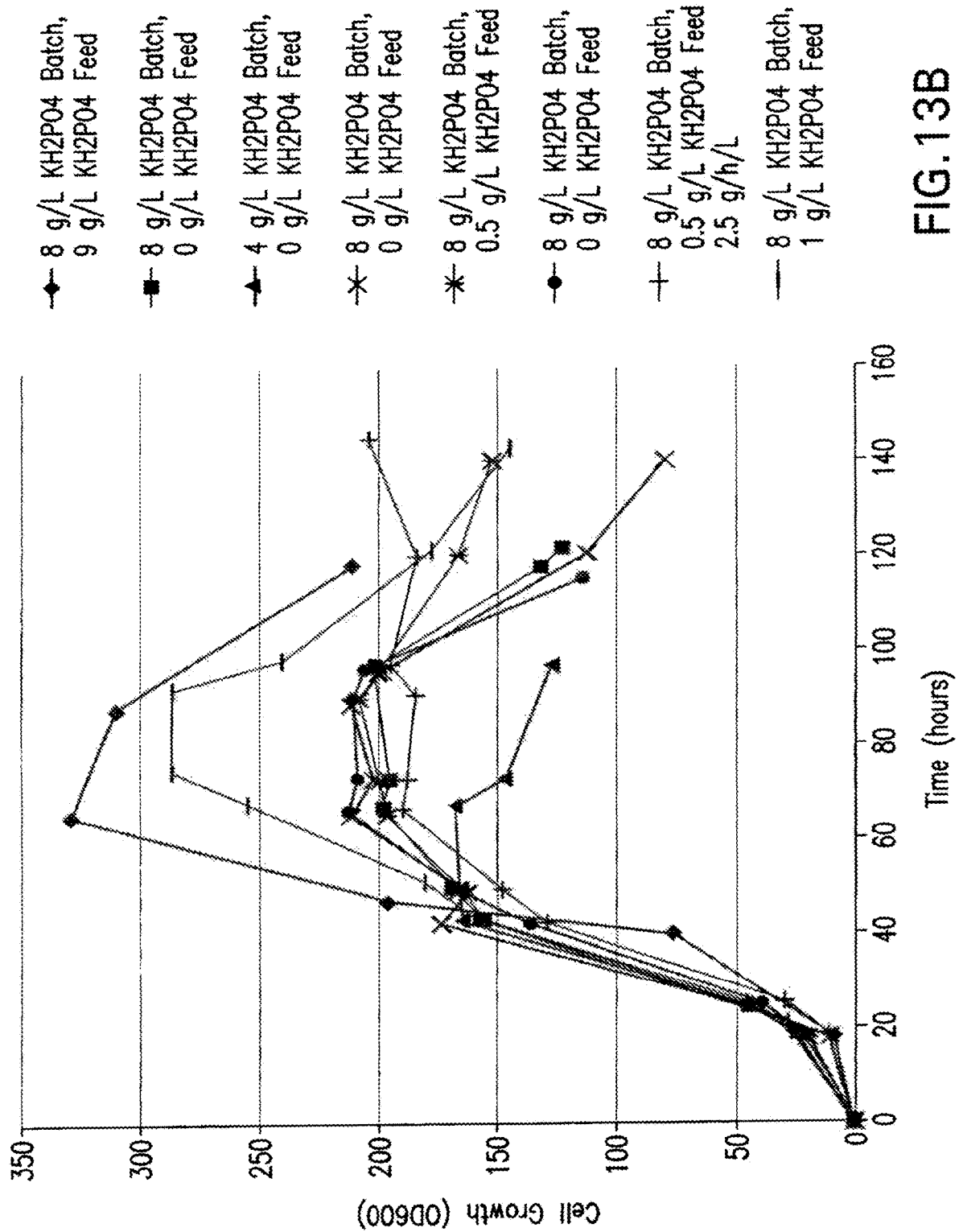

As shown in Table 21 and FIG. 13A, supplying 8 g/L KH$_2$PO$_4$ in the batch medium and 0 to 0.5 g/L KH$_2$PO$_4$ in the feed medium showed the best amorpha-4,11-diene production at over 26 to 27 g/L. Under these conditions, phosphate in the batch medium was consumed by 40 hours, and cell growth was consequently restricted (i.e., less carbon went to biomass and more carbon went to production of amorpha-4,11-diene) (FIG. 13B). Compared to 0 g/L KH$_2$PO$_4$ in the feed medium, 0.5 g/L KH$_2$PO$_4$ in the feed medium allowed cell growth and amorpha-4,11-diene production to continue for an additional 24 hours.

TABLE 21

Amorpha-4, 11-diene production by strain Y337 with mixed feeds and phosphate restriction

| Batch KH$_2$PO$_4$ (g/L) | Feed KH$_2$PO$_4$ (g/L) | Maximum Feed Rate (g/h/L) [a] | Stationary Feed Rate (g/h/L) [a] | Time to Maximum Titer (hr) | Maximum OD | Maximum Titer (g/L) |
|---|---|---|---|---|---|---|
| 8 | 9 | 8.6 | 8.6 | 118.17 | 329 | 12.69 |
| 8 | 9 | 8.6 | 4.3 | 94.85 | 205 | 10.31 |
| 8 | 0 | 8.6 | 8.6 | 96.83 | 201 | 27.36 |
| 4 | 0 | 8.6 | 8.6 | 67.17 | 168 | 9.68 |
| 8 | 0 | 8.6 | 4.3 | 120.20 | 209 | 16.27 |
| 4 | 0 | 8.6 | 4.3 | 120.20 | 181 | 17.94 |
| 8 | 0 | 8.6 | 8.6 | 95.93 | 212 | 18.07 |
| 8 | 0.5 | 8.6 | 8.6 | 120.33 | 209 | 26.23 |
| 8 | 0 | 10 | 10 | 96.13 | 213 | 14.55 |
| 8 | 0.5 | 10 | 10; dropped to 2.5 at 67 hrs | 145.16 | 204 | 18.38 |
| 8 | 1 | 10 | 10 | 97.69 | 287 | 13.15 |

[a] g/hr/L is g substrate/hr/L bioreactor volume.

Example 13

This example describes methods for generating *Escherichia coli* host strains that harbor heterologous nucleotide sequences encoding enzymes including enzymes of the MEV pathway and terpene synthases integrated in their genomes.

Figure 14:
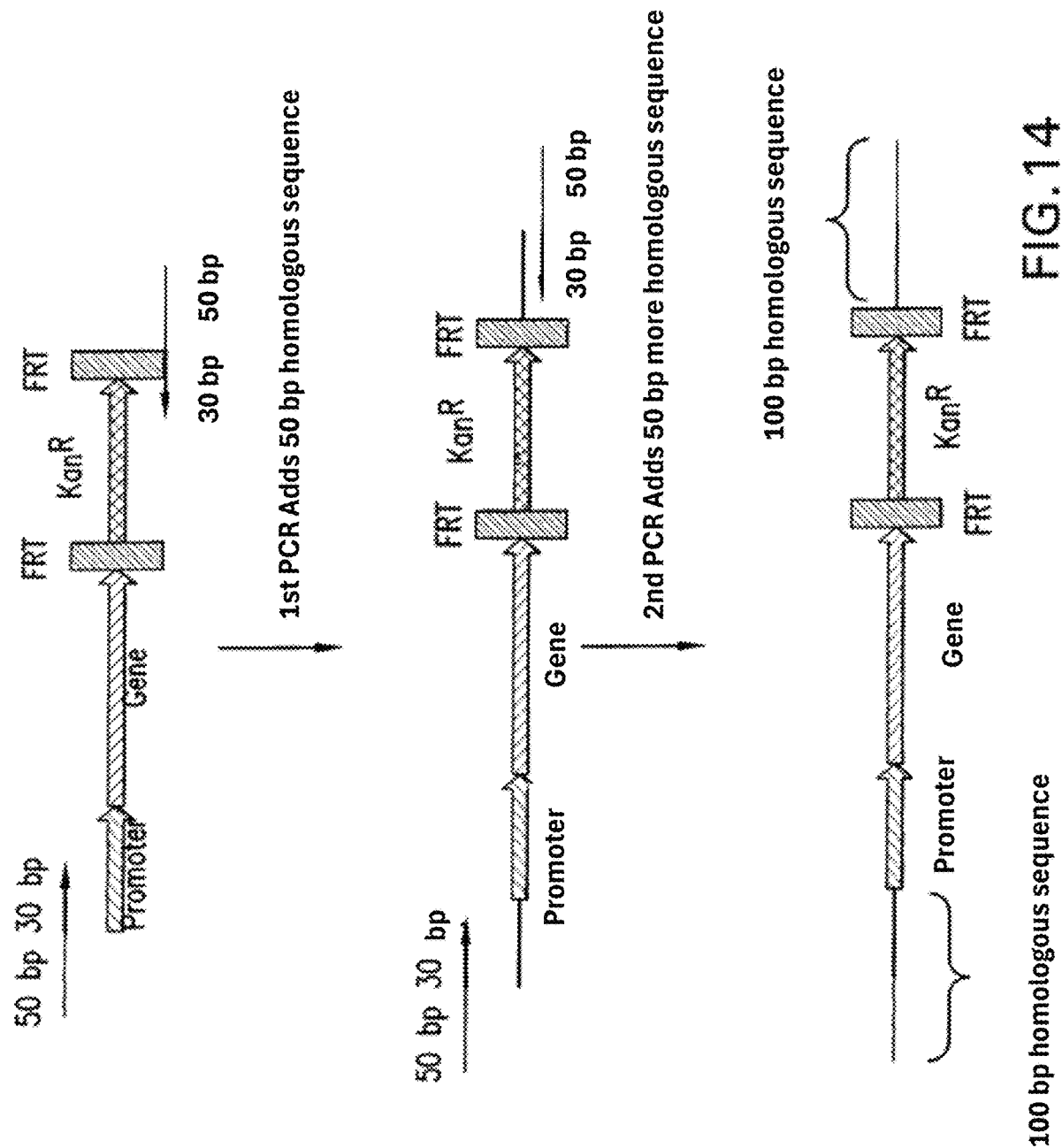
FIG. 14 illustrates the generation of 100 nucleotide long genomic locus-specific sequences flanking promoter-gene-FRT-Kan-FRT cassettes useful in the integration of heterologous nucleotide sequences into the genome of *Escherichia coli*.

Genomic integrations were carried out using a variation of the procedure outlined by Datsenko & Wanner ((2000) *Proc. Natl. Acad. Sci. USA* 97:6640-6645). The method employs plasmids that comprise a T7 promoter-gene of interest-FRT-Kan-FRT cassette. The cassette is flanked on each side by approximately 100 nucleotides that are homologous to the regions flanking the genomic locus targeted for the integration of the cassette. The flanking regions are created by PCR amplifying the cassette using primers that comprise a stretch of approximately 30 nucleotides that is homologous to either the 3' or the 5' end of the cassette, and another stretch of approximately 50 nucleotides that is homologous to the regions flanking the genomic locus (FIG. 14). The resulting PCR product is used as the template in a 2$^{nd}$ PCR reaction that adds another 50 nucleotides of flanking sequence homology on either end of the cassette (FIG. 14). The cassette with its flanking sequences is electroporated into electro-competent *Escherichia coli* cells carrying a plasmid that encodes the Red recombinase protein. Kanamycin ("Kan") resistant colonies are screened by colony PCR. Positive recombinants are treated with P1-phage, and the integration is transferred to a fresh strain via P1-transduction. The resulting strain is transformed with a plasmid that encodes the FLP recombinase, the activity of which causes the Kan gene to be excised from the cassette, leaving behind the T7 promoter-gene of interest at the targeted genomic locus. The final host strain is cured of the FLP recombinase.

Applying the described method, host strain B1060 was generated by integrating a DNA fragment encoding a β-farnesene synthase ("FS") into the Lac operon of *Escherichia coli* strain B1021 (MM294(DE3)(T1R)). To this end, *Escherichia coli* strain MM294 (ATCC33625) was made DE3 using the DE3 lysogenization kit (Novagen, Darmstadt, Germany), and was made resistant to T1 phage by growing the strain in the presence of excess T1 phage, thus yielding strain B1021. A FRT-Kan-FRT cassette was inserted using a modification of the QuikChange methodology (Geiser et al. (2001) Biotechniques 31:88-92) into expression plasmid pAM454, which encodes the β-farnesene synthase of Artemisia annua (GenBank accession number AY835398), codon-optimized for expression in Escherichia coli, under the control of the T7 promoter, thus yielding expression plasmid pAM617. Because the T7-FS-FRT-Kan-FRT cassette in pAM617 is already flanked by sequences from the mhpR and cynX loci (SEQ ID NO: 70), only one round of PCR amplification was necessary to create 100 nucleotide sequences homologous to the mhpR or the cynX sequences that flank the Lac operon. MM294(DE3) host cells harboring expression plasmid pAM88 (encodes the Red recombinase) were grown at 30° C. in LB medium containing 50 ug/mL carbenicillin and 1 mM arabinose to an OD600 of 0.6. The cells were harvested, rendered electro-competent, and transformed with the PCR product. Colonies were obtained after 2 days of growth at 30° C. on LB agar containing 50 ug/mL kanamycin, and the correct integrant was selected by colony PCR. The integration was transferred to a host strain B1021 (MM294(DE3)(T1R)) via P1-transduction, and the resulting strain was made competent and was transformed with expression plasmid pAM89 (encodes the FLP recombinase). Colonies were obtained after 2 days of growth at 30° C. on LB agar containing 50 ug/mL carbenicillin. One colony was isolated and grown at 42° C. in LB media to lose plasmid pAM89, yielding strain B1060 (MM294(DE3)(T1R) lac::T7-FS).

Figure 15:
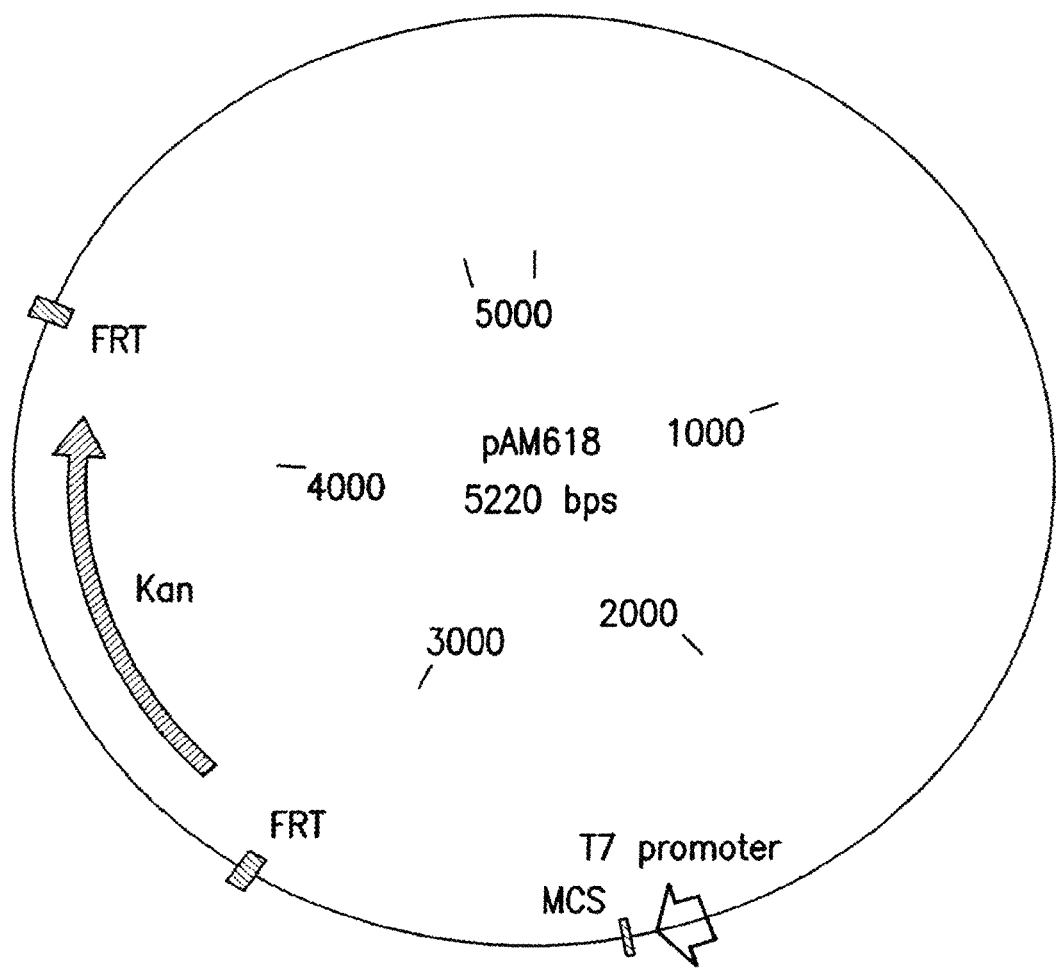
FIG. 15 shows a map of plasmid pAM618.

Host strain B1061 was generated by integrating a DNA fragment encoding a mevalonate kinase ("MK") into the ackpta operon of Escherichia coli strain B1021. To this end, a DNA fragment encoding the mevalonate kinase of Saccharomyces cerevisiae, codon-optimized for expression in Escherichia coli (SEQ ID NO: 71), was inserted into the NdeI BamHI restriction sites of plasmid pAM618. Plasmid pAM618 comprises a T7 promoter followed by a multiple cloning site (MCS) and a FRT-KanR-FRT cassette (SEQ ID NO: 72, FIG. 15). The resulting T7-MK-FRT-Kan-FRT cassette was put through two rounds of PCR amplification as described above to create 100 nucleotide flanking sequences homologous to the ack pta operon. The final PCR product was introduced into Escherichia coli strain B1021 as described above, yielding strain B1061 (MM294(DE3)(T1R) ackpta::T7-MK). The integration was also transferred to host strain B1060, yielding strain B1124 (MM294(DE3)(T1R) lac::T7-FS ackpta::T7-MK).

Host strain B1062 was generated by integrating a DNA fragment encoding a phosphomevalonate kinase ("PMK") into the poxB locus of Escherichia coli strain B1021. To this end, a DNA fragment encoding the phosphomevalonate kinase of Saccharomyces cerevisiae, codon-optimized for expression in Escherichia coli (SEQ ID NO: 73), was inserted into the NdeI BamHI restriction sites of plasmid pAM618. The resulting T7-PMK-FRT-Kan-FRT cassette was put through two rounds of PCR amplification as described above to create 100 nucleotide flanking sequences homologous to the poxB locus. The final PCR product was introduced into Escherichia coli strain B1021 as described above, yielding strain B1062 (MM294(DE3)(TIR) poxB:: T7-PMK).

Host strain B1273 was generated by integrating a DNA fragment encoding a HMG-CoA reductase ("HMGR") into the ldhA locus of Escherichia coli strain B1021. To this end, a DNA fragment encoding the HMGR of Staphylococcus aureus (mva; GenBank accession number BA000017, REGION: 2688925..2687648) was inserted into the EcoRI BamHI restriction sites of plasmid pAM618 after treating the EcoRI restriction site with Klenow fragment. The resulting T7-mvaA-FRT-Kan-FRT cassette was put through two rounds of PCR amplification as described above to create 100 nucleotide flanking sequences homologous to the ldhA locus. The final PCR product was introduced into Escherichia coli strain B1021 as described above, yielding strain B1273 (MM294(DE3)(T1R) ldhA::T7-mvaA).

While many specific examples have been provided, the above description is intended to illustrate rather than limit the embodiments provided herein. Many variations of the embodiments will become apparent to those skilled in the art upon review of this specification. The scope of the embodiments should, therefore, be determined not with reference to the above description, but instead should be determined with reference to the appended claims along with their full scope of equivalents.

What is claimed is:

1. A method for producing a heterologous $C_5$-$C_{20}$ isoprenoid compound in a yeast host cell, the method comprising:
  (a) obtaining a plurality of yeast host cells that are capable of making the heterologous $C_5$-$C_{20}$ isoprenoid compound, each said yeast host cell comprising one or more heterologous nucleic acids capable of expressing each enzyme of the MEV pathway or each enzyme of the DXP pathway;
  (b) culturing the yeast host cells in media comprising glucose and glucose-converted ethanol and an ethanol-only feed, wherein the culturing includes a period of time where the host cells are carbon-limited to yield a fermentation reaction mixture comprising medium, cells, and the heterologous $C_5$-$C_{20}$ isoprenoid compound; and
  (c) recovering the heterologous $C_5$-$C_{20}$ isoprenoid compound from the medium,
  wherein the yeast host cells produce from 10 to 40 grams of the heterologous $C_5$-$C_{20}$ isoprenoid compound per liter of fermentation reaction mixture after 4 to 12 days of culturing, and
  wherein the heterologous C5-C20 isoprenoid compound is farnesene.

2. The method of claim 1, wherein the yeast host cells produce between 30 and 40 grams/liter of farnesene.

3. The method of claim 1, wherein the yeast host cells produce greater than about 10 grams/liter of farnesene.

4. The method of claim 1, wherein the yeast host cells produce greater than about 20 grams/liter of farnesene.

5. The method of claim 1, wherein the yeast host cells are S. cerevisiae.

6. The method of claim 1, wherein each said yeast host cell comprises one or more heterologous nucleic acids capable of expressing an acetyl-CoA acetyltransferase, an HMG-COA synthase, an HMG-CoA reductase, a mevalonate kinase, a phosphomevalonate kinase and a mevalonate pyrophosphate decarboxylase.

7. The method of claim 1, wherein the medium comprises a batch medium and a feed medium.

8. The method of claim 7, wherein the batch medium is supplied with 30 to 35 grams/liter phosphate.

9. The method of claim 1, wherein the yeast host cells are maintained under carbon-limited conditions after the glucose and glucose-converted ethanol are depleted from the batch medium.

10. The method of claim 7, comprising an overall ethanol consumption rate of 0 to 2.1 grams ethanol per gram of dry cell weight per day.

11. The method of claim 7, wherein the batch medium is supplied with 30 to 35 grams/liter phosphate.

12. The method of claim 7, wherein the feed medium is supplied at a maximum feed rate of 5 grams/hour/liter and a stationary feed rate of 1.25 grams/hour/liter to 2.5 grams/hour/liter.

13. The method of claim 7, wherein the batch medium comprises glucose at 39.03 grams/liter and the feed medium is ethanol.

14. The method of claim 13, wherein the feed medium is 95% ethanol.

15. The method of claim 8, wherein the phosphate is supplied to the batch medium as potassium dihydrogen phosphate ($KH_2PO_4$).

* * * * *